United States Patent
Gross

(10) Patent No.: US 9,611,253 B2
(45) Date of Patent: Apr. 4, 2017

(54) SOLID FORMS COMPRISING OPTICALLY ACTIVE PYRAZOLYLAMINOQUINAZOLINE, COMPOSITIONS THEREOF, AND USES THEREWITH

(71) Applicant: AMBIT BIOSCIENCES CORPORATION, San Diego, CA (US)

(72) Inventor: Timothy David Gross, San Diego, CA (US)

(73) Assignee: Ambit Biosciences Corporation, San Diego, CA (US)

(*) Notice: Subject to any disclaimer, the term of this patent is extended or adjusted under 35 U.S.C. 154(b) by 0 days.

(21) Appl. No.: 14/381,188

(22) PCT Filed: Feb. 27, 2013

(86) PCT No.: PCT/US2013/028011
§ 371 (c)(1),
(2) Date: Aug. 26, 2014

(87) PCT Pub. No.: WO2013/130600
PCT Pub. Date: Sep. 6, 2013

(65) Prior Publication Data
US 2015/0025092 A1    Jan. 22, 2015

Related U.S. Application Data

(60) Provisional application No. 61/605,127, filed on Feb. 29, 2012.

(51) Int. Cl.
*C07D 403/12*    (2006.01)

(52) U.S. Cl.
CPC .................. *C07D 403/12* (2013.01)

(58) Field of Classification Search
CPC .................................... C07D 403/12
USPC ..................... 514/266.23; 544/284
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |

(Continued)

FOREIGN PATENT DOCUMENTS

| | | |
|---|---|---|
| WO | 2004/000224 A2 | 12/2003 |
| WO | 2010/009190 A1 | 1/2010 |

OTHER PUBLICATIONS

Blume-Jensen and Hunter, "Oncogenic kinase signaling," Nature 411(6835):355-365 (2001).
Burla et al., "SIR2004: an improved tool for crystal structure determination and refinement," J. Appl. Cryst. 38:381-388 (2005).
Burnett et al., "Testicular Expression of Adora3i2 in Adora3 Knockout Mice Reveals a Role of Mouse A3Ri2 and Human A3Ri3 Adenosine Receptors in Sperm," J. Biol. Chem. 285(44):33662-33670 (2010).
Chemburkar et al., "Dealing with the Impact of Ritonavir polymorphs on the late stages of Bulk Drug Process Development," Org. Process Res. Dev. 4:413-417 (2000).
Farrugia, "ORTEP-3 for Windows—a version of ORTEP-III with a Graphical User Interface (GUI)," J. Appl. Cryst. 30:565 (1997).
Gould, "Salt selection for basic drugs," Int. J. Pharm. 33: 201-217 (1986).

(Continued)

*Primary Examiner* — Paul V Ward
(74) *Attorney, Agent, or Firm* — Jones Day

(57) ABSTRACT

Solid forms comprising pyrazolylaminoquinazoline, compositions comprising the solid forms, methods of making the solid forms and methods of their use for the treatment of various diseases and/or disorders are disclosed.

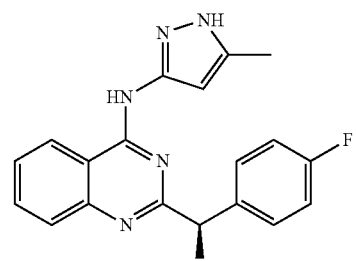

(I)

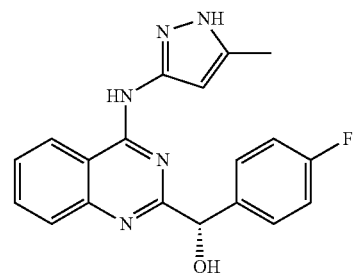

(II)

18 Claims, 43 Drawing Sheets

(56) References Cited

U.S. PATENT DOCUMENTS

| | | |
|---|---|---|
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 8,703,943 B2 | 4/2014 | Holladay et al. |
| 8,912,324 B2 | 12/2014 | Holladay et al. |
| 2010/0317659 A1* | 12/2010 | Abraham .............. C07D 401/14 514/234.5 |
| 2012/0053193 A1 | 3/2012 | Holladay et al. |

OTHER PUBLICATIONS

Hölzer et al., "Kα1,2 and Kβ1,3 x-ray emission lines of the 3d transition metals," Phys. Rev. A 56(6) 4554-4568 (1997).

Inoue et al., "A3 adenosine receptor inhibition improves the efficacy of hypertonic saline resuscitation," Shock 35 (2):178-183 (2011).

Krause and Van Etten, "Tyrosine kinases as targets for cancer therapy," N. Engl. J. Med. 353(2):172-187 (2005).

Lee et al., "A3 adenosine receptor knockout mice are protected against ischemia- and myoglobinuria-induced renal failure," Am. J. Physiol. Renal Physiol. 284(2):F267-F273 (2002) (Epub Oct. 15, 2002).

Otwinowski and Minor, "Processing of x-ray diffraction data collected in oscillation mode," Methods Enzymol. 276:307-326 (1997).

Plowman et al., "Receptor Tyosine Kinases as Targets for Drug Intervention," DN&P 7(6):334-339 (1994).

Pugliese et al., "A3 adenosine receptor antagonists delay irreversible synaptic failure caused by oxygen and glucose deprivation in the rat CA1 hippocampus in vitro," Br. J. Pharmacol. 147:524-532 (2006).

Santus and Baker, "Osmotic drug delivery: a review of the patent literature," J. Controlled Release 35:1-21 (1995).

Serajuddin, "Salt formation to improve drug solubility,"Adv. Drug Deliv. Rev. 59(7):603-616 (2007) (Epub May 29, 2007).

Verma et al., "Formulation aspects in the development of osmotically controlled oral drug delivery systems," J. Controlled Release 79:7-27 (2002).

Vippagunta et al., "Crystalline solids," Adv. Drug. Deliv. Rev. 48(1):3-26 (2001).

Yu, "Amorphous pharmaceutical solids: preparation, characterization and stabilization," Adv. Drug Deliv. Rev. 48 (1):27-42 (2001).

Bernstein, "Crystal structure prediction and polymorphism," ACA Transactions 39:14-23 (2004).

Peterson et al., "Expanding the scope of crystal form evaluation in pharmaceutical science," J. Pharm. Pharm. Sci. 9(3):317-326 (2006).

* cited by examiner

SOLID FORMS COMPRISING OPTICALLY ACTIVE PYRAZOLYLAMINOQUINAZOLINE, COMPOSITIONS THEREOF, AND USES THEREWITH

1. RELATED APPLICATIONS

This application is a §371 national phase application of International Patent Application No. PCT/US2013/028011, filed Feb. 27, 2013, which claims the benefit of the priority of U.S. Provisional Application No. 61/605,127, filed Feb. 29, 2012, the disclosure of which is incorporated herein by reference in their entireties.

2. FIELD

Provided herein are solid forms comprising pyrazolylaminoquinazoline, compositions comprising the solid forms, methods of making the solid forms and methods of their use for the treatment of various diseases and/or disorders.

3. BACKGROUND

The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Provided herein are embodiments addressing the need for solid forms of certain pyrazolylaminoquinazoline compounds chemically named (R)-(4-fluorophenyl)(4-((5-methyl-1H-pyrazol-3-yl)amino)quinazolin-2-yl)methanol ("Compound 6") and (S)-(4-fluorophenyl)(4-((5-methyl-1H-pyrazol-3-yl)amino)quinazolin-2-yl)methanol ("Compound 0"). Compound 6 and Compound 0 were disclosed, respectively, in U.S. patent application Ser. Nos. 13/223,099 13/222,963, both filed on Aug. 31, 2011, as JAK inhibitors useful for various therapeutic applications including myeloproliferative disorders, blood cancer, solid tumor, inflammatory diseases, immune system disorder, metabolic disorder and growth disorder. Provided herein are embodiments in which certain novel solid forms include particular advantageous physical properties making them useful, e.g., for manufacturing processing, formulation and/or storage, while also possessing particularly advantageous biological properties, such as bioavailability and biological activity.

4. SUMMARY

Embodiments herein provide solid forms comprising the compound chemically named (R)-(4-fluorophenyl)(4-((5-methyl-1H-pyrazol-3-yl)amino)quinazolin-2-yl)methanol ("Compound 6"). Compound 6 can be synthesized or obtained according to any method apparent to those of skill in the art based upon the teachings herein, including the methods described in the Examples below. Compound 6 can also be prepared according to the methods described in U.S. Provisional Patent App. No. 61/379,286, filed Sep. 1, 2010 and U.S. patent application Ser. No. 13/223,099, filed Aug. 31, 2011, the entireties of each of which is incorporated by reference herein. In its free base form, Compound 6 has the following structure (I):

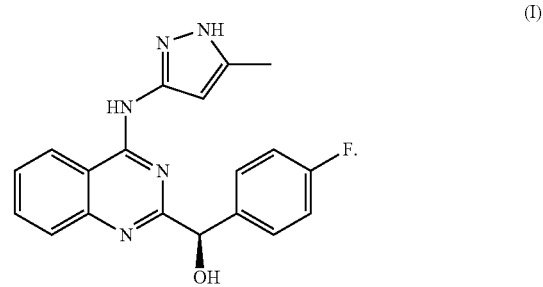 [SMILES: Cc1cc(Nc2nc([C@@H](O)c3ccc(F)cc3)nc3ccccc23)n[nH]1]

In certain embodiments, the solid forms are single-component crystal forms of the free base of Compound 6. In certain embodiments, the solid forms are multiple-component crystal forms, including, but not limited to, salts, co-crystals and/or solvates, including hydrates, comprising Compound 6. In other embodiments, the solid forms are single-component amorphous forms of the free base of Compound 6. In other embodiments, the solid forms are multiple-component amorphous forms, including, but not limited to, salts of Compound 6. Without intending to be limited by any particular theory, the storage stability, compressibility, bulk density or dissolution properties of certain solid forms described herein are believed to be beneficial for manufacturing, formulation and bioavailability of Compound 6.

In particular embodiments, solid forms provided herein include solid forms comprising Compound 6, including, but not limited to, particular solid forms comprising the free base of Compound 6, as well as solid forms comprising salts of Compound 6, such as HBr salts, HCl salts, sulfate salts, mesylate salts (methanesulfonate salt), esylate salts (ethanesulfonate salt), besylate salts (benzenesulfonate salt) and tosylate salts (p-toluenesulfonate salt). In particular embodiments, salts comprising Compound 6 include esylate salt of Compound 6. In certain embodiments, solid forms provided herein include polymorphs, solvates (including hydrates) and cocrystals comprising Compound 6 and/or salts thereof. Certain embodiments herein provide methods of making, isolating and/or characterizing the solid forms provided herein.

In certain embodiments herein, provided are solid forms comprising the compound chemically named (S)-(4-fluorophenyl)(4-((5-methyl-1H-pyrazol-3-yl)amino)quinazolin-2-yl)methanol ("Compound 0"). Compound 0 can be synthesized or obtained according to any method apparent to those of skill in the art based upon the teachings herein, including the methods described in the Examples below. Compound 0 can also be prepared according to the methods described in U.S. Provisional Patent App. No. 61/379,280, filed Sep. 1, 2010 and U.S. patent application Ser. No. 13/223,963, filed Aug. 31, 2011, the entireties of each of which are incorporated by reference herein. In its free base form, Compound 0 has the following structure (II):

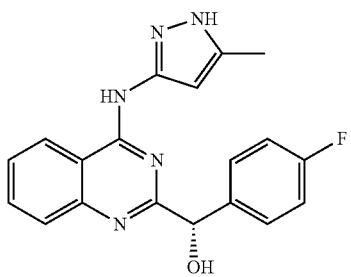

(II)

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising Compound 6 and a pharmaceutically acceptable diluent, excipient or carrier. The solid forms and the final drug products provided herein are useful, for example, for the treatment, prevention or management of diseases and disorders provided herein.

Certain embodiments herein provide methods of using the solid forms provided herein or pharmaceutical compositions comprising the solid forms provided herein for the treatment, prevention or management of diseases and disorders including, but not limited to, diseases or disorders that are modulated or otherwise affected by protein kinases (PK related diseases) or one or more symptoms or causes thereof. Certain embodiments herein provide methods for the treatment, prevention or management of diseases or disorders including, but not limited to, cancers, myeloproliferative disorder, nonmalignant proliferation diseases, atherosclerosis, restenosis, inflammatory diseases or disorders related to immune dysfunction, infectious diseases, and/or diseases or disorders that can be treated, prevented or managed by modulating the activity, binding or sub-cellular distribution of kinases, wherein such methods comprise administering to a subject, e.g., a human, in need of such treatment, prevention or management a therapeutically and prophylactically effective amount of a solid form provided herein. Such diseases or disorders are further described herein.

5. BRIEF DESCRIPTION OF THE DRAWINGS

FIG. 1. shows a representative DSC thermogram of a besylate salt of Compound 6 recrystallized from ethanol.

FIG. 2. shows a representative DSC thermogram of a besylate salt of Compound 6 recrystallized from isopropanol.

FIG. 3. shows a representative DSC thermogram of a esylate salt of Compound 6 recrystallized from ethanol.

FIG. 4. shows a representative DSC thermogram of a esylate salt of Compound 6 recrystallized from isopropanol.

FIG. 5. shows a representative DSC thermogram of a HBr salt of Compound 6 recrystallized from water.

FIG. 6. shows a representative DSC thermogram of a HBr salt of Compound 6 recrystallized from ethanol.

FIG. 7. shows a representative DSC thermogram of a HBr salt of Compound 6 recrystallized from isopropanol.

FIG. 8. shows a representative DSC thermogram of a HCl salt of Compound 6 recrystallized from water.

FIG. 9. shows a representative DSC thermogram of a HCl salt of Compound 6 recrystallized from ethanol.

FIG. 10. shows a representative DSC thermogram of a mesylate salt of Compound 6 recrystallized from methanol.

FIG. 11. shows a representative DSC thermogram of a mesylate salt of Compound 6 recrystallized from ethanol.

FIG. 12. shows a representative DSC thermogram of a tosylate salt of Compound 6 recrystallized from water.

FIG. 13. shows a representative DSC thermogram of a tosylate salt of Compound 6 recrystallized from isopropanol.

Form B of the esylate salt of Compound 6, (iii) Form C of the esylate salt of Compound 6 and (iv) Form D of the esylate salt of Compound 6.

Figure 19:
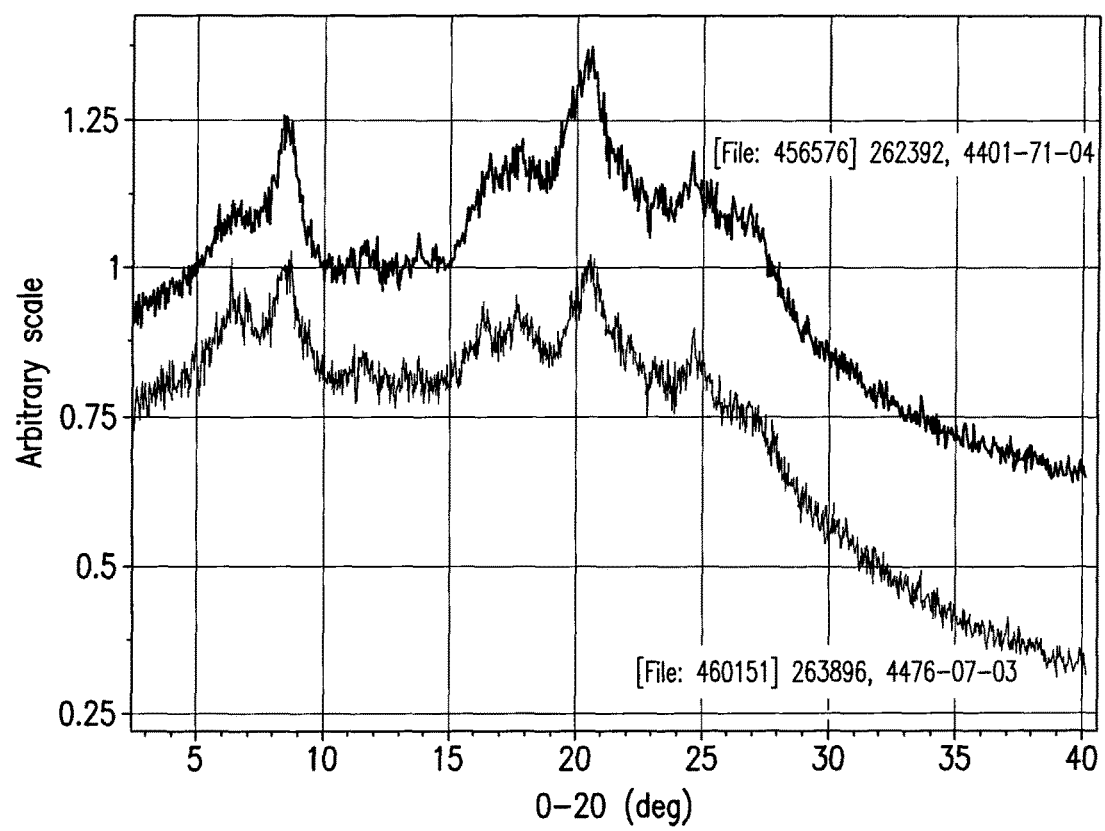

FIG. 19 shows disordered crystalline XRPD patterns from two new solid forms of the esylate salt of Compound 6 obtained from the polymorph screen described in Table 7B.

Figure 20:
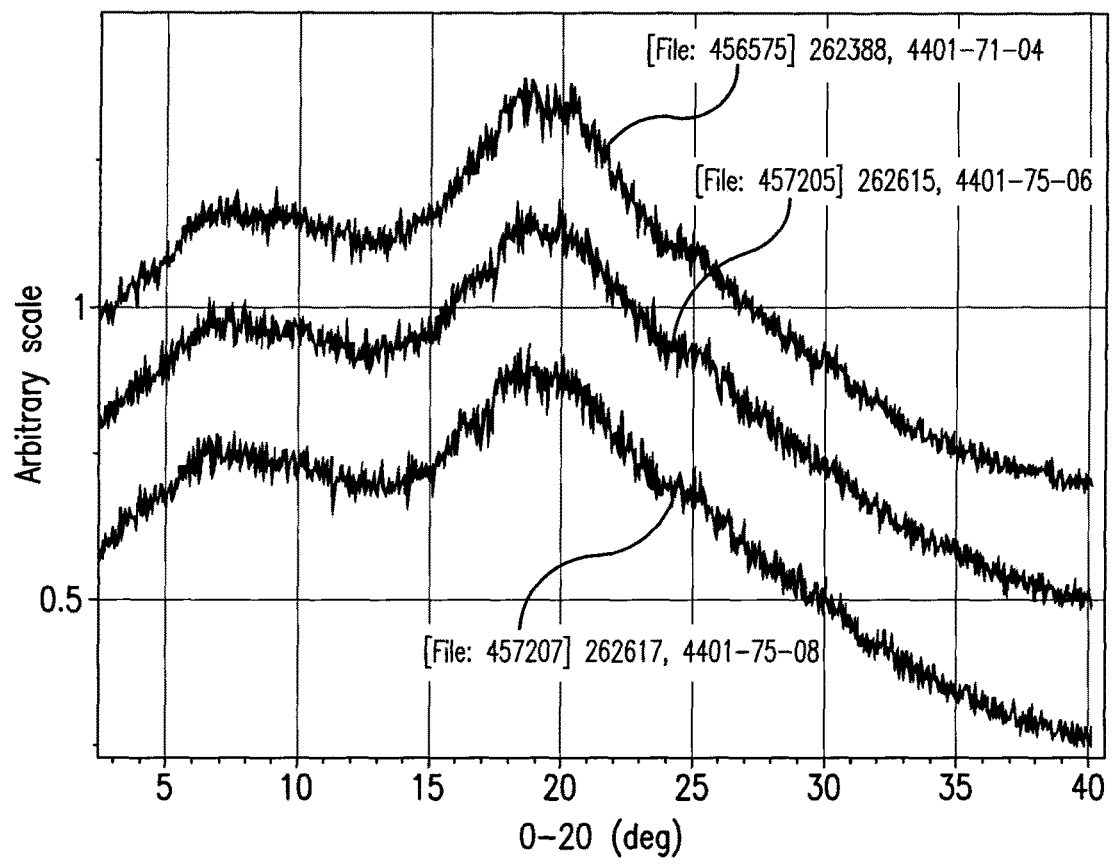

FIG. 20 shows XRPD patterns of amorphous forms of the esylate salt of Compound 6 obtained from the polymorph screen described in Table 7B.

Figure 21:
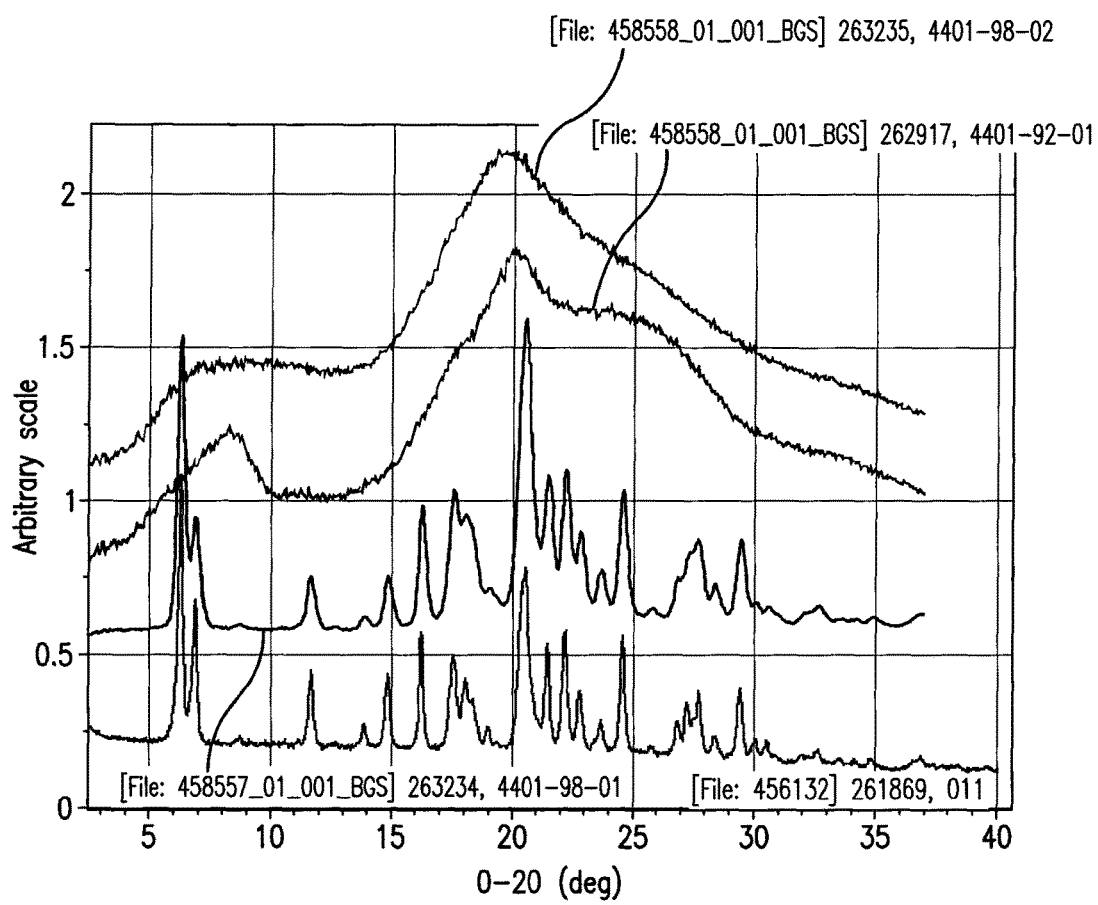

FIG. 21 shows overlay of XRPD patterns of various forms of the esylate salt of Compound 6 obtained from attempts to prepare amorphous esylate salt of Compound 6 under conditions described in Table 9.

Figure 22:
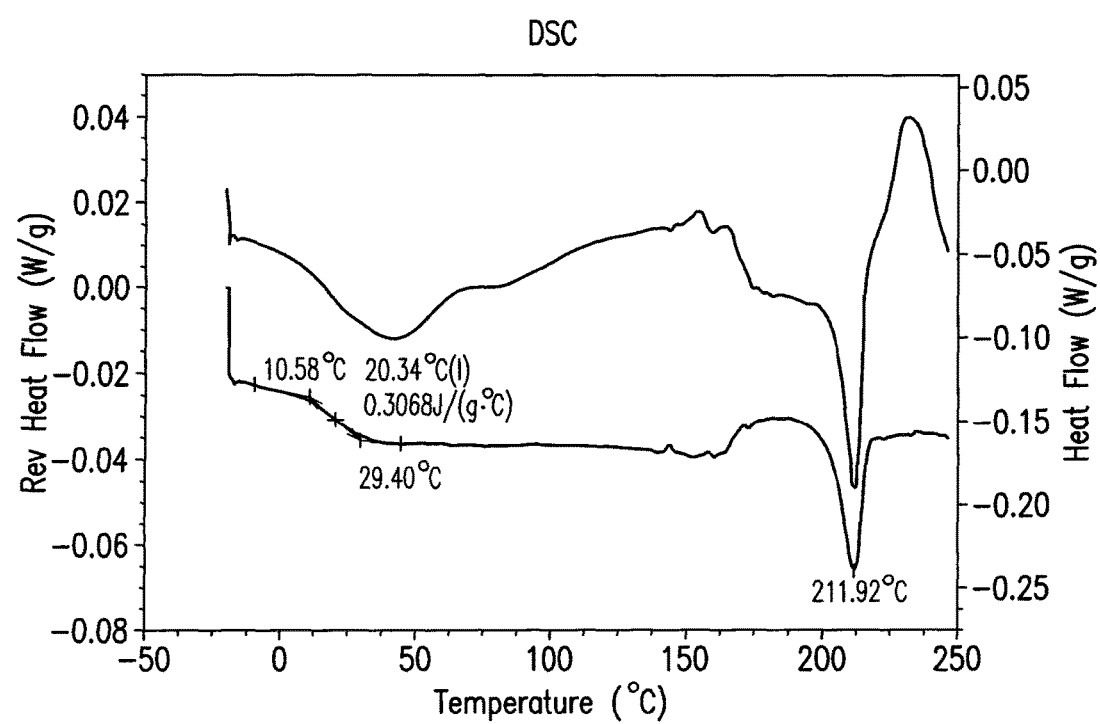

FIG. 22 shows provides a representative modulated DSC thermogram of an amorphous esylate salt of Compound 6.

Figure 23:
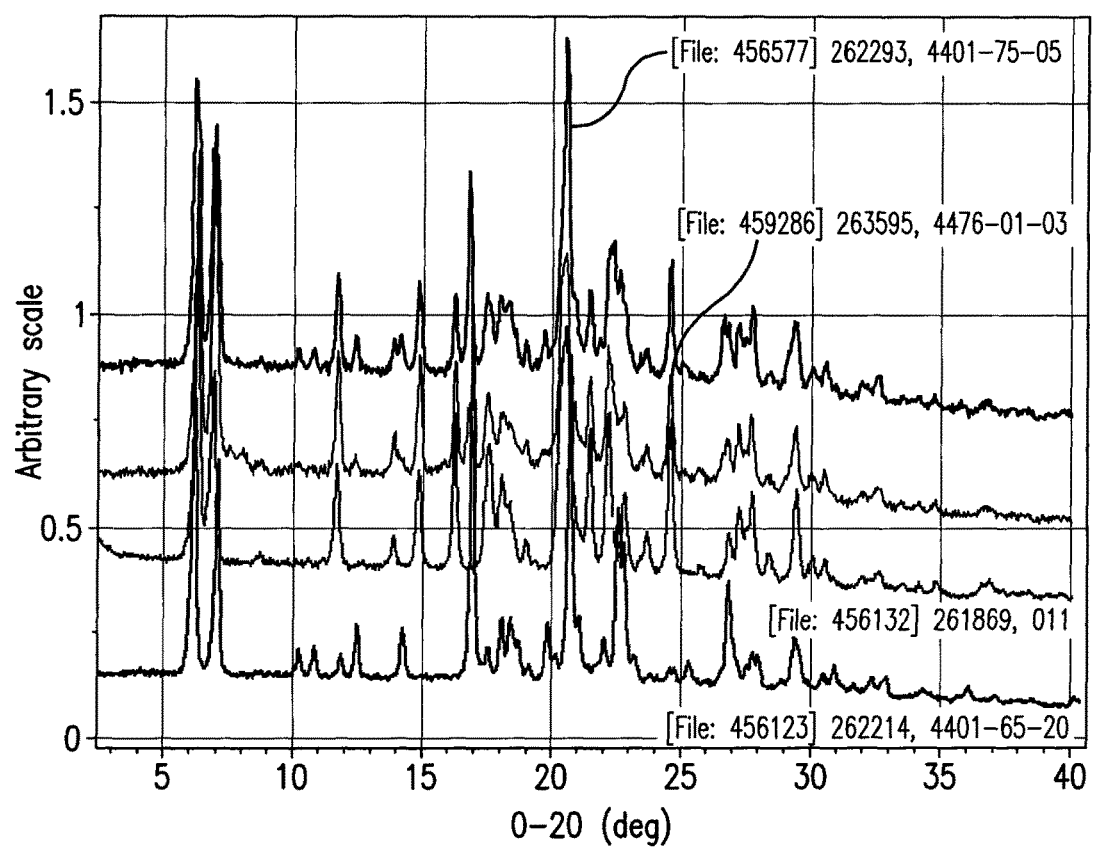

FIG. 23 shows representative XRPD patterns of Form B of the esylate salt of Compound 6 and mixtures of Forms A and B of the esylate salt of Compound 6, all obtained from the polymorph screen described in Table 7A.

Figure 24:
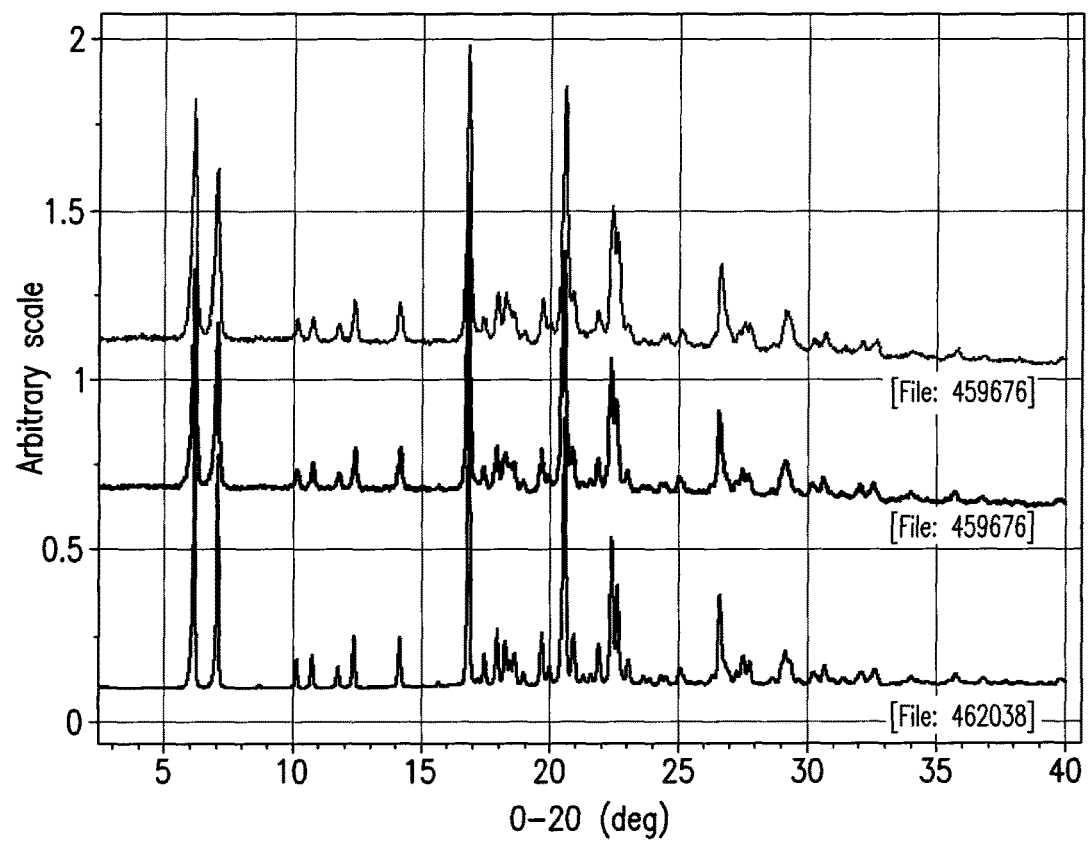

FIG. 24 shows representative XRPD patterns of Form B of the esylate salt of Compound 6.

Figure 25:
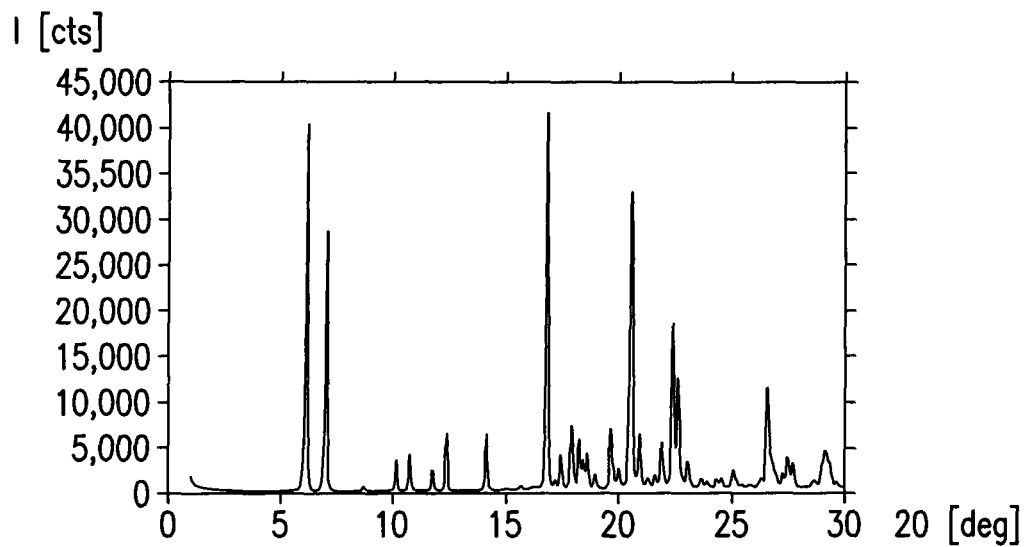

FIG. 25 shows an indexed XRPD pattern of Form B of the esylate salt of Compound 6.

Figure 26:
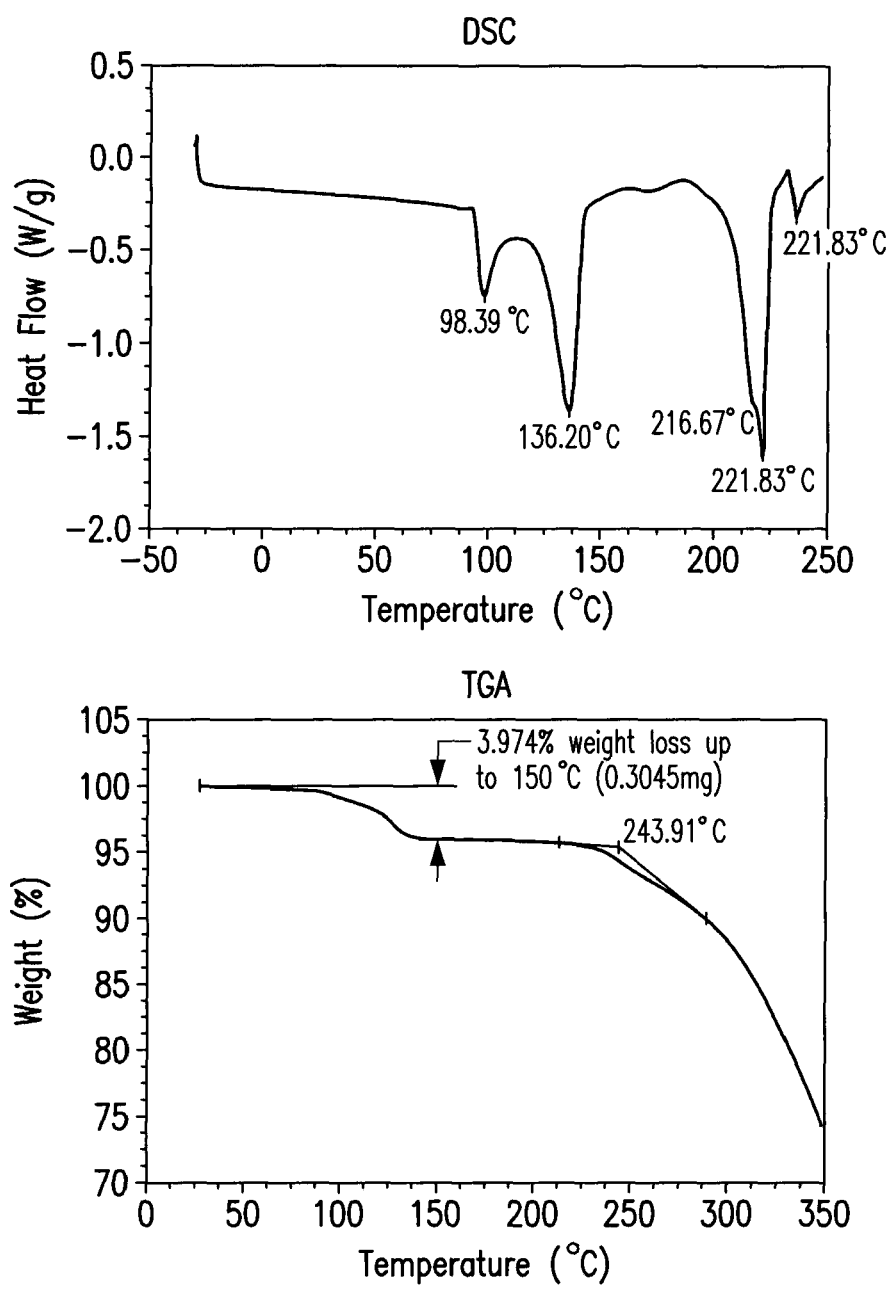

FIG. 26 shows a representative DSC (top graph) and TGA (bottom graph) thermograms for Form B of the esylate salt of Compound 6.

Figure 27:
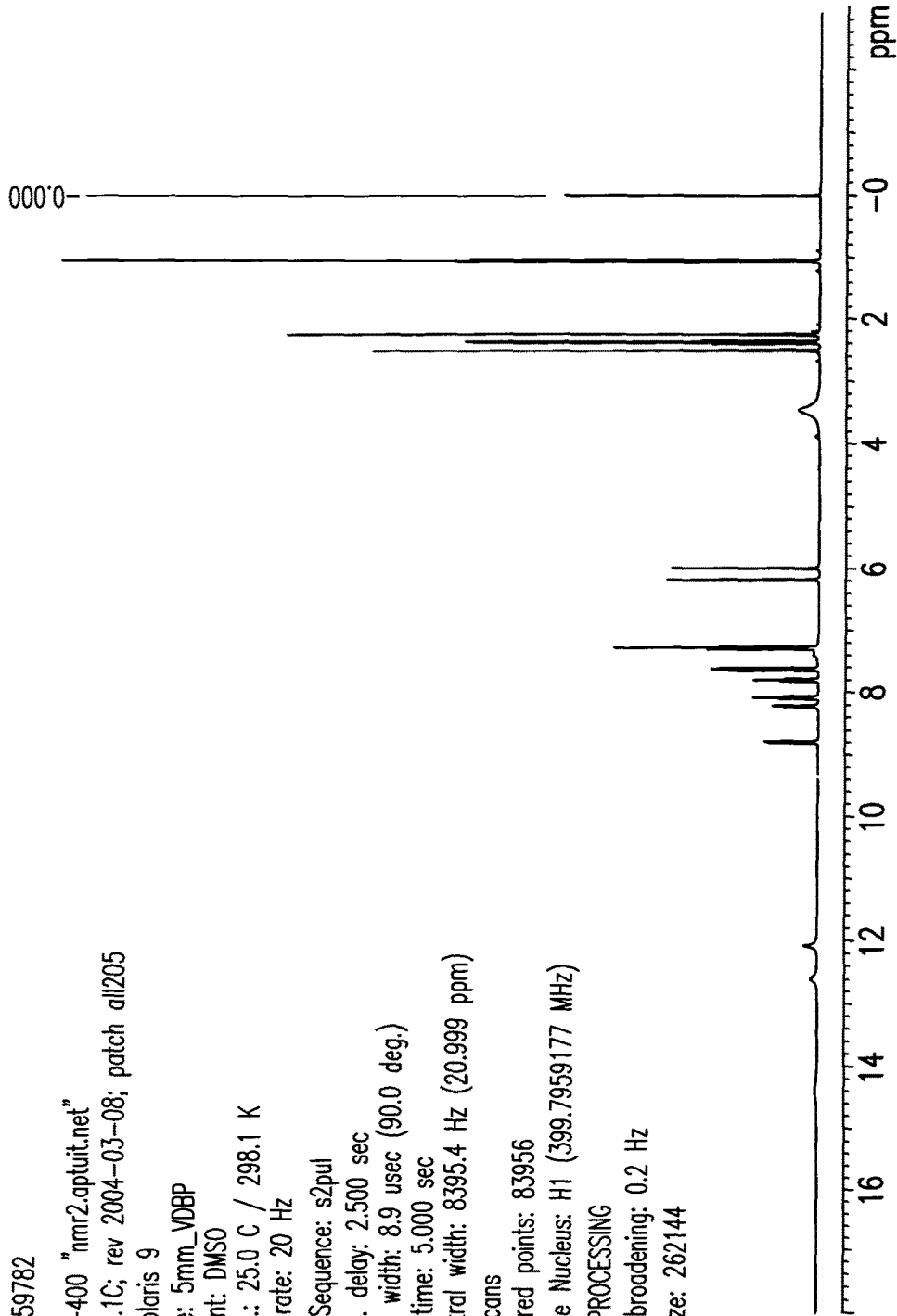

FIG. 27 shows a representative $^1$H NMR spectrum of Form B of the esylate salt of Compound 6.

Figure 28:
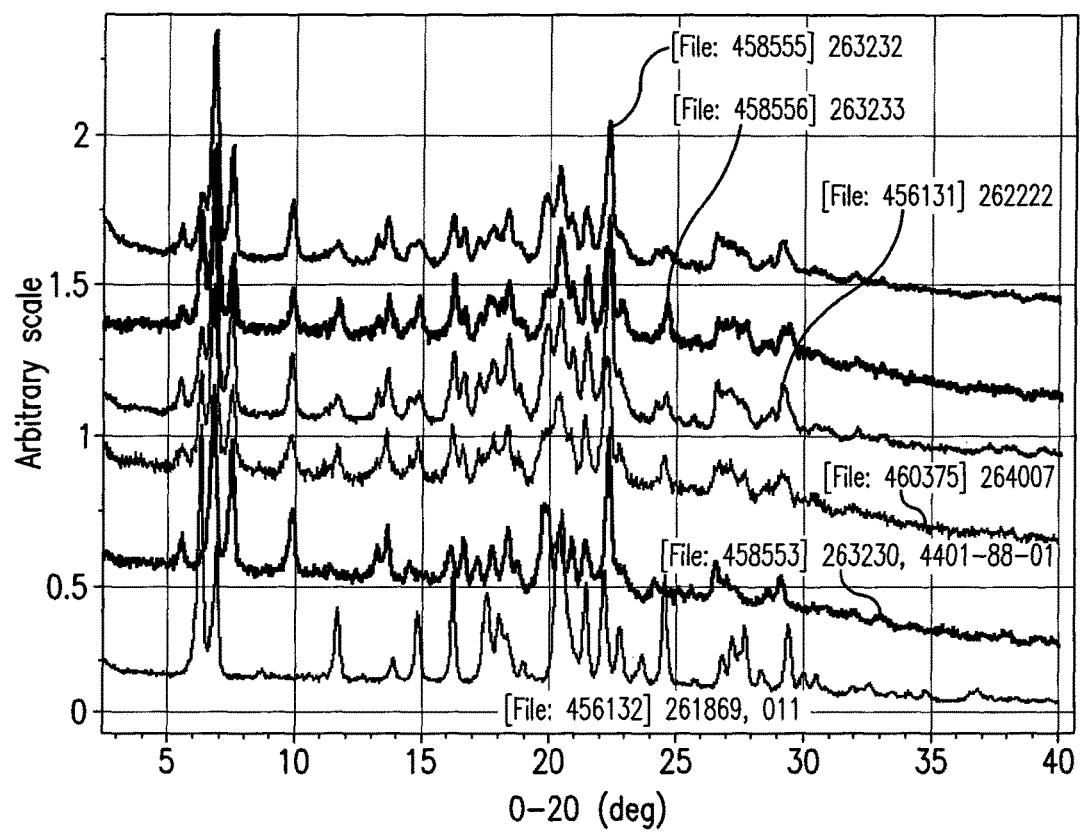

FIG. 28 shows representative XRPD patterns of Form C of the esylate salt of Compound 6 and mixtures of Forms A and C of the esylate salt of Compound 6, all obtained from the polymorph screen described in Tables 7A and 7B.

Figure 29:
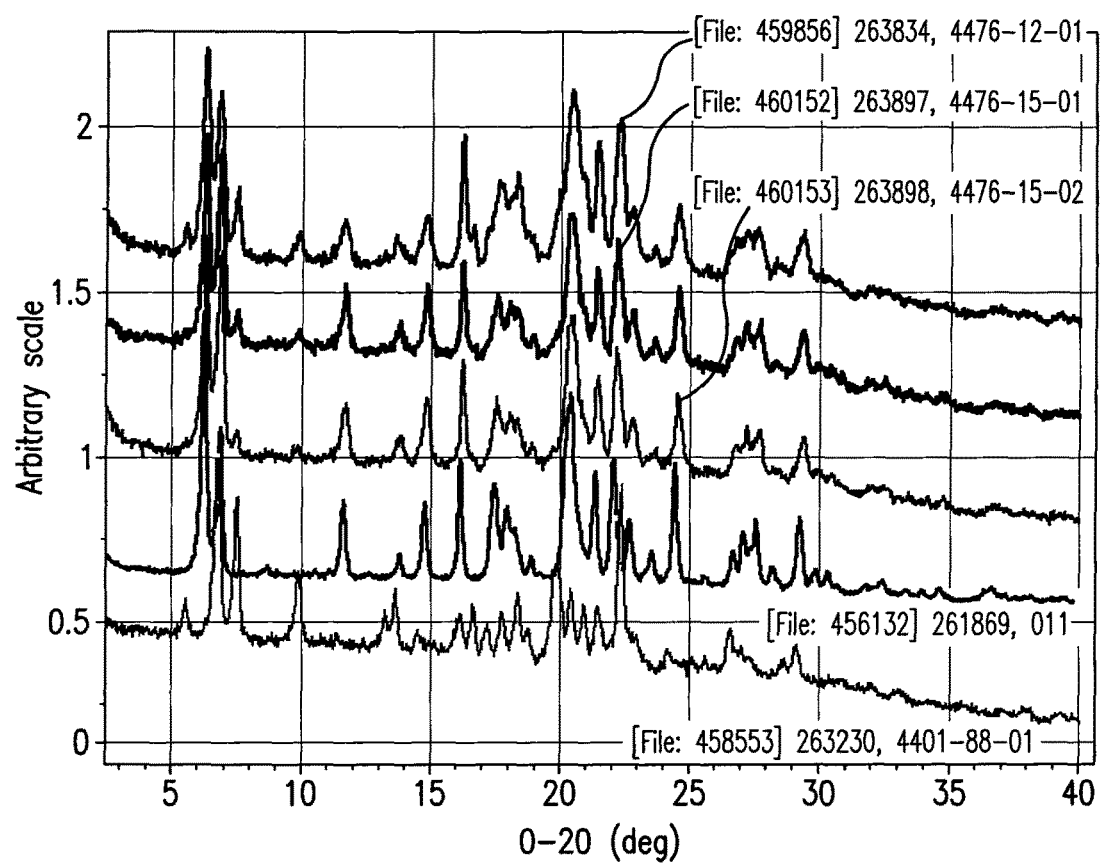

FIG. 29 shows representative XRPD patterns of Form C of the esylate salt of Compound 6 and mixtures of Forms A and C of the esylate salt of Compound 6, obtained from conditions described in Tables 8 and 11.

Figure 30:
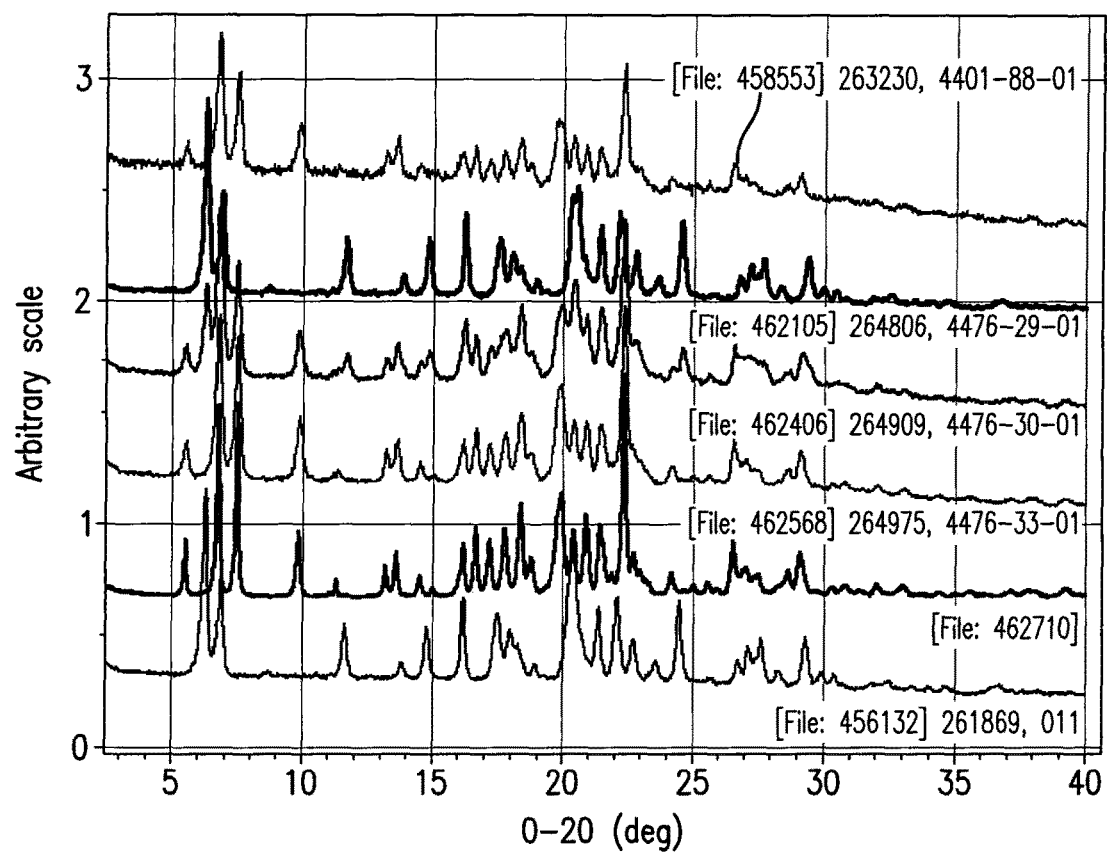

FIG. 30 shows representative XRPD patterns of, from top to bottom (i)-(iii) mixture of Forms C and A of the esylate salt of Compound 6, (iv) Form C of the esylate salt of Compound C and (v) Form A of the esylate salt of Compound 6.

Figure 31:
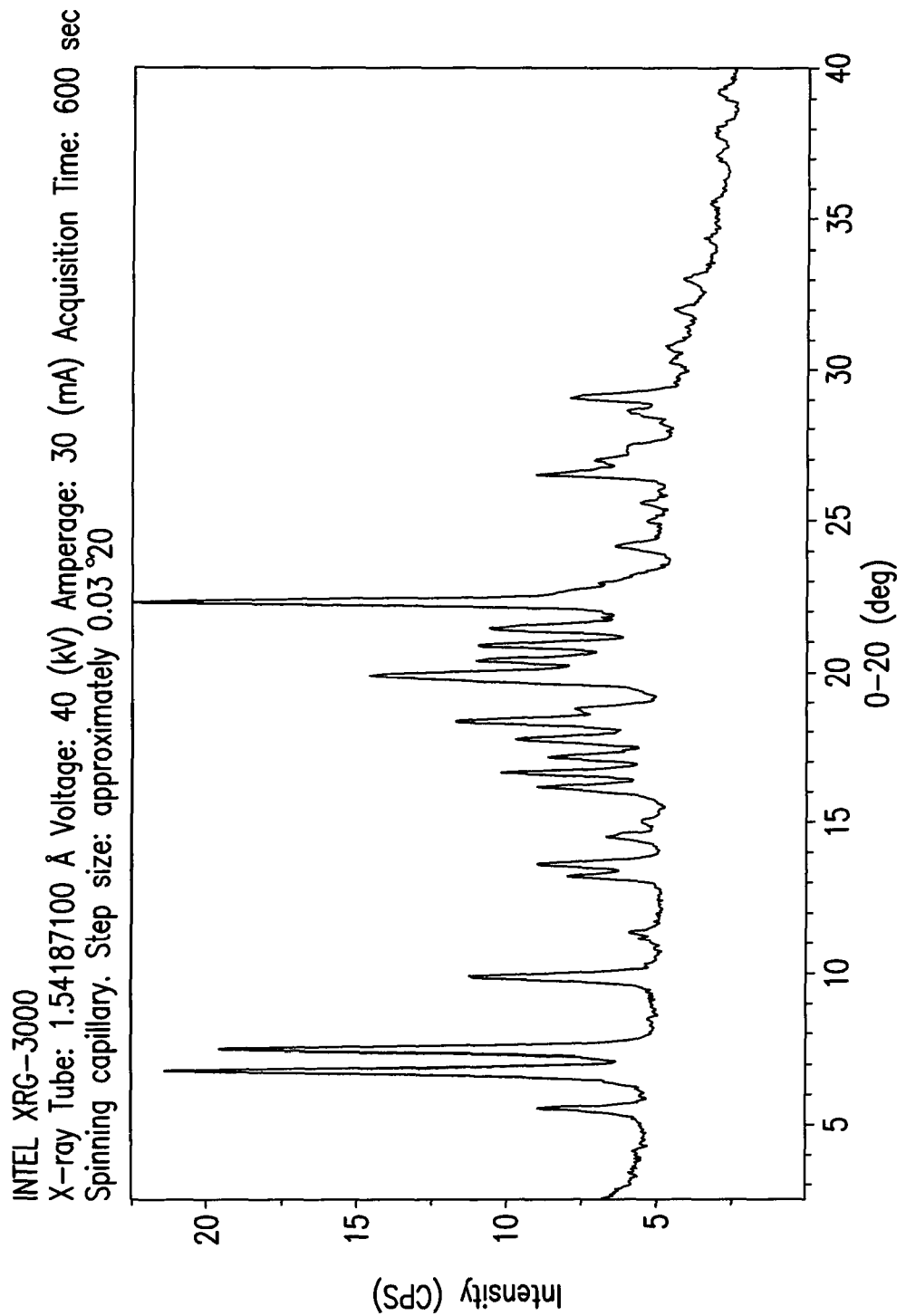

FIG. 31 shows a representative XRPD pattern of Form C of the esylate salt of Compound 6.

Figure 32:
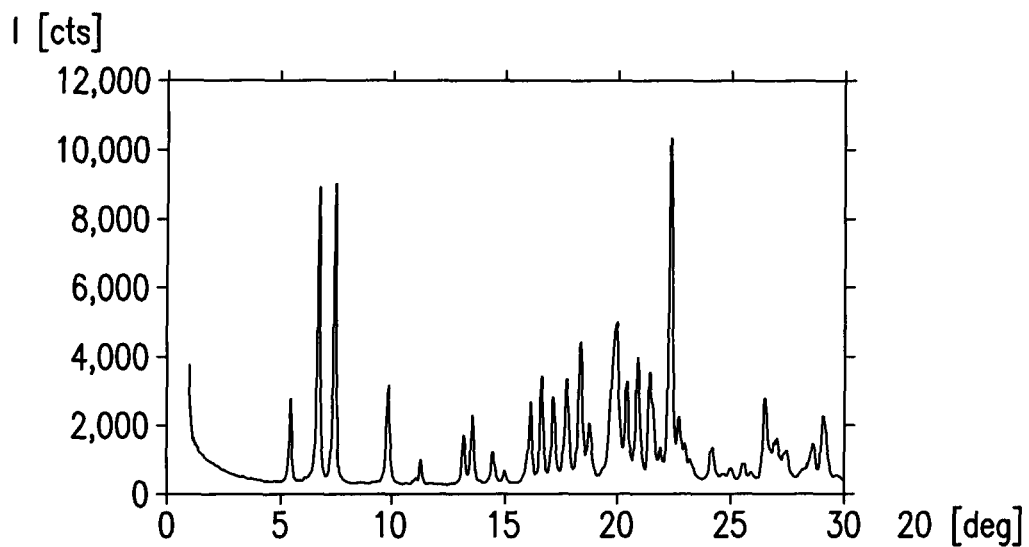

FIG. 32 shows an indexed XRPD pattern of Form C of the esylate salt of Compound 6.

Figure 33:
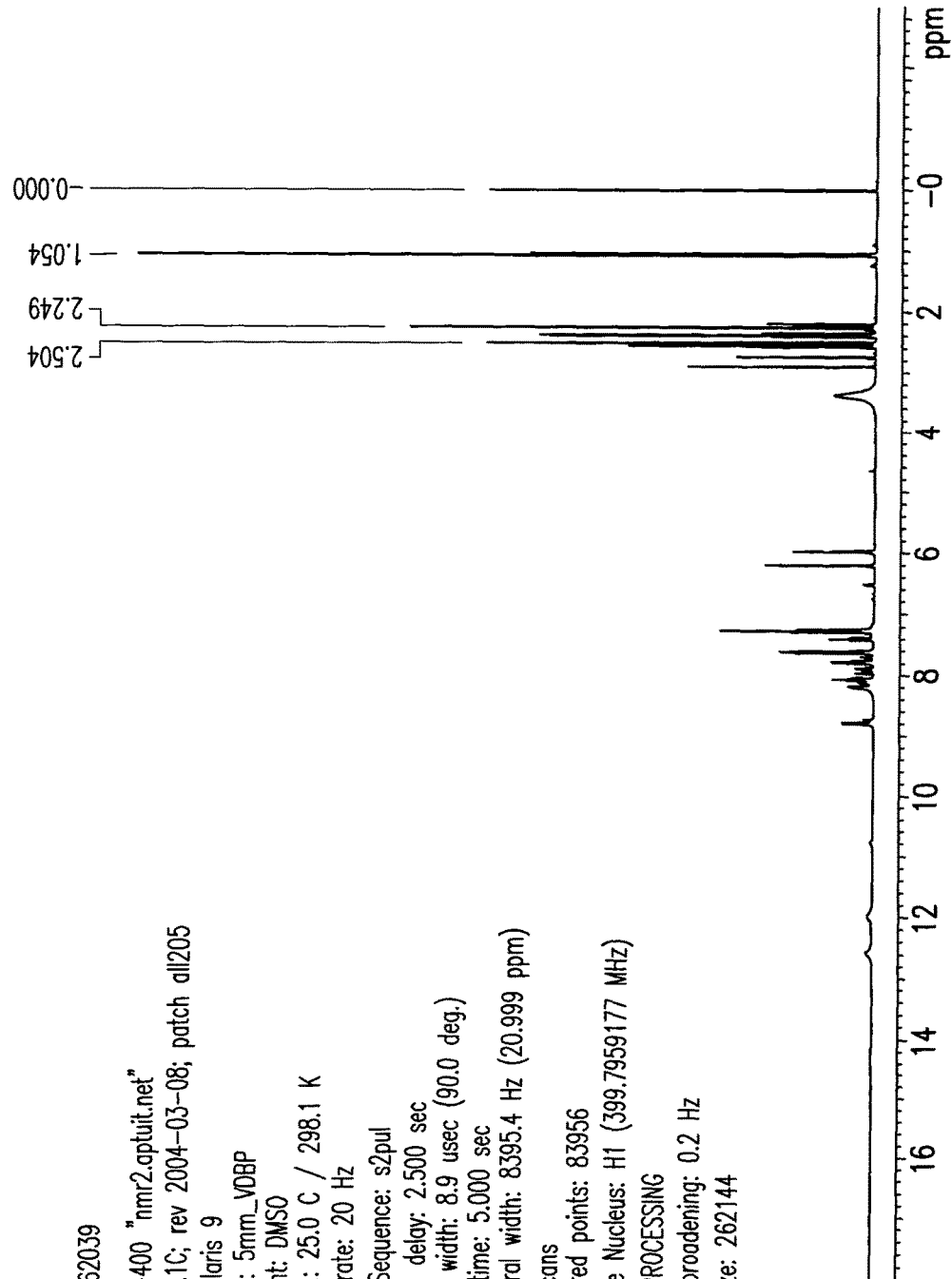

FIG. 33 provides a representative $^1$H NMR spectrum of Form C of the esylate salt of Compound 6.

Figure 34:
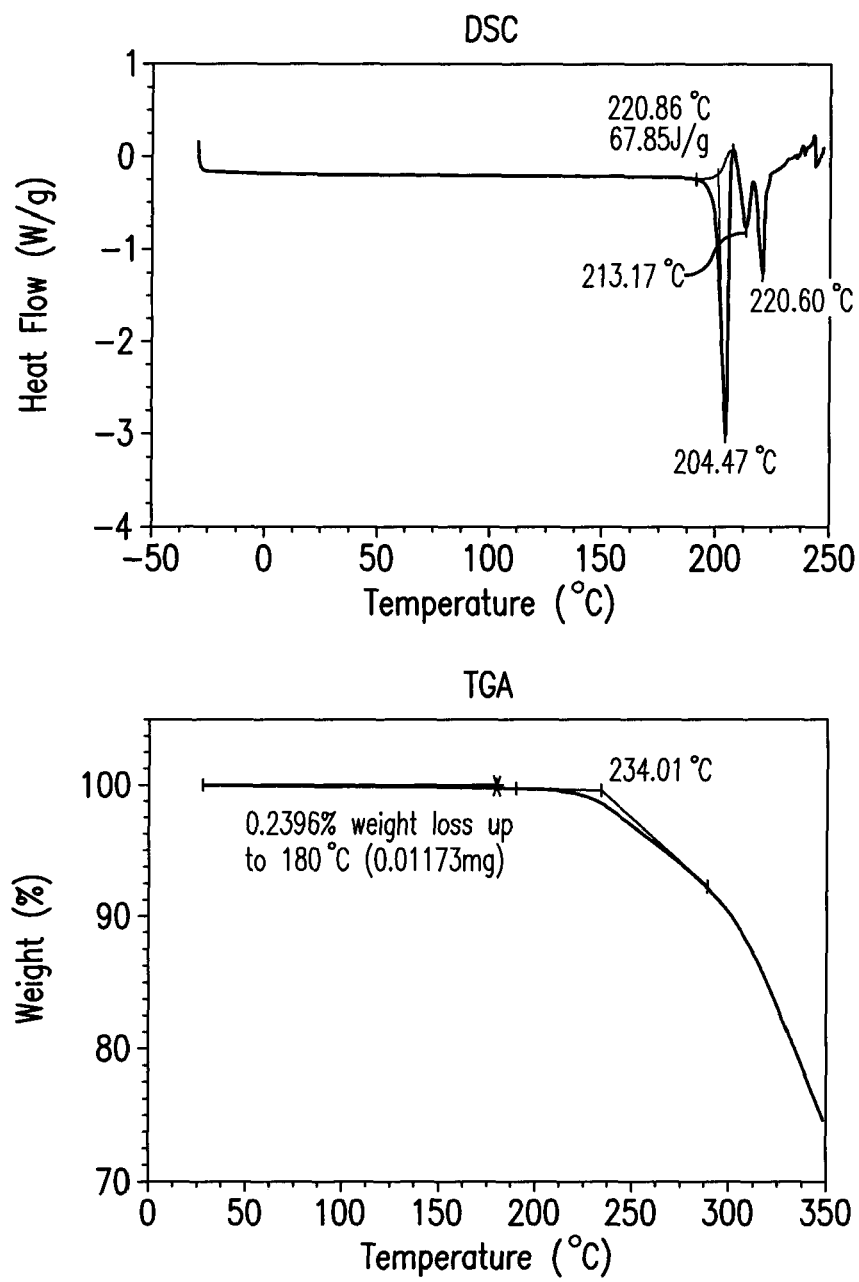

FIG. 34 shows representative DSC (top graph) and TGA (bottom graph) thermograms for Form C of the esylate salt of Compound 6.

Figure 35:
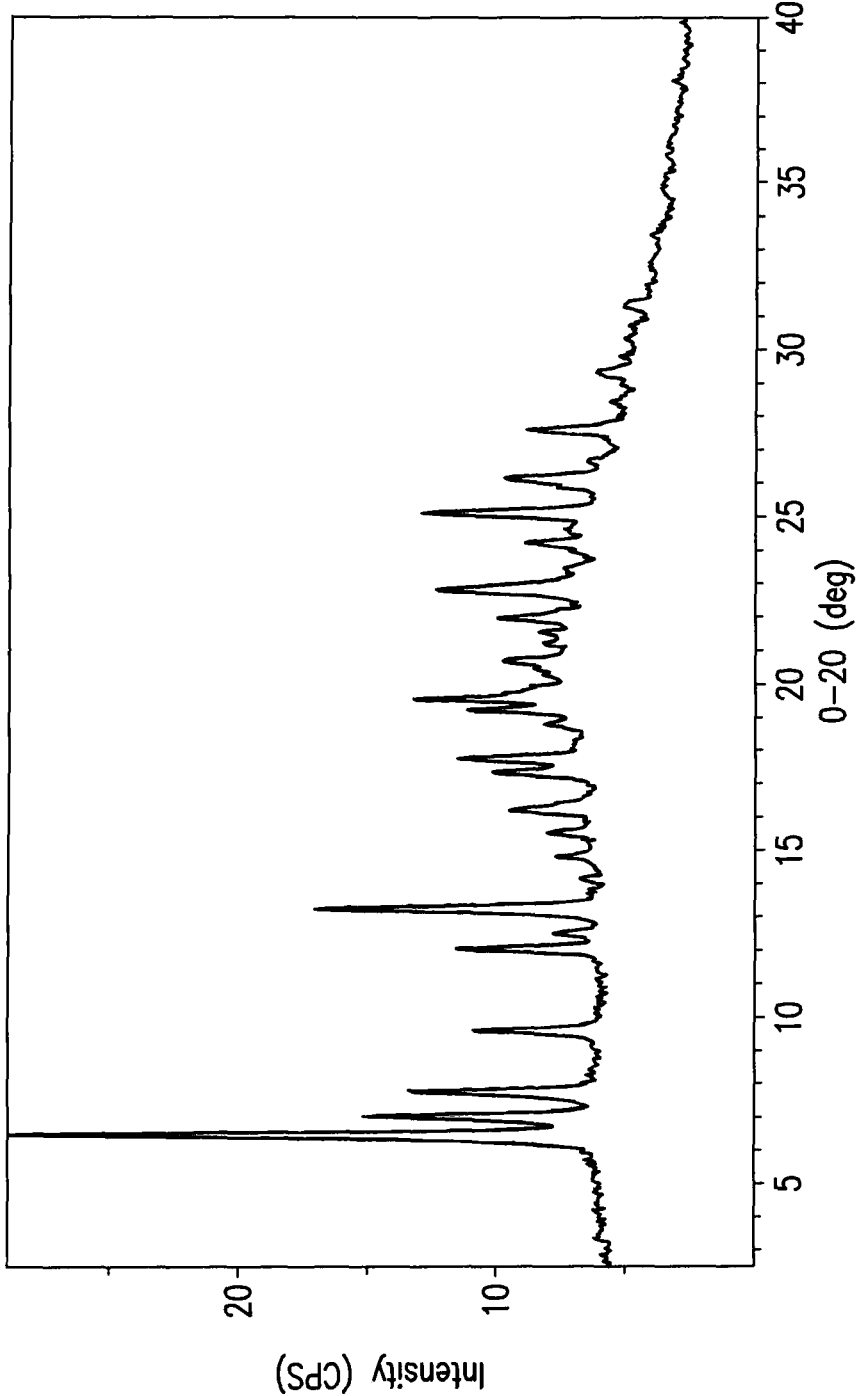

FIG. 35 provides a representative XRPD pattern of Form D of the esylae salt of Compound 6 dissolved in DMSO-d$_6$.

Figure 36:
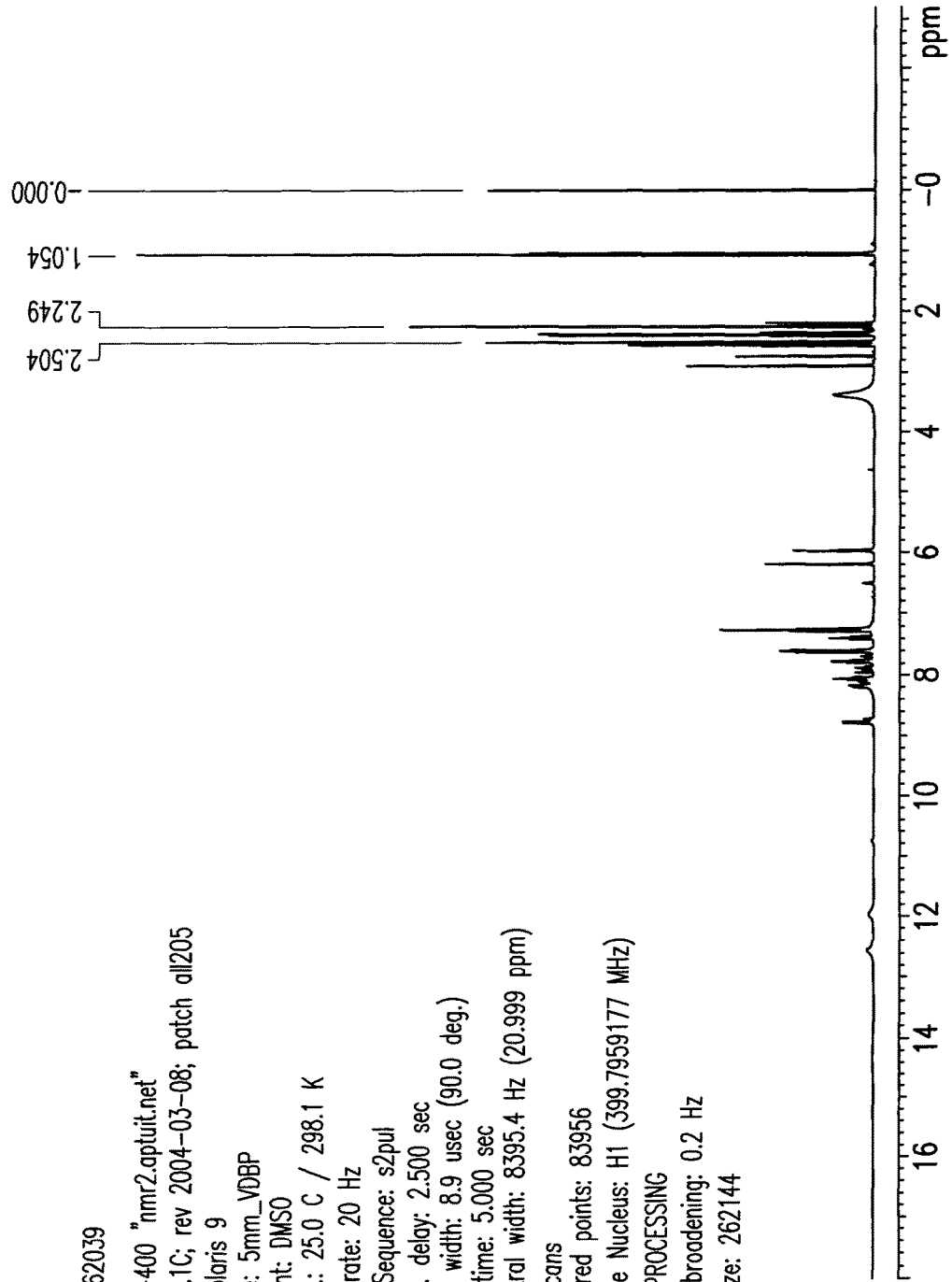

FIG. 36 provides a representative $^1$H NMR spectrum of Form D of the esylate salt of Compound 6.

Figure 37:
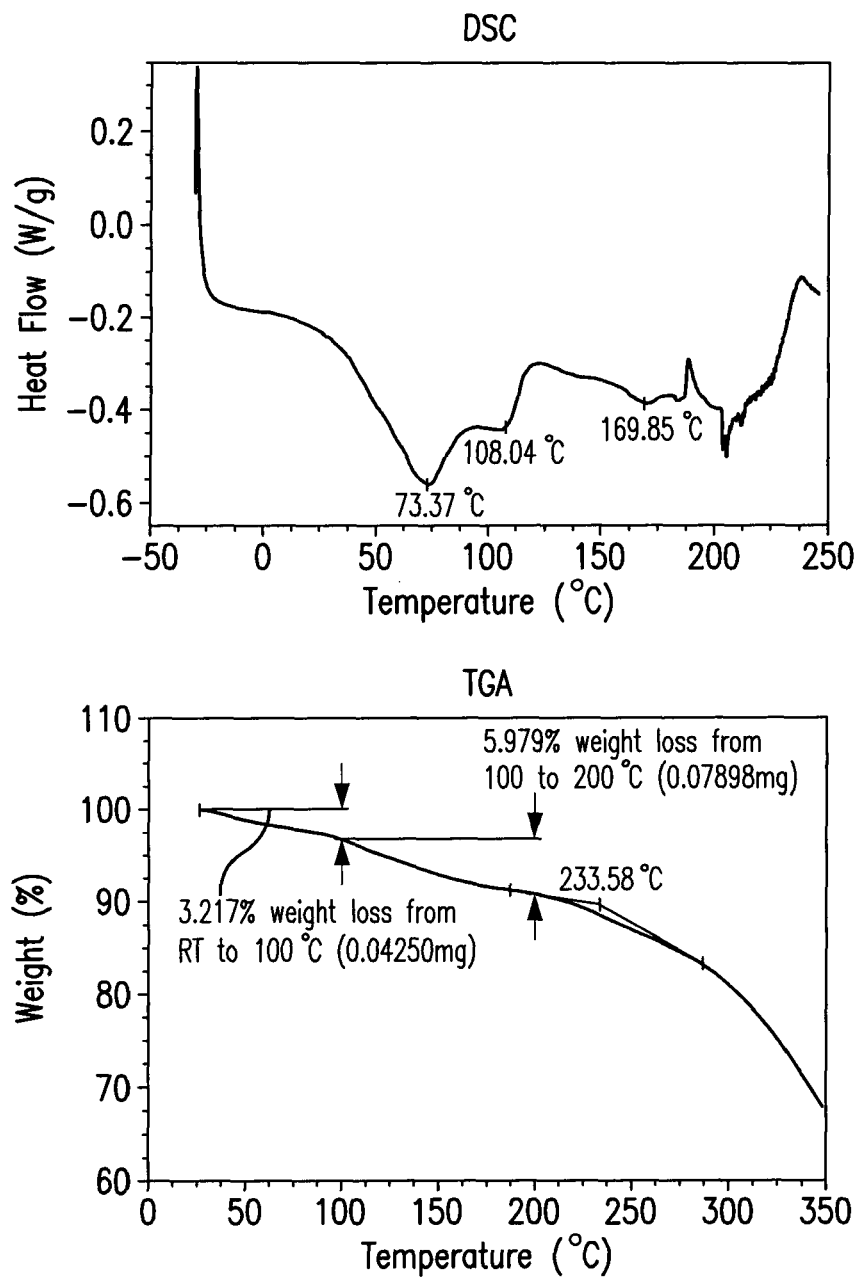

FIG. 37 shows representative DSC (top graph) and TGA (bottom graph) thermograms for Form D of the esylate salt of Compound 6.

Figure 38:
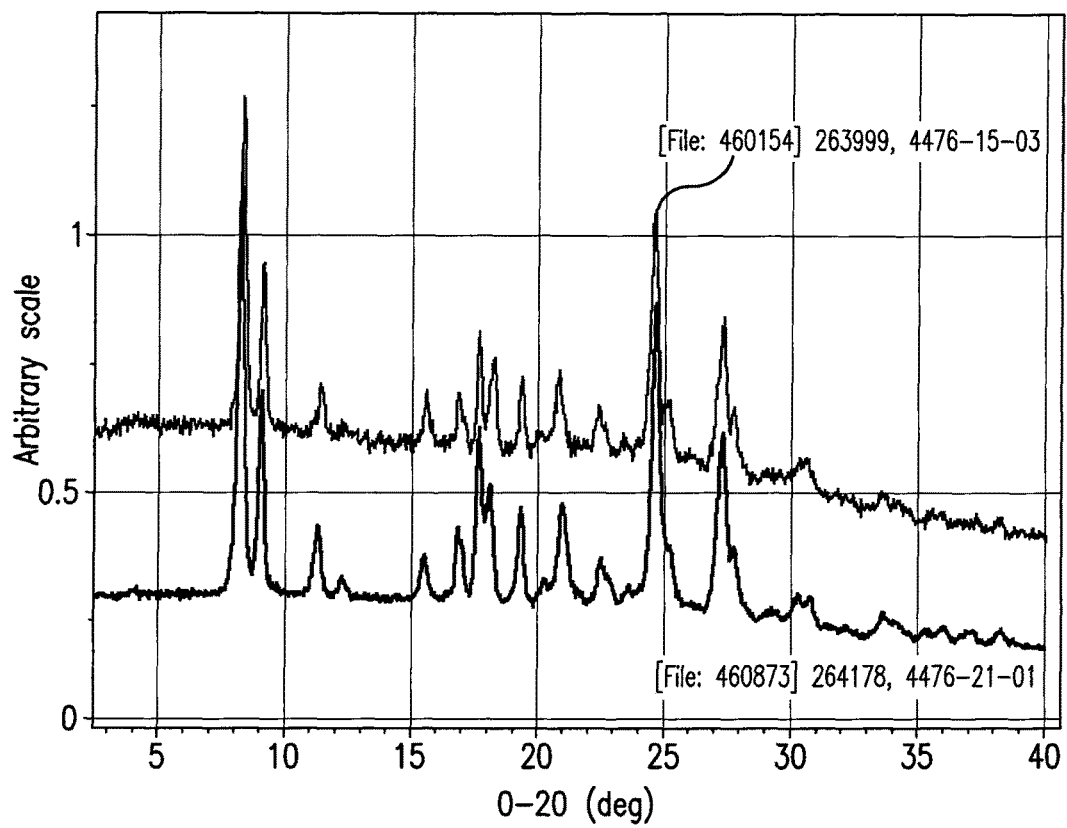

FIG. 38 shows a representative XRPD pattern of Form A of the free base of Compound 6.

Figure 39:
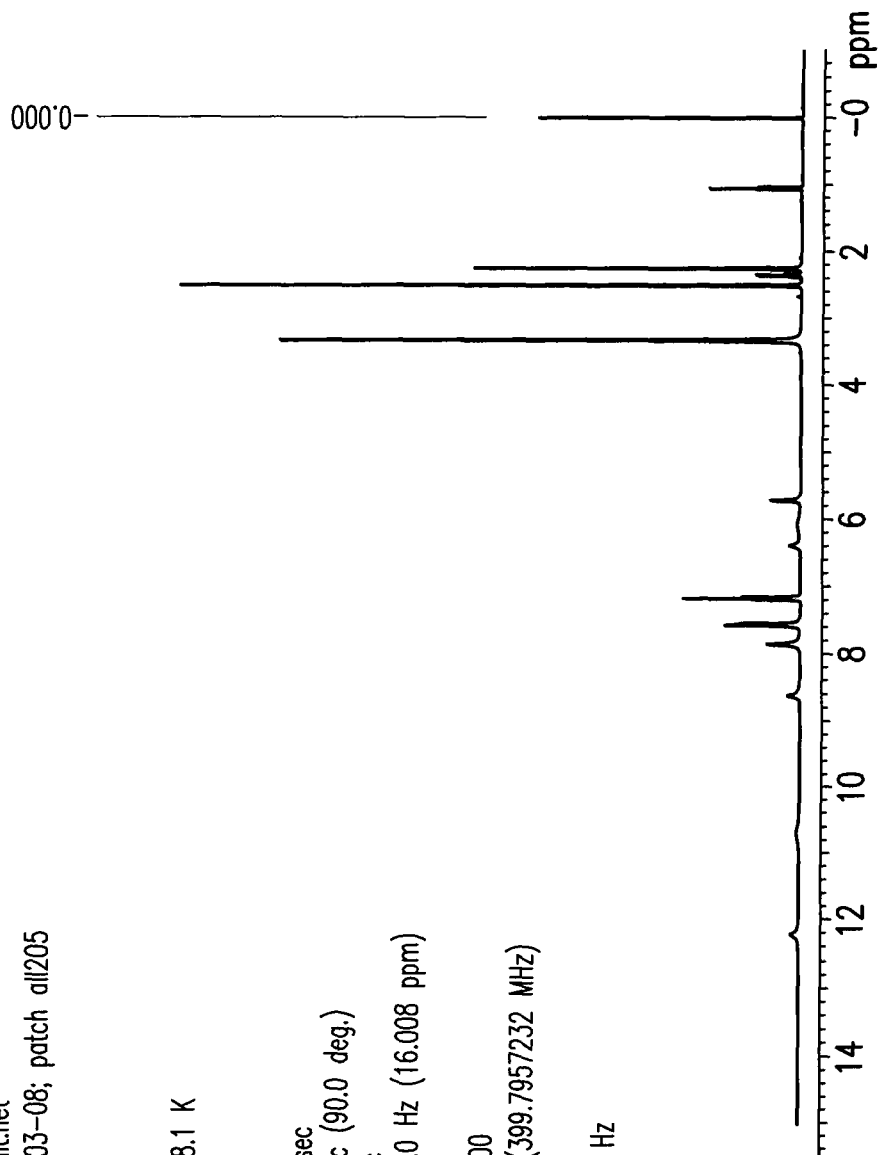

FIG. 39 shows a representative $^1$H NMR spectrum of Form A of the free base of Compound 6 dissolved in DMSO-d.

Figure 40:
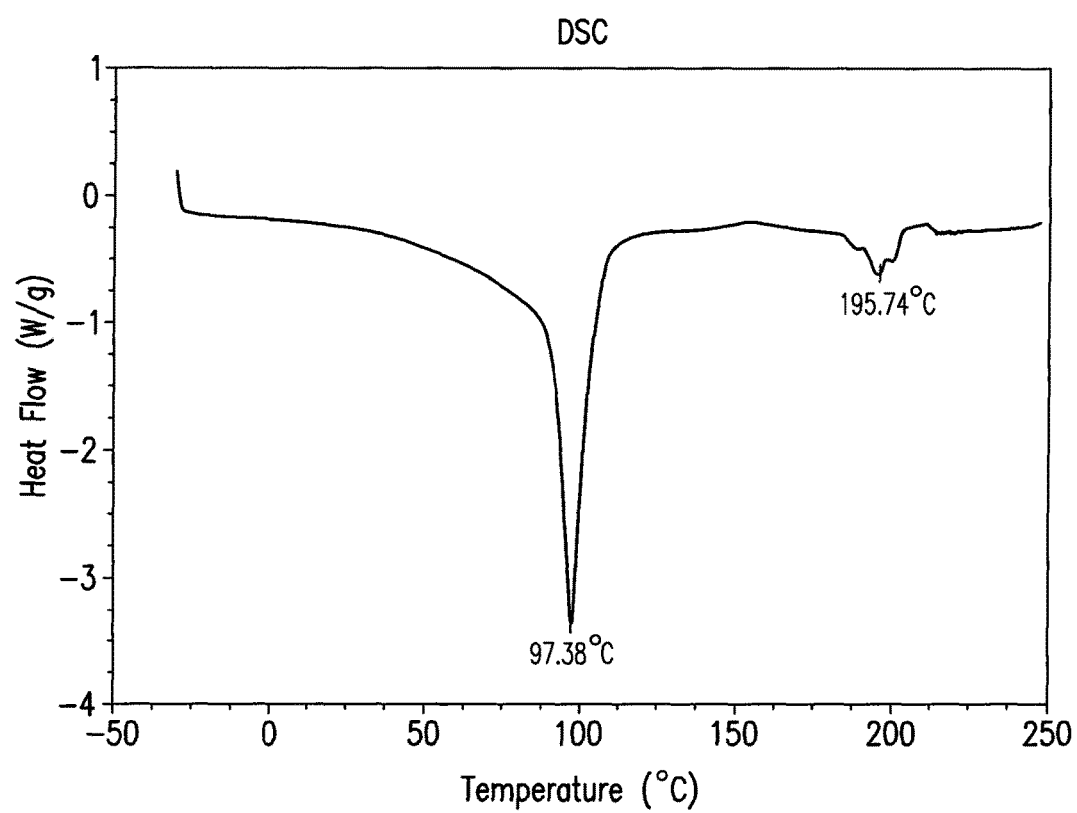

FIG. 40 shows a representative DSC thermogram of Form A of the free base of Compound 6.

Figure 41:

FIG. 41 shows the DSC thermogram for Form A of the esylate salt of Compound 0.

Figure 42:
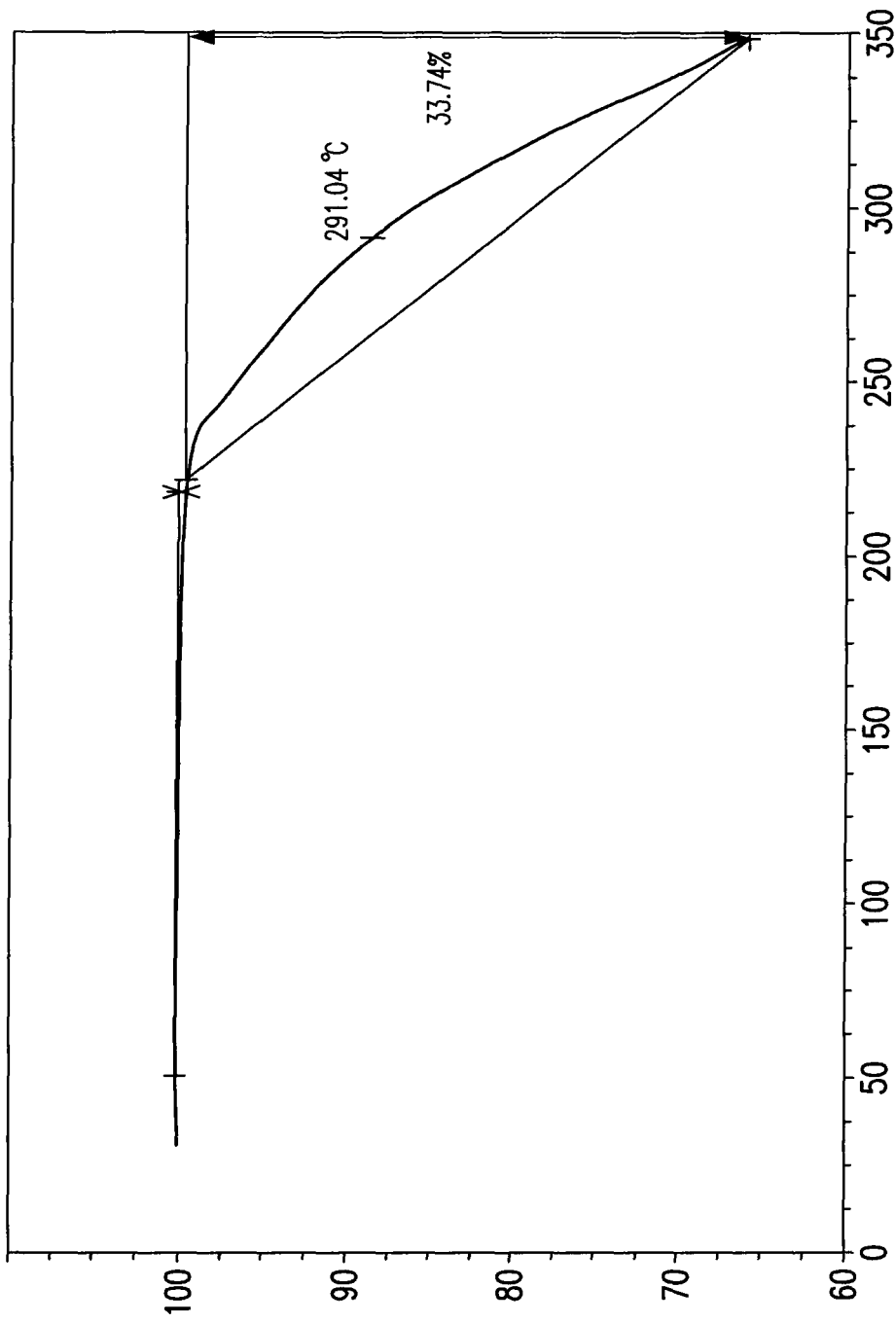

FIG. 42 shows the TGA thermogram for Form A of the esylate salt of Compound 0.

Figure 43:
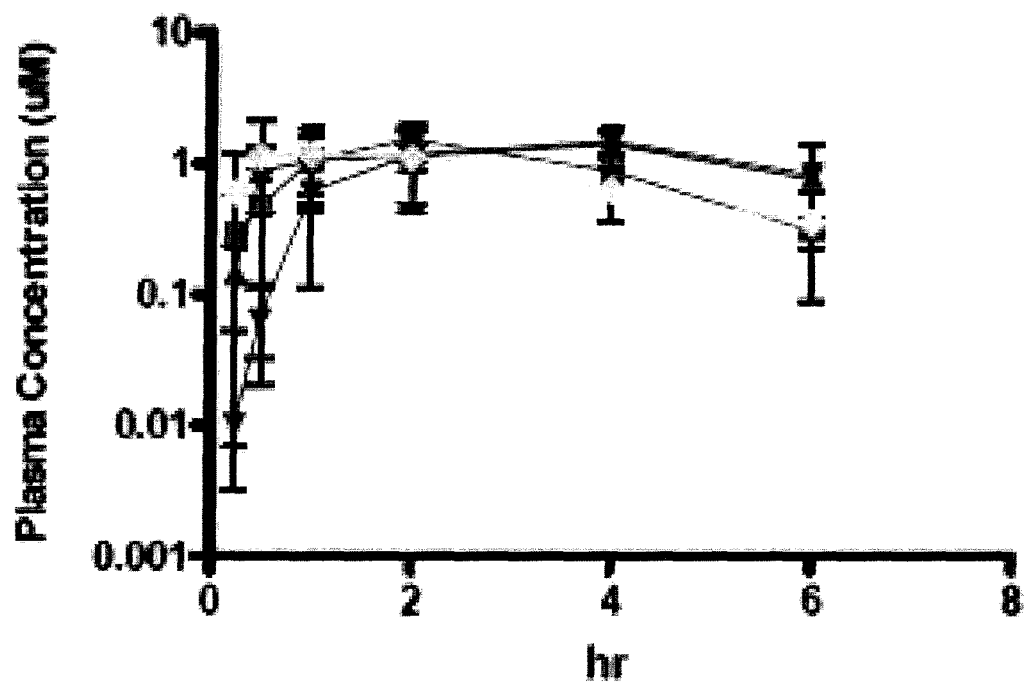

FIG. 43 illustrates plots of plasma concentrations for exemplary salts of Compound 6. In the figure, the plot with solid squares represents administration of 10 mg/kg Compound 6 mesylate capsule neat, the plot with solid upright triangles represents administration of 10 mg/kg Compound 6 esylate capsule neat, the plot with solid inverted triangles represents administration 10 mg/kg Compound 6 HBr capsule neat, the plot with solid inverted triangles represents administration of Compound 6 in (4-fluorophenyl)(4-((5-methyl-1H-pyrazol-3-yl)amino)quinazolin-2-yl)methanol HBr capsule.

6. DETAILED DESCRIPTION

6.1 Definitions

As used herein and unless otherwise specified, the term "Compound 6" means the compound that is chemically named (R)-(4-fluorophenyl)(4-((5-methyl-1H-pyrazol-3-yl) amino)quinazolin-2-yl)methanol, depicted as structure (I) above; additionally, unless otherwise specified, the term "Compound 6" includes ionized forms of the compound depicted as structure (I) above, which have undergone salt formation such that the molecule is protonated at one or more atomic positions. To the extent that there is a discrepancy between a chemical name of a compound and a depicted chemical structure of a compound provided herein, the chemical structure shall control.

In one embodiment, salts described herein include "hydrochloride salts" or "HCl salts" of Compound 6. In one embodiment, salts described herein include "esylate salts" or "ethanesulfonate salts" of Compound 6. An ethanesulfonate salt or esylate salt of Compound 6 is an acid addition salt formed by reacting Compound 6 with ethanesulfonic acid.

As used herein and unless otherwise specified, the term "pharmaceutically acceptable salts" refers to salts prepared from one of the following pharmaceutically acceptable acids: hydrochloric acid; hydrobromic acid; sulfuric acid; methanesulfonic acid; ethanesulfonic acid; ethane-1,2-disulfonic acid; benzenesulfonic acid; p-toluenesulfonic acid; naphthalene-2-sulfonic acid; adipic acid; fumaric acid; glycolic acid; hippuric acid; maleic acid, phosphoric acid; and DL-tartaric acid. Acid addition salts can be obtained, e.g., by contacting the neutral form of Compound 6 with a sufficient amount of the desired acid, e.g., either neat or in a suitable solvent. As used herein and unless otherwise specified, the term "admixing" and related terms, when used in connection with salt synthesis, encompass a wide variety of methods by which one may contact an acid and a base to form a salt. As solids, salts can exist in crystalline or amorphous modifications, or mixtures thereof. Examples of methods for preparing and analyzing such salts are provided, e.g., in *Handbook of Pharmaceutical Salts: Properties, Selection and Use*, P. H. Stahl and C. G. Wermuth, Eds., (2002), Wiley, Weinheim. See also A. T. M. Serajuddin, *Adv. Drug Deliv. Rev.* (2007) 59: 603-16; P. L. Gould, *Int. J. Pharm.* (1986) 33: 201-17.

As used herein and unless otherwise specified, the terms "solid form" and related terms refer to a physical form which is not predominantly in a liquid or a gaseous state. As used herein and unless otherwise specified, the term "solid form" and related terms, when used herein to refer to Compound 6, refer to a physical form comprising Compound 6 which is not predominantly in a liquid or a gaseous state. Solid forms may be crystalline, amorphous or mixtures thereof. In particular embodiments, solid forms may be liquid crystals.

A "single-component" solid form comprising Compound 6 consists essentially of Compound 6. A "multiple-component" solid form comprising Compound 6 comprises a significant quantity of one or more additional species, such as ions and/or molecules, within the solid form. For example, in particular embodiments, a crystalline multiple-component solid form comprising Compound 6 further comprises one or more species non-covalently bonded at regular positions in the crystal lattice.

As used herein and unless otherwise specified, the term "crystalline" and related terms used herein, when used to describe a substance, modification, material, component or product, unless otherwise specified, mean that the substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ ed., 1843-1844 (1995).

As used herein and unless otherwise specified, the term "crystal forms" and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure. Crystal forms of a substance may be obtained by a number of methods, as known in the art.

As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

As used herein and unless otherwise specified, the term "solvate" and "solvated," refer to a crystal form of a substance which contains solvent. The term "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. Amorphous forms of a substance may be obtained by a number of methods, as known in the art.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately."

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of reccurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The term "subject" is defined herein to include animals such as mammals, including, but not limited to, primates (e.g., humans), cows, sheep, goats, horses, dogs, cats, rabbits, rats, mice and the like. In specific embodiments, the subject is a human.

In addition to solid forms comprising Compound 6, provided herein are solid forms comprising prodrugs of Compound 6.

Solid forms provided herein may also comprise unnatural proportions of atomic isotopes at one or more of the atoms in Compound 6. For example, the compound may be radiolabeled with radioactive isotopes, such as for example tritium ($^3$H), iodine-125 ($^{125}$I) sulfur-35 ($^{33}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of Compound 6, whether radioactive or not, are intended to be encompassed within the scope of the embodiments provided herein.

6.2 Solid Forms Comprising Compound 6

Certain embodiments herein provide single-component and multiple-component solid forms comprising Compound 6, which has the chemical structure shown above as structure (I).

Compound 6 can be synthesized or obtained according to any method apparent to those of skill in the art based upon the teachings herein, including the methods described in the Examples below. Compound 6 can also be prepared according to the methods described in U.S. Provisional Patent App. No. 61/379,286, filed Sep. 1, 2010 and U.S. patent application Ser. No. 13/223,099, filed Aug. 31, 2011, the entireties of each of which are incorporated by reference herein. In its free base form, Compound 6 has the chemical structure shown above as structure (I).

Solid forms comprising Compound 6 include single-component and multiple-component forms, including crystal forms and amorphous forms, and including, but not limited to, polymorphs, salts, solvates, hydrates, co-crystals and clathrates. Particular embodiments herein provide single-component amorphous solid forms of the free base of Compound 6. Particular embodiments herein provide single-component crystalline solid forms of the free base of Compound 6. Particular embodiments herein provide multiple-component amorphous forms comprising Compound 6. Particular embodiments herein provide multiple-component crystalline solid forms comprising Compound 6. The multiple-component solid forms comprising Compound 6 may be neutral or ionic complexes, or may comprise both neutral and ionic components together in the solid form. Multiple-component solid forms provided herein include solid forms which may be described by the terms salt, co-crystal, hydrate, solvate, clathrate and/or polymorph, and include solid forms which may be described by one or more of these terms.

Solid forms comprising Compound 6 can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. The particle size of the resulting solid forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, certain solid forms are characterized by physical properties, e.g., stability, solubility and dissolution rate, appropriate for clinical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

In certain embodiments, solid forms comprising Compound 6 may be analyzed by certain parameters that may be obtained, e.g., from single-crystal X-ray diffraction parameters, among other techniques. The following are references and citations for single-crystal XRD data collection: (i) Sheldrick, G. M. *SHELX97, A Program for Crystal Structure Refinement*, University of Gottingen, Germany, 1997; (ii) Otwinowski, Z.; Minor, W. *Methods Enzymol.* 1997, 276, 307; (iii) Bruker, XPREP in SHELXTL v.6.12, Bruker AXS Inc., Madison, Wis., USE, 2002; (iv) Burla, M. C., et al., *J. Appl. Cryst.* 2005, 38, 381; (v) International Tables for Crystallography, Vol. C, Kluwer Academic Publishers: Dordrecht, The Netherlands, 1992, Tables 4.2.6.8 and 6.1.1.4; (vi) PowderCell for Windows v.2.3 Kraus, W.; Nolze, G. Federal Institute for Materials Research and Testing, Berlin Germany, EU, 1999; (vii) Johnson, C. K. ORTEPIII, Report ORNL-6895, Oak Ridge National Laboratory, TN, U.S.A. 1996. ORTEP-3 for Windows v.1.05, Farrugia, L. J., *J. Appl. Cryst.* 1997, 30, 565; (viii) Watkin, D. J.; et al. CAMERON, Chemical Crystallography Laboratory, University of Oxford, Oxford, 1996.

In certain embodiments, solid forms comprising Compound 6 may be characterized by thermal ellipsoid plots. In certain embodiments, solid forms comprising Compound 6 may be represented by molecular packing motifs.

Certain embodiments herein provide compositions comprising one or more of the solid forms. Certain embodiments provide compositions of one or more solid forms in combination with other active ingredients. Certain embodiments provide methods of using these compositions in the treatment, prevention or management of diseases and disorders including, but not limited to, the diseases and disorders provided herein.

6.2.1 Form A of the Esylate Salt of Compound 6

Certain embodiments herein provide the Form A crystal form of the esylate salt of Compound 6. In certain embodiments, Form A of the esylate salt of Compound 6 can be obtained by reacting Compound 6 with ethanesulfonic acid. In certain embodiments, Form A can be obtained by reacting Compound 6 with ethanesulfonic acid in various solvent systems, including, but not limited to, solvent systems comprising a protic solvent (e.g., methanol) an aprotic solvent (e.g., acetonitrile, a hydrocarbon (e.g., toluene) or a mixture of solvents (e.g., methanol and DCM or methanol and chloroform). In certain embodiments, the Form A crystal form of the esylate salt of Compound 6 can be prepared by crystallization from solvent, water or solvent/water mixtures including, but not limited to, methanol, ethanol, isopropanol, 1-propanol, hexafluoroisopropanol, water, ethyl acetate, acetone, acetonitrile, dichloromethane, chloroform, isopropylether, tetrahydrofuran, methyl ethyl ketone, and mixtures of two or more solvents thereof. In certain embodiments, the Form A crystal form of the esylate salt of Compound 6 can be prepared by crystallization from a variety of solvent systems, including, but not limited to, solvent systems comprising methanol, 1:1 methanol/chloroform mixture, 1:4 methanol/toluene mixture, 1:2 methanol/acetone mixture, ethanol, 1:1 ethanol/water mixture, 1-propanol, isopropanol, 12 hexafluoroisopropanol/acetone mixture, 1:2 hexafluoroisopropanol/isopropyl ether mixture, 1:2 hexafluoroisopropanol/tetrahydrofuran mixture, acetonitrile, dioxane, 1:1 2,2,2,-trifluoroethanol/acetonitrile mixture, 1:1 2,2,2,-trifluoroethanol/ethyl acetate mixture, 1:1 2,2,2,-trifluoroethanol/isopropanol mixture, 1:1 2,2,2,-trifluoroethanol/methyl ethyl ketone mixture and mixtures of two or more thereof. In certain embodiments, Form A of the esylate salt of Compound 6 can be obtained by crystallization from solvent, water or solvent/water mixtures including, but not limited to, common laboratory organic solvents.

For example, in one embodiment, Form A of the esylate salt of Compound 6 is obtained by precipitation from a solution comprising methanol or ethanol. For example, in one embodiment, Form A of the esylate salt of Compound 6 is obtained by precipitation from a solution comprising acetonitrile. In another embodiment, Form A of the esylate salt of Compound 6 is prepared by precipitation via evaporation and/or cooling from a solution comprising methanol or ethanol. In another embodiment, Form A of the esylate salt of Compound 6 is obtained by slurry in a solvent system comprising methanol, ethanol, isopropanol or 1-propanol. In certain embodiments, Form A of the esylate salt of Compound 6 can be obtained by crystallization from solvent, water or solvent/water mixtures including, but not limited to, common laboratory organic solvents. In certain embodiments, Form A of the esylate salt of Compound 6 is obtained by crystallization methods including, but not limited to, precipitation, slurry at ambient temperature, slurry at elevated temperature, slurry at sub-ambient temperature, evaporation, slow evaporation, fast evaporation and/or concentration. In certain embodiments, Form A of the esylate salt of Compound 6 is obtained by vapor diffusion using a solvent system comprising methanol or ethanol.

In certain embodiments, Form A of the esylate salt of Compound 6 is obtained by a process comprising the steps of: (1) contacting esylate salt of Compound 6 with a solvent; and (2) isolating Form A of the esylate salt of Compound 6. [Please verify]. In certain embodiments, Form A of the esylate salt of Compound 6 is purified via solvent-based purification methods, including solvent slurry. In particular embodiments, purification via solvent slurry reduces or removes one or more chemical impurities and/or physical impurities (e.g., one or more other crystal forms and/or amorphous forms).

In certain embodiments, Form A of the esylate salt of Compound 6 is obtained by a process comprising the steps of: (1) dissolving Form A of the esylate salt of Compound 6; and (2) recrystallizing Form A of the esylate salt of Compound 6. In certain embodiments, Form A of the esylate salt of Compound 6 is purified via recrystallization. In particular embodiments, such purification via recrystallization reduces or removes one or more chemical impurities, isomeric impurities and/or physical impurities (e.g., one or more other crystal forms and/or amorphous forms).

In certain embodiments, Form A of the esylate salt of Compound 6 is substantially pure. In certain embodiments, Form A of the esylate salt of Compound 6 is substantially free of chemical impurities. In certain embodiments, Form A of the esylate salt of Compound 6 is substantially free of isomeric impurities. In certain embodiments, Form A of the esylate salt of Compound 6 is substantially free of physical impurities, e.g., one or more other crystal forms and/or amorphous forms. In certain embodiments, Form A of the esylate salt of Compound 6 is substantially free of the free base of Compound 6. In certain embodiments, Form B of the Form A of the esylate salt of Compound 6 is substantially free of other crystal forms comprising Compound 6.

Figure 16:
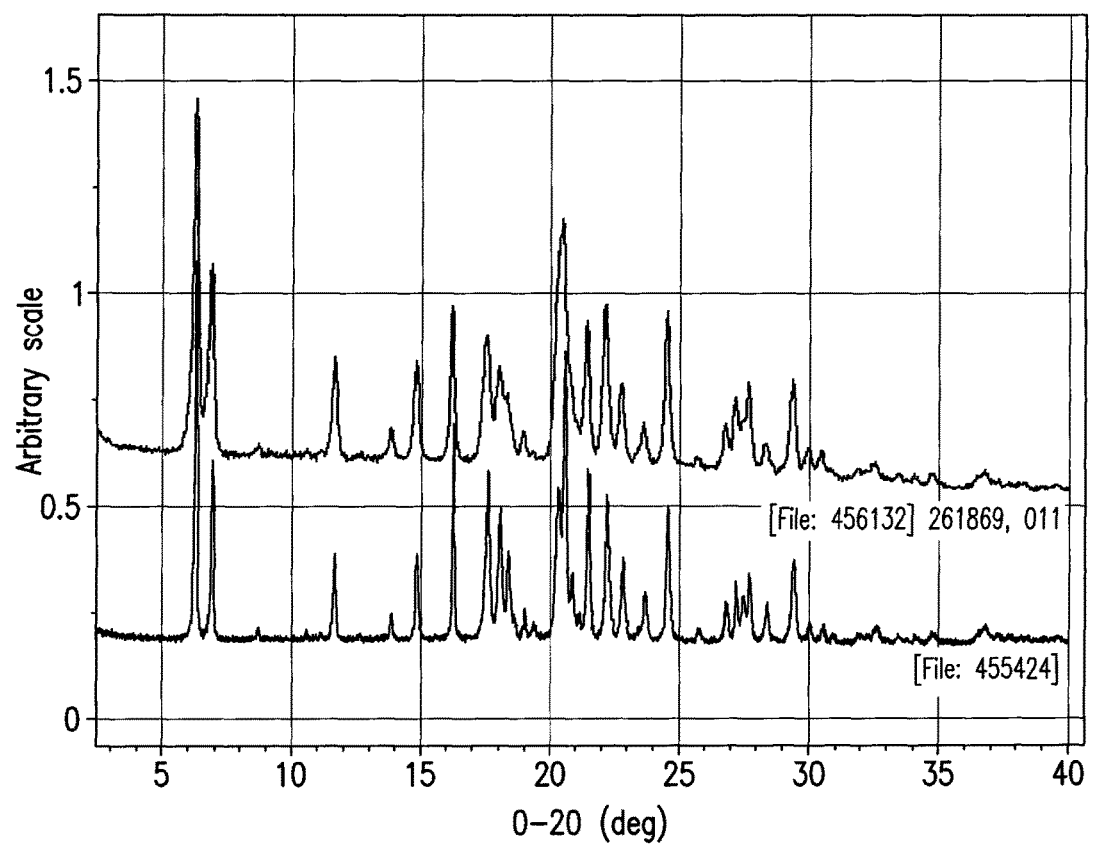
FIG. 16 shows representative XRPD patterns of Form A of the esylate salt of Compound 6. The top pattern is a representative XRPD pattern obtained from the INEL XRG-3000 diffractometer and the bottom pattern is a representative XRPD pattern obtained from the PANalytical X'Pert PRO diffractometer.
Figure 17:
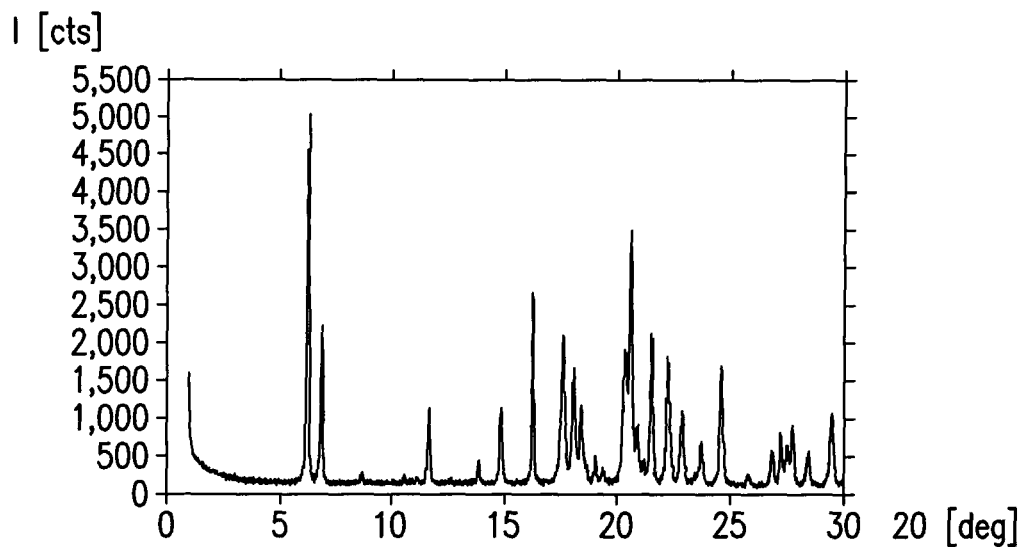
FIG. 17 shows an indexed XRPD patter of Form A of the esylate salt of Compound 6.

A representative XRPD pattern of Form A of the esylate salt of Compound 6 is provided in FIG. 16 and FIG. 17. In certain embodiments, Form A of the esylate salt of Compound 6 is characterized by XRPD peaks located at one, two, three, four, five, six, seven, eight, nine, ten, eleven, twelve or more of the following approximate positions: 6.29, 6.90, 8.68, 10.54, 11.65, 12.64, 13.84, 14.83, 16.24, 17.58, 18.03, 18.38, 19.00, 19.34, 20.31, 20.55, 20.87, 21.13, 21.49, 22.19, 22.81, 23.67, 24.56, 25.80, 26.79, 27.16 27.44, 27.69, 28.36, 29.40 degrees 2θ.

In certain embodiments, Form A of the esylate salt of Compound 6 is characterized by XRPD peaks located at one, two, three, four, five, six, seven, eight, nine, ten, eleven or twelve of the following approximate positions: 6.29, 6.90, 11.65, 14.83, 16.24, 17.58, 18.03, 18.38, 20.31, 20.55, 21.49, 22.19 degrees 2θ. In certain embodiments, Form A of the esylate salt of Compound 6 is characterized by XRPD peaks located at one or both of the following approximate positions: 6.29 and 20.55 degrees 2θ.

In certain embodiments, Form A of the esylate salt of Compound 6 is characterized by an XRPD pattern which matches the pattern exhibited in FIG. 16.

In certain embodiments, Form A of the esylate salt of Compound 6 is characterized by a DSC thermogram comprising an endotherm with an onset temperature of about 218° C. In certain embodiments, Form A of the esylate salt of Compound 6 is characterized by a melting point of about 220° C. In certain embodiments, Form A of the esylate salt of Compound 6 is characterized by a melting point of about 223° C. In certain embodiments, the mass loss upon heating Form A of the esylate salt of Compound 6 from ambient temperature to about 210° C. is about 1% or less, about 0.5% or less, about 0.1% or less, about 0.05% or less, or about 0.03% or less of the total mass of the sample. In certain embodiments, the aforementioned mass loss comprises a loss of solvent, such as, e.g., a loss of water. In certain embodiments, the Form A of the esylate salt of Compound 6 material decomposes above about 210° C. In certain embodiments, samples of Form A of the esylate salt of Compound 6 comprise solvent, e.g. water and/or alcohol. In certain embodiments, samples of Form A of the esylate salt of Compound 6 are substantially free solvent, e.g., water and/or alcohol. Thus, in certain embodiments Form A of the esylate salt of Compound 6 is unsolvated, and in certain embodiments Form A of the esylate salt of Compound 6 is anhydrous.

In certain embodiments, the chemical profile of a sample of Form A of the esylate salt of Compound 6 can be characterized by solution NMR analysis. A representative $^1$H NMR spectrum of a sample of Form A of the esylate salt of Compound 6 dissolved in DMSO-d6 is provided as FIG. 15.

6.2.1 Form B of the Esylate Salt of Compound 6

Certain embodiments herein provide Form B crystal form of the esylate salt of Compound 6. In certain embodiments, Form B of the esylate salt of Compound 6 can be prepared by slow evaporation of Form A of the esylate salt of Compound 6 in 2,2,2-trifulorethanol (TFE). In certain embodiments, Form B of the esylate salt of Compound 6 can be prepared by stressing amorphous esylate salt of Compound 6 at 75% relative humidity (RH) at room temperature for 7 days.

A representative XRPD pattern of Form B of the esylate salt is shown in FIG. 24. In certain embodiments, Form B of the esylate salt of Compound 6 is characterized by XRPD peaks located at one, two, three, four, five, six, seven, eight, nine, ten, eleven or twelve or more of the following approximate positions: 6.17, 7.06, 8.70, 10.15, 10.73, 11.74, 12.37, 14.14, 15.66, 16.82, 17.17, 17.44, 17.92, 18.25, 18.42, 18.61, 18.96, 19.67, 19.99, 20.56, 20.93, 21.30, 21.60, 21.90, 22.40, 22.63, 23.03, 23.64, 23.89, 24.32, 24.49, 25.06, 25.84, 26.31, 26.59, 27.24, 27.50, 27.75, 28.65 and 29.13 degrees 2θ. In certain embodiments, Form B of the esylate salt of Compound 6 is characterized by XRPD peaks located at one, two, three, four, five, six, seven or eight of the following approximate positions: 6.17, 7.06, 12.37, 14.14, 16.82, 20.56, 22.40 and 22.63 degrees 2θ. In certain embodiments, Form B of the esylate salt of Compound 6 is characterized by XRPD peaks located at one or both of the following approximate positions: 6.17 and 16.82 degrees 2θ.

Representative thermal characteristics for Form B of the esylate salt of Compound 6 are shown in FIG. 26. A representative thermogram shown at the top of FIG. 26, comprises thermal events with maxima at approximately 98, 136, 217, 222 and 236° C. In certain embodiments, Form B is characterized by a DSC thermogram comprising one or more thermal events with the following approximate temperature maxima: 98, 136, 217, 222 and 236° C. A representative TGA thermogram, shown at the bottom of FIG. 26, comprises a mass loss of about 4.0% of the total mass of the sample heating from ambient temperature to about 150° C. In certain embodiments, the aforementioned mass loss comprises a loss of solvent, such as, e.g., a loss of TFE, water or mixtures of two or more thereof.

In certain embodiments, Form B of the esylate salt of Compound 6 is a solvate, such as, e.g., a hydrate or solvate or mixed hydrate/solvate. In certain embodiments, Form B comprises approximately 0.3, 0.4, 0.5, 0.6, 0.7 or 0.8 molar equivalents of solvent, such as, e.g., water or TFE, per mole of esylate salt of Compound 6.

In certain embodiments, the chemical profile of a sample of Form B of the esylate salt of Compound 6 can be characterized by solution NMR analysis. A representative $^1$H NMR spectrum of a sample of Form B of the esylate salt of Compound 6 dissolved in DMSO-$d_6$ is provided as FIG. 27.

6.2.2 Form C of the Esylate Salt of Compound 6

In certain embodiments, provided herein is Form C crystal form of the esylate salt of Compound 6. In certain embodiments, Form C of the esylate salt of Compound 6 can be obtained by precipitation from a solution comprising the esylate salt of Compound 6 in ethanol or 1-propanol solutions with isopropyl ether.

A representative XRPD pattern of Form C of the esylate salt of Compound 6 is shown in FIG. 31. In certain embodiments, Form C of the esylate salt of Compound 6 is characterized by XRPD peaks located at one, two, three, four, five, six, seven, eight, nine, ten, eleven or twelve or more of the following approximate positions: 5.52, 6.77, 7.48, 9.85, 11.29, 13.17, 13.58, 14.49, 15.00, 16.17, 16.63, 17.17, 17.75, 18.37, 18.76, 19.96, 20.43, 20.91, 21.41, 21.88, 22.35, 22.73, 22.98, 24.17, 24.64, 25.02, 25.57, 25.92, 26.53, 27.04, 27.45, 28.62, and 29.07 degrees 2θ. In certain embodiments, Form C of the esylate salt of Compound 6 is characterized by XRPD peaks located at one, two, three, four, five, six, seven, eight, nine, ten, eleven or twelve or more of the following approximate positions: 5.52, 6.77, 7.48, 9.85, 13.17, 13.58, 14.49, 16.63, 17.17, 17.75, 18.37, 18.76, 19.96, 20.43, 20.91, 21.41 and 22.35 degrees 2θ. In certain embodiments, Form C of the esylate salt of Compound 6 is characterized by XRPD peaks located at one, two or three of the following approximate positions: 6.77, 7.48 and 22.35 degrees 2θ.

Representative thermal characteristics for Form C of the esylate salt of Compound 6 are shown in FIG. 34. A representative thermogram shown at the top of FIG. 34, comprises thermal events with maxima at approximately 204, 213 and 221° C. In certain embodiments, Form C is characterized by a DSC thermogram comprising one or more thermal events with the following approximate temperature maxima: 204, 213 and 221° C. A representative TGA thermogram, shown at the bottom of FIG. 34, comprises a mass loss of about 0.2% of the total mass of the sample upon heating from ambient temperature to about 180° C. In certain embodiments, the aforementioned mass loss comprises a loss of solvent, such as, e.g., a loss of ethanol, 1-propanol, water or mixtures of two or more thereof.

In certain embodiments, the chemical profile of a sample of Form C of the esylate salt of Compound 6 of the esylate salt of Compound 6 can be characterized by solution NMR analysis. A representative $^1$H NMR spectrum of a sample of Form C of the esylate salt of Compound 6 dissolved in DMSO-d is provided as FIG. 33.

6.2.3 Form D of the Esylate Salt of Compound 6

Certain embodiments herein provide Form D crystal form of the esylate salt of Compound 6. Form D of the esylate salt of Compound 6 may be prepared by evaporation of an esylate salt of Compound 6 in a dimethylformamide (DMF) solution.

A representative XRPD pattern of Form D of the esylate salt of Compound 6 is shown in FIG. 35. In certain embodiments, Form D of the esylate salt of Compound 6 is characterized by XRPD peaks located at one or both of the following approximate positions: 6.5 and 13.4 degrees 2θ.

Representative thermal characteristics for Form D of the esylate salt of Compound 6 are shown in FIG. 37. A representative thermogram shown at the top of FIG. 37, comprises thermal events with maxima at approximately 73, 108 and 170° C.

In certain embodiments, Form D is characterized by a DSC thermogram comprising one or more thermal events with the following approximate temperature maxima: 73, 108 and 170° C. A representative TGA thermogram, shown at the bottom of FIG. 37, comprises a mass loss of about 3% of the total mass of the sample upon heating from ambient temperature to about 100° C. and a mass loss of about 6% of the total mass upon further heating from 100 to 200° C. In certain embodiments, the aforementioned mass loss comprises a loss of solvent, such as, e.g., a loss of DMF, water or mixtures of two or more thereof.

In certain embodiments, the chemical profile of a sample of Form D of the esylate salt of Compound 6 of the esylate salt of Compound 6 can be characterized by solution NMR analysis. A representative $^1$H NMR spectrum of a sample of Form D of the esylate salt of Compound 6 dissolved in DMSO-$d_6$ is provided as FIG. 36.

6.2.4 Crystal Form A of the Free Base of Compound 6

Certain embodiments herein provide a Form A crystal of the free base of Compound 6. In certain embodiments, the crystal Form A of the free base of Compound 6 can be obtained from various solvents, including, but not limited to, solvent systems comprising hexafluoroisopropanol (HFIPA), 1:2 mixture of HFIPA/chloroform, 1:2 mixture of HFIPA:dichloromethane (DCM), 1:1 mixture of dioxane/water, and mixtures of two or more thereof. A representative solution $^1$H NMR spectrum of the crystal form of the free base of Compound 6 dissolved in DMSO-$d_6$ is provided in FIG. 39. A representative XRPD pattern of the crystal form of the free base of Compound 6 is provided in FIG. 38. In one embodiment, the crystal form of the free base of Compound 6 is characterized by XRPD peaks located, at one or both of the following approximate positions: 8.2 and 24.5 degrees 2θ. In certain embodiments, Form A of the free base of Compound 6 is characterized by an XRPD pattern which matches the pattern exhibited in FIG. 38.

Representative thermal characteristics of Form A of the free base of Compound 6 is shown in FIG. 40. The DSC thermogram in FIG. 40 comprises an endothermic event at the following approximate temperature maxima: 97 and 196° C. In one embodiment, Form A of the free base of Compound 6 is characterized by a DSC thermogram comprising one or more thermal events with the following approximate temperature maxima: 97 and 196° C.

In certain embodiments, the chemical profile of a sample of Form A of the free base of Compound 6 of the esylate salt of Compound 6 can be characterized by solution NMR analysis. A representative $^1$H NMR spectrum of a sample of Form A of the esylate salt of Compound 6 dissolved in DMSO-d6 is provided as FIG. 39.

6.2.5 Amorphous Form of the Esylate Salt of Compound 6

In certain embodiments, provided herein is an amorphous form comprising the esylate salt of Compound 6. In certain embodiments, the amorphous form of the esylate salt of Compound 6 can be obtained by rotary evaporation in HFIPA. In certain embodiments, the amorphous form of the esylate salt of Compound 6 can be obtained by lyophilization in 1:1 dioxane/water mixture. In certain embodiments, Form A of the free base of Compound 6 is characterized by an XRPD pattern which matches the top pattern or second from the top pattern exhibited in FIG. 21.

In certain embodiments, the modulated thermogram of an amorphous form of the esylate salt of Compound 6 comprises an observable glass transition event at approximately 20° C. In certain embodiments, the modulated thermogram further comprises an endotherm at approximately 212° C. In certain embodiments, the modulated thermogram further comprises a change in heat capacity (ΔCp) of about 0.31 J/g° C.). In certain embodiments, an amorphous form of the esylate salt of Compound 6 is characterized by a modulated DSC thermogram which matches the thermogram exhibited in FIG. 22.

6.2.6 Form A of the Esylate Salt of Compound 0

Certain embodiments herein provide Form A crystal form of the esylate salt of Compound 0. In certain embodiments, Form A of the esylate salt of Compound 0 can be obtained by reacting Compound 0 with ethanesulfonic acid. In certain embodiments, Form A can be obtained by reacting Compound 0 with ethanesulfonic acid in various solvent systems, including, but not limited to, solvent systems comprising a protic solvent (e.g., methanol) an aprotic solvent (e.g., acetonitrile, a hydrocarbon (e.g., toluene) or a mixture of solvents (e.g., methanol and DCM or methanol and chloroform). In certain embodiments, Form A crystal form of the esylate salt of Compound 0 can be prepared by crystallization from solvent, water or solvent/water mixtures including, but not limited to, methanol, ethanol, isopropanol, 1-propanol, hexafluoroisopropanol, water, ethyl acetate, acetone, acetonitrile, dichloromethane, chloroform, isopropylether, tetrahydrofuran, methyl ethyl ketone, and mixtures of two or more solvents thereof. In certain embodiments, Form A crystal form of the esylate salt of Compound 0 can be prepared by crystallization from a variety of solvent systems, including, but not limited to, solvent systems comprising methanol, 1:1 methanol/chloroform mixture, 1:4 methanol/toluene mixture, 1:2 methanol/acetone mixture, ethanol, 1:1 ethanol/water mixture, l-propanol, isopropanol, 1:2 hexafluoroisopropanol/acetone mixture, 1:2 hexafluoroisopropanol/isopropyl ether mixture, 1:2 hexafluoroisopropanol/tetrahydrofuran mixture, acetonitrile, dioxane, 1:1 2,2,2,-trifluoroethanol/acetonitrile mixture, 1:1 2,2,2,-trifluoroethanolethyl acetate mixture, 1:1 2,2,2,-trifluoroethanol/isopropanol mixture, 1:1 2,2,2-trifluoroethanol/methyl ethyl ketone mixture and mixtures of two or more thereof. In certain embodiments, Form A of the esylate salt of Compound 0 can be obtained by crystallization from solvent, water or solvent/water mixtures including, but not limited to, common laboratory organic solvents.

For example, in one embodiment, Form A of the esylate salt of Compound 0 is obtained by precipitation from a solution comprising methanol or ethanol. For example, in one embodiment, Form A of the esylate salt of Compound 0 is obtained by precipitation from a solution comprising acetonitrile. In another embodiment, Form A of the esylate salt of Compound 0 is prepared by precipitation via evaporation and/or cooling from a solution comprising methanol or ethanol. In another embodiment, Form A of the esylate salt of Compound 0 is obtained by slurry in a solvent system comprising methanol, ethanol, isopropanol or 1-propanol. In certain embodiments, Form A of the esylate salt of Compound 0 can be obtained by crystallization from solvent, water or solvent/water mixtures including, but not limited to, common laboratory organic solvents. In certain embodiments, Form A is obtained by crystallization methods including, but not limited to, precipitation, slurry at ambient temperature, slurry at elevated temperature, slurry at sub-ambient temperature, evaporation, slow evaporation, fast evaporation and/or concentration. In certain embodiments, Form A of the esylate salt of Compound 0 is obtained by vapor diffusion using a solvent system comprising methanol or ethanol.

In certain embodiments, Form A of the esylate salt of Compound 0 is obtained by a process comprising the steps of; (1) contacting Form A of the esylate salt of Compound 0 with a solvent; and (2) isolating Form A of the esylate salt of Compound 0. In certain embodiments, Form A of the esylate salt of Compound 0 is purified via solvent-based purification methods, including solvent slurry. In particular embodiments, purification via solvent slurry reduces or removes one or more chemical impurities and/or physical impurities (e.g., one or more other crystal forms and/or amorphous forms).

In certain embodiments, Form A of the esylate salt of Compound 0 is obtained by a process comprising the steps of: (1) dissolving Form A of the esylate salt of Compound 0; and (2) recrystallizing Form A of the esylate salt of Compound 0. In certain embodiments, Form A of the esylate salt of Compound 0 is purified via recrystallization. In particular embodiments, such purification via recrystallization reduces or removes one or more chemical impurities, isomeric impurities and/or physical impurities (e.g., one or more other crystal forms and/or amorphous forms).

In certain embodiments, Form A of the esylate salt of Compound 0 is substantially pure. In certain embodiments, Form A of the esylate salt of Compound 0 is substantially free of chemical impurities. In certain embodiments, Form A of the esylate salt of Compound 0 is substantially free of isomeric impurities. In certain embodiments, Form A of the esylate salt of Compound 0 is substantially free of physical impurities, e.g., one or more other crystal forms and/or amorphous forms. In certain embodiments, Form A of the esylate salt of Compound 0 is substantially free of the free base of Compound 0. In certain embodiments, Form A of the esylate salt of Compound 0 is substantially free of other crystal forms comprising Compound 0.

In certain embodiments, Form A of the esylate salt of Compound 0 is characterized by a DSC thermogram comprising an endotherm with an onset temperature of about 216° C. In certain embodiments, Form A of the esylate salt of Compound 0 is characterized by a melting point of about 220° C. In certain embodiments, Form A of the esylate salt of Compound 0 is characterized by a melting point of about 222° C.

6.3 Methods of Use

Also provided herein are methods of using the solid forms comprising Compound 6 for the treatment, prevention, or amelioration of a disease or disorder that is mediated or otherwise affected via protein kinase activity or one or more symptoms of diseases or disorders that are mediated or otherwise affected via protein kinase activity (see. Krause and Van Etten, *N Engl J Med* (2005) 353(2):172-187, Blume-Jensen and Hunter, *Nature* (2001) 411(17): 355-365 and Plowman et al., DN&P, 7:334-339 (1994)).

In one embodiment, provided herein is a method of preventing, treating, or ameliorating one or more symptoms of a JAK-mediated condition, disorder, or disease in a subject, comprising administering to the subject a therapeutically effective amount of a compound provided herein, e.g., a solid form comprising Compound 6. In one embodiment, provided herein is a method of preventing, treating, or ameliorating one or more symptoms of an adenosine $A_3$-mediated condition, disorder, or disease in a subject, comprising administering to the subject a therapeutically effective amount of a compound provided herein, e.g., a solid form comprising Compound 6.

In one embodiment, provided herein is a method of treating, preventing, or ameliorating one or more symptoms of a proliferative disease, inflammatory disease, or renal disease in a subject, comprising administering to the subject a therapeutically effective amount of a solid form comprising Compound 6 or an isotopic variant thereof.

In another embodiment, provided herein is a method of treating, preventing, or ameliorating a proliferative disease, inflammatory disease, or renal disease in a subject, comprising administering to the subject a therapeutically effective amount of a solid form comprising Compound 6 or an isotopic variant thereof. In certain embodiments, the proliferative disease is a myeloproliferative disorder, including, but not limited to, polycythemia vera (PCV), essential thrombocythemia (ET), primary myelofibrosis (PMF), chronic eosinophilic leukemia (CEL), chronic myelomonocytic leukemia (CMML), systemic mastocytosis (SM), and idiopathic myelofibrosis (IMF). In certain embodiments, the proliferative disease is leukemia, including, but not limited to, myeloid leukemia, chronic myeloid leukemia (CML), imatinib-resistant CMLs, acute myeloid leukemia (AML), and acute megakaryoblastic leukemia (AMKL). In certain embodiments, the proliferative disease is a lymphoproliferative disease, including, but not limited to, myeloma. In certain embodiments, the proliferative disease is cancer, including, but not limited to, head and neck cancer, prostate cancer, breast cancer, ovarian cancer, melanoma, lung cancer, brain tumor, pancreatic cancer, and renal carcinoma.

In certain embodiments, the inflammatory disease or disorder, includes, but is not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosus (SLE), arthritis, osteoarthritis, rheumatoid arthritis, osteoporosis, asthma and chronic obstructive pulmonary disease (COPD), and dry eye syndrome (or keratoconjunctivitis sicca (KCS)). In certain embodiments, renal disease is diabetic neuropathy.

In yet another embodiment, provided herein is a method of treating, preventing, or ameliorating one or more symptoms of a JAK-mediated condition, disorder, or disease, in a subject, comprising administering to the subject a therapeutically effective amount of a solid form comprising Compound 6 or an isotopic variant thereof. In another embodiment, provided herein is a method of treating, preventing, or ameliorating a JAK-mediated condition, disorder, or disease, in a subject, comprising administering to the subject a therapeutically effective amount of a solid form comprising Compound 6 or an isotopic variant thereof. In certain embodiments, the JAK-mediated condition, disorder, or disease is a myeloproliferative disorder, including, but not limited to, polycythemia vera (PCV), essential thrombocythemia (ET), primary myelofibrosis (PMF), chronic eosinophilic leukemia (CEL), chronic myelomonocytic leukemia (CMML), systemic mastocytosis (SM), and idiopathic myelofibrosis (IMF). In certain embodiments, the JAK-mediated condition, disorder, or disease is leukemia, including, but not limited to, myeloid leukemia, chronic myeloid leukemia (CML), imatinib-resistant CMLs, acute myeloid leukemia (AML), and acute megakaryoblastic leukemia (AMKL).

In certain embodiments, the JAK-mediated condition, disorder, or disease is a lymphoproliferative disease, including, but not limited to, myeloma.

In certain embodiments, the JAK-mediated condition, disorder, or disease is cancer, including, but not limited to, head and neck cancer, prostate cancer, breast cancer, ovarian cancer, melanoma, lung cancer, brain tumor, pancreatic cancer, and renal carcinoma. In certain embodiments, the JAK-mediated condition, disorder, or disease is a inflammatory disease or disorder, including, but not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosus (SLE), arthritis, osteoarthritis, rheumatoid arthritis, osteoporosis, asthma and chronic obstructive pulmonary disease (COPD), and dry eye syndrome (or keratoconjunctivitis sicca (KCS)). In certain embodiments, the proliferative disease or the JAK-mediated condition, disorder, or disease is selected from myeloproliferative disorders, including, but not limited to, polycythemia vera (PCV), essential thrombocythemia, idiopathic myelofibrosis (IMF), and hypereosinophilic syndrome (HES); leukemia, including, but not limited to, myeloid leukemia, chronic myeloid leukemia (CML), imatinib-resistant CMLs, acute myeloid leukemia (AML), acute lymphoblastic leukemia (ALL), and acute megakaryoblastic leukemia (AMKL); lymphoproliferative diseases, including, but not limited to, myeloma; cancer, including, but not limited to, head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, and melanoma. In certain embodiments, the inflammatory disease or the JAK-mediated condition, disorder, or disease is selected from, but not limited to diseases relating to immune dysfunction, immunodeficiency or immunomodulation, including but not limited to tissue transplant rejection, graft-versus-host disease, wound healing, kidney disease, diabetic neuropathy, autoimmune diseases, multiple sclerosis, thyroiditis, type 1 diabetes, sarcoidosis, psoriasis, allergic rhinitis, atopic dermatitis, myasthenia gravis, inflammatory bowel diseases, Crohn's disease, ulcerative colitis (UC), systemic lupus erythematosus (SLE), arthritis, osteoarthritis, rheumatoid arthritis, osteoporosis, asthma and chronic obstructive pulmonary disease (COPD), conjunctivitis, dry eye syndrome (or keratoconjunctivitis sicca (KCS)), uveitis, iritis, scleritis, rhinitis, sinusitis, bronchitis, myocarditis, ischemia reperfusion injuries, systemic inflammatory response syndrome (SIRS), and sepsis.

In certain embodiments, the renal disease or the JAK-mediated condition, disorder, or disease includes diabetic neuropathy.

In certain embodiments, JAK-mediated diseases and disorders include, but are not limited to, restenosis, fibrosis, and scleroderma. In certain embodiments, JAK-mediated diseases include, but are not limited to, viral diseases such as Epstein Barr virus (EBV), hepatitis (hepatitis B or hepatitis C), human immunodeficiency virus (HIV), human Tlymphotropic virus type 1 (HTLV-1), varicella-zoster virus, and the human papilloma virus (HPV).

In certain embodiments, adenosine $A_3$-mediated diseases and disorders include inflammatory diseases of the lower respiratory tract including bronchitis; inflammatory myopathy such asmyocarditis, other inflammatory diseases such as ischemia reperfusion injuries related to an inflammatory ischemic event such as a stroke or cardiac arrest In certain embodiments, adenosine $A_3$-mediated diseases and disorders include restenosis, fibrosis and scleroderma. In certain embodiments, adenosine $A_3$-mediated diseases include viral diseases such as Epstein Barr virus (EBV), hepatitis (hepatitis B or hepatitis C), human immunodeficiency virus (HIV), Human T-lymphotropic virus type 1 (HTLV-1), varicella-zoster virus and the human papilloma virus (HPV).

In certain embodiments, the adenosine $A_3$-mediated condition, disorder, or disease is a cardiovascular disease, including, but not limited to, ischaemic heart disease. In certain embodiments, the adenosine A3-mediated condition, disorder, or disease is atherosclerosis. See, WO 2010/009190, the disclosure of which is incorporated herein by reference in its entirety. In certain embodiments, the adenosine A3-mediated condition, disorder, or disease is lung injury. In certain embodiments, the adenosine A3-mediated condition, disorder, or disease is renal failure. See, Lee, et al., *Am. J. Physiol. Renal Physiol.* 2002, 284, F267-273. In certain embodiments, the adenosine A3-mediated condition, disorder, or disease is an eye disease, including, but not limited to, glaucoma and ocular hypertension. In certain embodiments, the adenosine A3-mediated condition, disorder, or disease is colon cancer or multidrug resistant cancer. See, WO 2004/000224, the disclosure of which is incorporated herein by reference in its entirety.

In certain embodiments, provided herein are methods of preventing, treating, or ameliorating hyper pigmentation of the skin, comprising administering to a subject a therapeutically effective amount of a compound provided herein, e.g., a compound of Formula (I), including or a single enantiomer, a mixture of enantiomers, a mixture of diastereomers, or an isotopic variant thereof; or a pharmaceutically acceptable salt, solvate, or prodrug thereof. See, WO 2011/010306, the disclosure of which is incorporated herein by reference in its entirety. In certain embodiments, provided herein are methods of lightening the skin comprising administering to a subject a therapeutically effective amount of a compound provided herein, e.g., a compound of Formula (I), including or a single enantiomer, a mixture of enantiomers, a mixture of diastereomers, or an isotopic variant thereof, or a pharmaceutically acceptable salt, solvate, or prodrug thereof.

In certain embodiments, provided herein are methods of preventing, treating, or ameliorating one or more symptoms of toxin exposure, comprising administering to a subject a therapeutically effective amount of a solid form comprising Compound 6, or an isotopic variant thereof.

In certain embodiments, provided herein are methods of preventing, treating, or ameliorating one or more symptoms of hyperreactivity to aspirin, comprising administering to a subject a therapeutically effective amount of a solid form comprising Compound 6 or an isotopic variant thereof.

In certain embodiments, provided herein are methods of increasing the beneficial effects of hypertonic saline (HS) resuscitation, comprising administering to a subject a therapeutically effective amount of a solid form comprising Compound 6, or an isotopic variant thereof. See, Inoue et al., *Shock,* 2011, 35, 178-183. In certain embodiments, the increase in the beneficial effects of hypertonic saline (HS) resuscitation occurs when treating sepsis.

In certain embodiments, provided herein are methods of using a solid form comprising Compound 6 or an isotopic variant thereof as a male contraceptive. See, Burnett et al., *J. Biol. Chem.* 2010, 285, 33662-33670.

In certain embodiments, provided herein are methods of using a solid form comprising Compound 6 or an isotopic variant thereof, as an analgesic.

In certain embodiments, provided herein are methods of using a solid form comprising Compound 6 or an isotopic variant thereof, for neuroprotection. See, Pugliese, et al., 2006, 147, 524-532. In certain embodiments, provided herein are methods of inhibiting eosinophil degranulation, comprising administering to a subject a therapeutically effective amount of a solid form comprising Compound 6 or an isotopic variant thereof.

6.4 Combination Therapy

The solid form of compound 6 provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the second therapeutic agent is a chemotherapeutic agent, anti-proliferative agent, anti-inflammatory agent, immunomodulatory agent, or immunosuppressive agent. In one embodiment, the second therapeutic agent is an anticancer agent. In one embodiment, the anticancer agent is an antimetabolite, including, but not limited to, cytarabine (also known as cytosine arabinoside or Ara-C), fludarabine, 5-fluorouracil, gemcitabine, HDAC (high dose cytarabine), 6-mercaptopurine, methotrexate, and pemetrexed. In another embodiment, the anticancer agent is an antimicrotubule agent, including, but not limited to, vinca alkaloids (e.g., vinblastine, vincristine, and vinorelbine) and taxanes (e.g., paclitaxel, albumin-bound paclitaxel (ABRAXANE®), and docetaxel). In yet another embodiment, the anticancer agent is an alkylating agent, including, but not limited to, busulfan, carmustine, chlorambucil, cyclophospbamide, fludarabine, ifosfamide, mechlorethamine, melphalan, and nitrosoureas (e.g., bischloroethylnitrosurea, hydroxyurea, carmustine, and lomustine). In yet another embodiment, the anticancer agent is a platinum agent, including, but not limited to, carboplatin, CI-973, cisplatin, oxaliplatin, and satraplatin (JM-216). In yet another embodiment, the anticancer agent is an anthracycline, including, but not limited to, adriamycin, daunorubicin, and doxrubicin. In yet another embodiment, the anticancer agent is an antitumor antibiotic, including, but not limited to, adriamycin, bleomycin, daunomycin (also known as daunorubicin), doxorubicin, idarubicin, and mitomycin. In yet another embodiment, the anticancer agent is a topoisomerase inhibitor, including, but not limited to, camptothecins, etoposide, irinotecan, and topotecan. In yet another embodiment, the anticancer agent is a kinase inhibitor, including, but not limited to, erlotinib and imatinib. In yet another embodiment, the anticancer agent is a nucleoside, including, but not limited to, gemcitabine. In yet another embodiment, the anticancer agent is an anti-angiogenesis agent, including, but not limited to, SUTENT®, sorafenib, and bevacizumab. In yet another embodiment, the anticancer agent is a cytotoxic agent, including, but not limited to, estramustine phosphate and prednimustine. In yet another embodiment, the anticancer agents are hormones or hormone agonists, antagonists, partial agonists or partial antagonists. In yet another embodiment, the anticancer agent is selected from the group consisting of enzymes (asparaginase), hormones (tamoxifen, leuprolide, flutamide, and megestrol), hydroxyurea, interferons, and oblimersen. In still another embodiment, the anticancer agent is a monoclonal antibody, including, but not limited to bevacizumab and cetuximab. For a more comprehensive discussion of updated cancer therapies; See, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

6.5 Administration

Provided herein are pharmaceutical compositions, which comprise the solid forms comprising Compound 6, or a pharmaceutically acceptable salt thereof, as an active ingredient, in combination with one or more pharmaceutically acceptable excipients or carriers. In one embodiment, the pharmaceutical composition comprises at least one nonrelease controlling excipient or carrier. In another embodiment, the pharmaceutical composition comprises at least one release controlling and at least one nonrelease controlling excipient or carrier.

The solid forms comprising Compound 6 may be administered alone, or in combination with one or more other active ingredients (i.e., other therapeutic agents). The pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

The pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Suitable fillers and diluents include, but are not limited to, talc, calcium carbonate, microcrystalline cellulose, powdered cellulose, dextrates, kaolin, mannitol, silicic acid, sorbitol, starch, pre-gelatinized starch, dicalcium phosphate, calcium sulfate, lactose, sucrose, inositol, sodium chloride, dry starch, and powdered sugar and mixtures thereof. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The filler and/or diluent may be present from about 20 to about 99% by weight in the pharmaceutical compositions provided herein.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. The binder or granulator may be present from about 0.5 to about 20% by weight in the pharmaceutical compositions provided herein.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, includes intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinyl-alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPM-CAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rapture of a thinner portion of the membrane over an indentation in the core. In addition, delivery ports may be formed during coating process, as in the case of asymmetric membrane coatings of the type disclosed in U.S. Pat. Nos. 5,612,059 and 5,698, 220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 mm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Incorporation by Reference

This application incorporates by reference in its entirety the U.S. patent application Ser. No. 13/223,099 filed with the U.S. Patent Office on Aug. 31, 2011, entitled: OPTICALLY ACTIVE PYRAZOLYLAMINOQUINAZOLINE, AND PHARMACEUTICAL COMPOSITIONS AND METH-ODS OF USE THEREOF, which discloses, inter alia, pharmaceutical compositions comprising Compound 6 and methods of administering Compound 6.

The following examples present certain exemplary embodiments and are intended by way of illustration and not by way of limitation. In each of the examples herein, percentages indicate weight percent of the total mixture, unless otherwise indicated.

7. EXAMPLES

The following Examples are presented by way of illustration, not limitation. The following abbreviations are used herein:

| Abbreviation | Full Name |
|---|---|
| XRPD | x-ray powder diffractometry |
| DSC | differential scanning calorimetry |
| mDSC | modulated differential scanning calorimetry |
| TGA | thermogravimetric analysis |
| HSM | hot-stage microscopy |
| KF | Karl-Fischer titration |
| NMR | nuclear magnetic resonance spectroscopy |
| SE | slow evaporation |
| FE | fast evaporation |
| SC | slow cooling |
| CC | crash cooling |
| VD | vapor diffusion |
| VS | vapor stress |
| RT | room temperature |
| RH | relative humidity |
| B | birefringence |
| E | extinction |
| d | day |
| min | minute |
| endo | endotherm |

7.1 Solid Form Screen and Characterization 7.1.1 Solubility Measurements

A weighed sample was treated with aliquots of the test solvent at room temperature or elevated temperature. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" (<) if dissolution did not occur during the experiment if complete dissolution was achieved as a result of only one aliquot addition, the solubility is expressed as "greater than"

7.1.2 Crystal Form Screen

Both thermodynamic and kinetic crystallization techniques were employed. These techniques are described in more detail below. Once solid samples were harvested from crystallization attempts, they were either examined under a microscope for birefringence and morphology or observed with the naked eye. Any crystalline shape was noted, but sometimes the solid exhibited unknown morphology, due to small particle size. Solid samples were then analyzed by XRPD, and the crystalline patterns compared to each other to identify new crystal forms.

Antisolvent Precipitation: Solutions were prepared in various solvents and filtered through a 0.2-μm nylon filter into a vial. Antisolvent was then added until precipitation was observed. The resulting solids were isolated by vacuum filtration and analyzed.

Crash Cool (CC): Solutions were prepared in various solvents at an elevated temperature and filtered warm through a 0.2-μm nylon filter into a warm vial. The vial was placed in a (dry ice+isopropanol) cooling bath. Samples were placed into a freezer if no solids were observed to immediately precipitate. If there were no solids present, the solution was warmed up to ambient temperature and antisolvent was then added until precipitation was observed. The resulting solids were isolated by vacuum filtration and analyzed.

Fast Evaporation (FE): Solutions were prepared in various solvents and sonicated between aliquot additions to assist in dissolution. Once a mixture reached complete dissolution, as judged by visual observation, the solution was filtered through a 0.2-μm nylon filter. The filtered solution was allowed to evaporate at ambient in an uncapped vial. Solutions were evaporated to dryness unless designated as partial evaporations. The solids that formed were isolated and analyzed.

Freeze-Drying (Lyophilization): Solutions were prepared in 1:1 dioxane: water, filtered through a 0.2-μm nylon filter, and frozen in a vial or flask immersed in a bath of dry ice and isopropanol. The vial or flask containing the frozen sample was attached to a Flexi-Dry lyophilizer and dried for a measured time period. After drying, the solids were isolated and stored in the freezer over desiccant until used.

Milling: A solid sample was placed into a stainless steel grinding jar with a grinding ball. The sample was then ground at 30 Hz on a ball mill (Retsch Mixer Mill model MM200) for a set amount of time. The solids were collected and analyzed.

Rotary Evaporation: Solutions of ethanesulfonate salt of Compound 6 in HFIPA were prepared. Solids were obtained by rotary evaporation of the solvent under vacuum, with the sample vial immersed in a heated water bath at approximately 40° C. Solids were then continued to be dried for additional approximately 10 minutes under vacuum at ambient temperature. After evaporation, the solids were stored in the freezer over desiccant until used.

Slow Cooling (SC): Solutions were prepared in various solvents at an elevated temperature. The solutions were filtered warm through a 02-μm nylon filter into a warm vial. The vial was capped and left on the hot plate, and the hot plate was turned off to allow the sample to cool slowly to ambient temperature. If no solids were present after cooling to ambient temperature, the sample was placed in a refrigerator and/or freezer for further cooling. If there were no solids present in the freezer, the solution was warmed up to ambient temperature and antisolvent was then added until precipitation was observed. Solids were collected by vacuum filtration and analyzed.

Slow Evaporation (SE): Solutions were prepared in various solvents and sonicated between aliquot additions to assist in dissolution. Once a mixture reached complete dissolution, as judged by visual observation, the solution was filtered through a 0.2-μm nylon filter. The filtered solution was allowed to evaporate at ambient conditions in a vial covered with aluminum foil perforated with pinholes. Solutions were evaporated to dryness unless designated as partial evaporations. The solids that formed were isolated and analyzed.

Slurry Experiments: Suspensions were prepared by adding enough solids to a given solvent so that excess solids were present. The mixture was then agitated in a sealed vial at ambient temperature or an elevated temperature. After a given period of time, the solids were isolated by vacuum filtration and analyzed.

Vapor Diffusion (VD): Solutions were prepared in various solvents and filtered through a 0.2-μm nylon filter. The filtered solution was dispensed into a 1-dram vial, which was then placed inside a 20-mL vial containing antisolvent. The 1-dram vial was left uncapped and the 20-mL vial was capped to allow vapor diffusion to occur. The resulting solids were isolated and analyzed.

Vapor Stress (VS): A solid sample was placed into a 1-dram vial. The 1-dram vial was then placed into a 20-mL vial containing solvent. The 20-mL vial was capped and left at ambient for a measured time period. Samples were analyzed after removal from the stress environment.

7.1.3 Instrumental Techniques 7.1.3.1 Differential Scanning Calorimetry (DSC)

DSC was performed using a TA Instruments differential scanning calorimeter Q2000. Temperature calibration was performed using NIST traceable indium metal. The sample was placed into an aluminum DSC pan, covered with a lid, and the weight was accurately recorded. The data acquisition parameters and pan configuration are displayed in the image of each thermogram. Generally, the sample cell was equilibrated at about 25° C. and heated under a nitrogen purge at a rate of about 10° C./min, up to a final temperature of about 250° C. To determine the glass transition temperature (Tg) of amorphous material, the sample cell was cycled several times between about −40 and about 70° C. The Tg is reported from the inflection point of the transitions as the average value.

7.1.3.2 Hot Stage Microscopy (HSM)

Hot stage microscopy was performed using a Linkam hot stage (model FTIR 600) mounted on a Leica DM LP microscope. Samples were observed using a 10 or 20× objective (obj.). Samples were placed on a coverslip, and a second coverslip was then placed over the sample. Each sample was visually observed as the stage was heated. Images were captured using a SPOT Insight™ color digital camera with SPOT Software v. 4.5.9. The hot stage was calibrated using USP melting point standards.

7.1.3.3 Karl-Fischer (KF)

Coulometric Karl Fischer (KF) analysis for water determination was performed using a Mettler Toledo DL39 Karl Fischer titrator. Sample was placed in the KF titration vessel containing of Hydranal-Coulomat AD and mixed for 10 seconds to ensure dissolution. The sample was then titrated by means of a generator electrode which produces iodine by electrochemical oxidation: 2 I−=>$I_2$+2e. Two replicates were obtained to ensure reproducibility.

7.1.3.4 Modulated Differential Scanning Calorimetry (mDSC)

Modulated differential scanning calorimetry data were obtained on a TA Instruments differential scanning calorimeter equipped with a refrigerated cooling system (RCS). Temperature calibration was performed using NIST traceable indium metal. The sample was placed into an aluminum DSC pan, and the weight accurately recorded. The data acquisition parameters and pan configuration are displayed in the image of each thermogram. In certain cases, mDSC data were obtained using a modulation amplitude of +/−0.8° C. and a 60 second period with an underlying heating rate of about 2° C./min from about −30 to about 150° C. The reported $T_g$ is obtained from the inflection point of the step change in the reversible heat flow versus temperature curve.

7.1.3.5 Nuclear Magnetic Resonance (NMR)

The solution $^1$H NMR spectra were acquired at ambient temperature on a Varian $^{UNITY}$INOVA-400 spectrometer. Samples were prepared for NMR spectroscopy as ~5-50 mg solutions in the appropriate deuterated solvent. The specific acquisition parameters are listed on the plot of the first full spectrum of each sample in the data section. Generally, spectra were referenced to internal tetramethylsilane at 0.0 ppm.

7.1.3.6 Optical Microscopy (OM)

Observations made by optical microscopy were performed using a Leica MZ12.5 stereomicroscope. Various objectives typically ranging from 0.8-10× were used with crossed-polarized light to view samples.

7.1.3.7 Thermogravimetric Analysis (TGA)

TG analyses were performed using a TA Instruments thermogravimetric analyzer model 2950. Temperature calibration was performed using nickel and Alumel™. Each sample was placed in an aluminum pan. The sample was hermetically sealed, the lid pierced, then inserted into the TG furnace. The furnace was heated under nitrogen. Generally, samples were first equilibrated at about 25° C. or started directly from ambient conditions, then heated under a stream of nitrogen at a heating rate of about 10° C./min, up to a final temperature of about 300 or about 350° C. unless specified otherwise. The data acquisition parameters for each pattern are displayed in the image in the Data section of this report. The data acquisition parameters are displayed in the image of each thermogram.

7.1.3.8 X-Ray Powder Diffraction (XRPD)

X-ray power diffraction analyses were performed on any one of the following three instruments as specified.

Inel XRG-3000: X-ray powder diffraction analyses were performed on an Inel XRG-3000 diffractometer, equipped with a curved position-sensitive detector with a 2θ range of 120°. Real time data was collected using Cu Kα radiation at a resolution of 0.03 °2θ. The tube voltage and amperage were set to 40 kV and 30 mA, respectively. Patterns are displayed from 2.5 to 40 °2θ to facilitate direct pattern comparisons. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard. The data acquisition and processing parameters are displayed on each pattern found in the data section.

Bruker D-8 Discover Diffractometer. XRPD patterns were collected with a Bruker D-8 Discover diffractometer and Bruker's General Area Diffraction Detection System (GADDS, v. 4.1.20). An incident beam of Cu Kα radiation was produced using a fine-focus tube (40 kV, 40 mA), a Göbel mirror, and a 0.5 mm double-pinhole collimator. The sample was packed between 3-micron thick films to form a portable disc-shaped specimen. The prepared specimen was loaded in a holder secured to a translation stage and analyzed in transmission geometry. The incident beam was scanned and rastered to optimize orientation statistics. A beam-stop was used to minimize air scatter from the incident beam at low angles. Diffraction patterns were collected using a Hi-Star area detector located 15 cm from the sample and processed using GADDS. Prior to the analysis a silicon standard was analyzed to verify the Si 111 peak position. The data acquisition and processing parameters are displayed on each pattern found in the data section.

PANalytical X'Pert Pro Diffractometer. XRPD patterns were collected using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated parallel to the diffraction vector to optimize orientation statistics. A beam-stop and helium purge was used to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in the data section. Prior to the analysis a silicon specimen (NIST standard reference material 640d) was analyzed to verify the position of the silicon 111 peak.

For XRPD peak identification process, under most circumstances, peaks within the range of up to about 30° 2θ were selected. Although peaks are labeled on diffraction patterns and listed in tables, for technical reasons, different rounding algorithms were used to round each peak to the nearest 0.1° or 0.01° 2θ, depending upon the instrument used to collect the data and/or the inherent peak resolution. The location of the peaks along the x-axis (°2θ) in both the figures and the tables were automatically determined using proprietary software Pattern Match 3.0.4 and rounded to one or two significant figures after the decimal point based upon the above criteria. Peak position variabilities are given to within ±0.2° 2θ based upon recommendations outlined in the USP discussion of variability in x-ray powder diffraction (United States Pharmacopeia, USP 33 reissue, NF 28, <941>, R-93, Oct. 1, 2010). The accuracy and precision associated with any particular measurement reported herein has not been determined. Moreover, third party measurements on independently prepared samples on different instruments may lead to variability which is greater than ±0.1° 2θ. For d-space listings, the wavelength used to calculate d-spacings was 1.541874 Å, a weighted average of the Cu-$K_{\alpha 1}$ and Cu-$K_{\alpha 2}$ wavelengths (See, 4476-36. *Phys. Rev.* A56(6) 4554-4568 (1997)). Variability associated with d-spacing estimates was calculated from the USP recommendation, at each d-spacing, and provided in the respective data tables.

For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.1° 2θ. Not all crystalline polymorphs of a compound necessarily have at least one characteristic peak.

In general, as understood in the art, two XRPD patterns match one another if the characteristic peaks of the first pattern are located at approximately the same positions as the characteristic peaks of the second pattern. As understood in the art, determining whether two XRPD patterns match may require consideration of individual variables and parameters such as, but not limited to, preferred orientation, phase impurities, degree of crystallinity, particle size, variation in diffractometer instrument setup, variation in XRPD data collection parameters, and variation in XRPD data processing, among others.

7.2 Example 1

Synthesis of (4-Fluorophenyl(4-(5-Methyl-1H-Pyrazol-3-Ylamino)Quinazolin-2-yl)methanone

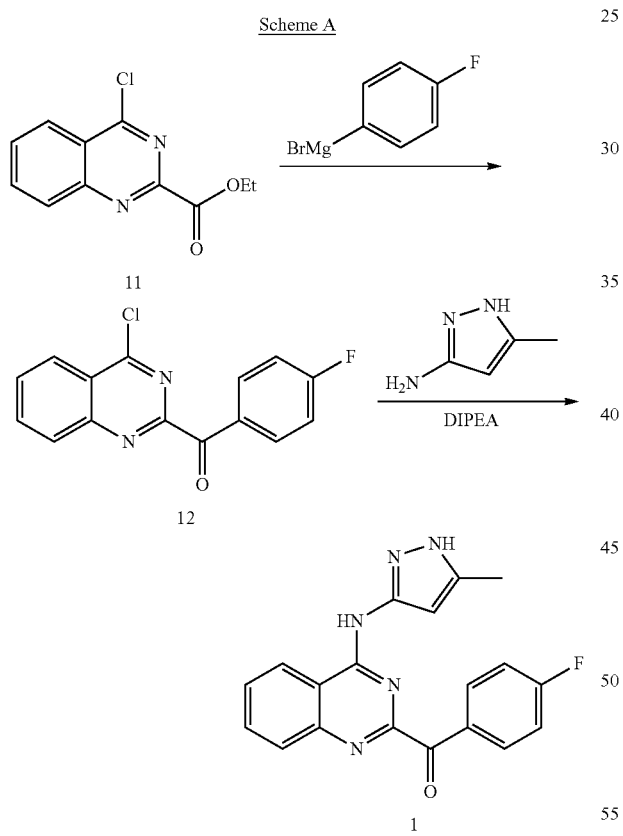

Step A. Preparation of (4-chloroquinazoline-2-yl)(4-fluorophenyl)methanone 12. As shown in Scheme A, to a solution of ethyl 4-chloroquinazoline-2-carboxylate 11 (0.6 g, 2.53 mmol) in THF (6 mL) at −40° C. was added dropwise a solution of 4-fluorophenylmagnesium bromide in THF (1 M, 3 mL, 3.0 mmol, 12 eq). The reaction mixture was stirred at −40° C. for 4 hrs. The reaction was quenched by addition of 0.5 N HCl (5 mL) and the mixture was extracted with EtOAc (2×10 mL). The combined organic layers were washed with brine, dried over anhydrous MgSO4 and concentrated. The crude product was purified by silica gel chromatography eluting with EtOAc/hexanes to afford compound 12 as a light yellow solid (440 mg, 60%). $^1$H NMR (300 MHz, DMSO-d6) 7.45-7.40 (m, 2H), 8.07-8.03 (m, 1H), 8.17-8.13 (m, 2H), 8.23 (m, 2H), 8.42 (d, 1H); LC-MS (ESI) m/z: 287 (M+H)$^+$.

Step B. Preparation of (4-fluorophenyl)(4-(5-methyl-1H-pyrazol-3-ylamino)quinazolin-2-yl)methanone 1. To a solution of compound 12 (84 mg, 030 mmol) in DMF (3 mL) at room temperature were added diisopropylethylamine (DIPEA) (0.103 mL, 0.6 mmol) and 5-methyl-1H-pyrazol-3-amine (88 mg, 0.9 mmol). The reaction mixture was heated at 40° C. overnight Water was added, and the yellow precipitate was collected by filtration and washed with water. The solid was purified by silica gel chromatography eluting with DCM/MeOH to give compound 1 (30 mg, 29%). $^1$H NMR (300 MHz, DMSO-d6) 2.19 (s, 3H), 6.54 (s, 1H), 7.40 (m, 2H), 7.68 (t, 1H), 7.9-7.7 (m, 2H), 8.08 (n, 2H), 8.74 (d, 1H), 10.66 (s, 1H), 12.20 (s, 1H); LC-MS (ESI) m/z: 348 (M+H)+.

7.3 Example 2

Synthesis of (R)-(4-Fluorophenyl(4-((5-Methyl-1H-Pyrazol-3-Yl)Amino)Quinazolin-2-Yl)Methanol ("Compound 6")

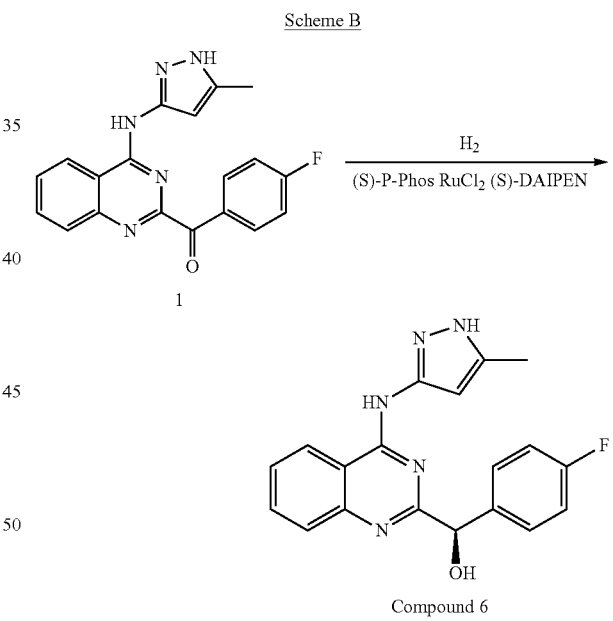

A 600 mL Parr vessel was charged with (4-fluorophenyl)(4-(5-methyl-1H-pyrazol-3-ylamino)quinazolin-2-yl)methanone 1 (80.16 g, 231 mmol), (S)-PPhos RuCl$_2$ (S)-DAIPEN (65.3 mg, substrate to catalyst ratio (S/C) 4,000/1), a solution of i-PrOH—H$_2$O (9:1 v/v, 324 mL) and DMSO (36 mL). The vessel was sealed and purged with N$_2$ by filling to 3 bar for 1 min and then venting, a further 5 purges was done with stirring (1500 rpm). A solution of t-BuOK/t-BuOH (1M, 348 μL) in i-PrOH—H$_2$O (9:1 v/v, 10 mL) was added and the reaction purged with N$_2$ according to the previous sequence. The vessel was then purged with H$_2$ by filling to 5 bar for 2 min and venting, a further 3 purges was done with stirring (1500 rpm). The reaction was then heated to 70° C. and maintained at this temperature and pressure for the indicated time.

The vessel was allowed to cool to room temperature before purging with nitrogen. The reaction slurry was diluted with $H_2O$ (260 mL) and filtered. The resulting solid Compound 6 was washed with i-PrOH—$H_2O$ (1:1 v/v) 2×100 mL) and dried under high vacuum until constant mass was achieved.

71.75 g isolated yield, 89.0%. HPLC analysis indicated 99.5% product and 0.5% starting material. The product enantiomeric excess of 99.1% in favor of the late eluting R enantiomer.

7.4 Example 3

Salt Screen of Compound 6

A total of eight 40-mL screw-top vials were charged with Compound 6 free base. The amount of acid to equal one equivalent (in the case of di- and tri-protic acids, one equivalent of the counter ion was used resulting in two or three equivalents of proton) was determined (Table 1).

TABLE 1

| Vial | Compound 6 g (mmol) | Acid | Acid F.W. | ρ | Conc (%) | Acid Amount |
|---|---|---|---|---|---|---|
| A1 | 0.40360 (1.16) | Benzenesulfonic acid | 158.18 | | | 182.7 mg |
| A2 | 0.41470 (1.19) | Ethanesulfonic acid | 110.13 | 1.35 | | 96.8 μL |
| A3 | 0.47580 (1.36) | Hydrobromic acid | 80.91 | 1.49 | 48 | 154.1 μL |
| A4 | 0.42084 (1.20) | Hydrochloric acid | 36.46 | 1.2 | 3.7 | 98.9 μL |
| A5 | 0.41268 (1.18) | Methanesulfonic acid | 96.11 | 1.481 | | 76.7 μL |
| A6 | 0.36919 (1.06) | Sulfuric acid | 98.08 | 1.84 | 95 | 59.3 μL |
| A7 | 0.41022 (1.17) | Phosphoric acid | 98 | | | 115.1 μL |
| A8 | 0.42939 (1.23) | p-Toluenesulfonic acid•H2O | 190.22 | | | 233.8 mg |

The vials, containing Compound 6 free base, were charged with ethanol (10 mL) and heated with a heat gun until a solution was obtained. The caps were removed and the corresponding acids were carefully added. Upon addition of sulfuric and phosphoric acid, precipitation was immediately observed. The solvent was removed under a stream of air and the solids obtained were further dried under high vacuum. The resulting solids were analyzed by DSC and portions of each salt were tested for solubility and crystallization from the following solvents:

Water ($H_2O$)
Methanol (MeOH)
Ethanol (EtOH)
Isopropyl alcohol (IPA)
Acetonitrile (MeCN)
Acetone
Dichloromethane (DCM)
Tetrahydrofuran (THPF)
Ethyl acetate (EtOAc)

20 mg of salt was charged to a 1-dram screw-top vial. Solvent (enough to cover the solids) was added, the vial was capped and heated (heat gun) to aid dissolution. If no, or partial dissolution was observed, the vial was allowed to cool, additional solvent was added and the process repeated. The solubility was characterized as follows: Soluble (sol): the solids dissolved upon heating, Sparingly soluble (sp): the solids dissolved upon heating after two or more additions of solvent or Insoluble (I): complete dissolution could not be achieved. This characterization of solubility is a qualitative property and should not be confused with quantitative measures of solubility such as that provided in the USP. Vials that demonstrated solubility were allowed to cool (uncontrolled) to room temperature and the observance of crystallization (or precipitation) was recorded at various time points. The vials containing solids were filtered and analyzed by DSC. The most promising salts were scaled up and subjected to a quantitative solubility screen and rat PK analysis.

The results from the solubility/crystallization screen is shown below in Table 2 (sol=soluble, sp=sparingly soluble, I=insoluble, cryst=crystallized and trace=trace crystallized).

TABLE 2

| Acid | Condition | $H_2O$ | MeOH | EtOH | IPA |
|---|---|---|---|---|---|
| Benzenesulfonic acid | Heating | I | sol | sp | sp |
| | standing 1 d | n/a | trace | cryst | cryst |
| | standing 4 d | n/a | trace | cryst | cryst |
| Ethanesulfonic acid | Heating | sol | sol | sol | sol |
| | standing 1 h | gels | sol | cryst | cryst |
| | standing 4 d | n/a | sol | cryst | cryst |
| Hydrobromic acid | Heating | sol | sol | sol | sp |
| | standing 1 h | cryst | sol | cryst | cryst |
| | standing 4 d | cryst | sol | cryst | cryst |
| Hydrochloric acid | Heating | sol | sol | sol | I |
| | standing 1 d | cryst | sol | cryst | n/a |
| | standing 4 d | cryst | sol | cryst | n/a |
| Methanesulfonic acid | Heating | sol | sol | sol | I |
| | standing 1 d | gels | cryst | cryst | n/a |
| | standing 4 d | n/a | cryst | cryst | n/a |
| Phosphoric acid | Heating | sp | I | I | I |
| | standing 1 h | gels | n/a | n/a | n/a |
| | standing 4 d | n/a | n/a | n/a | n/a |
| Sulfuric acid | Heating | sp | I | I | I |
| | standing 1 h | cryst | n/a | n/a | n/a |
| | standing 4 d | cryst | n/a | n/a | n/a |
| p-Toluenesulfonic acid | Heating | sp | sol | sol | sp |
| | standing 1 d | cryst | sol | cryst | cryst |
| | standing 4 d | cryst | sol | cryst | cryst |

Figure 1:
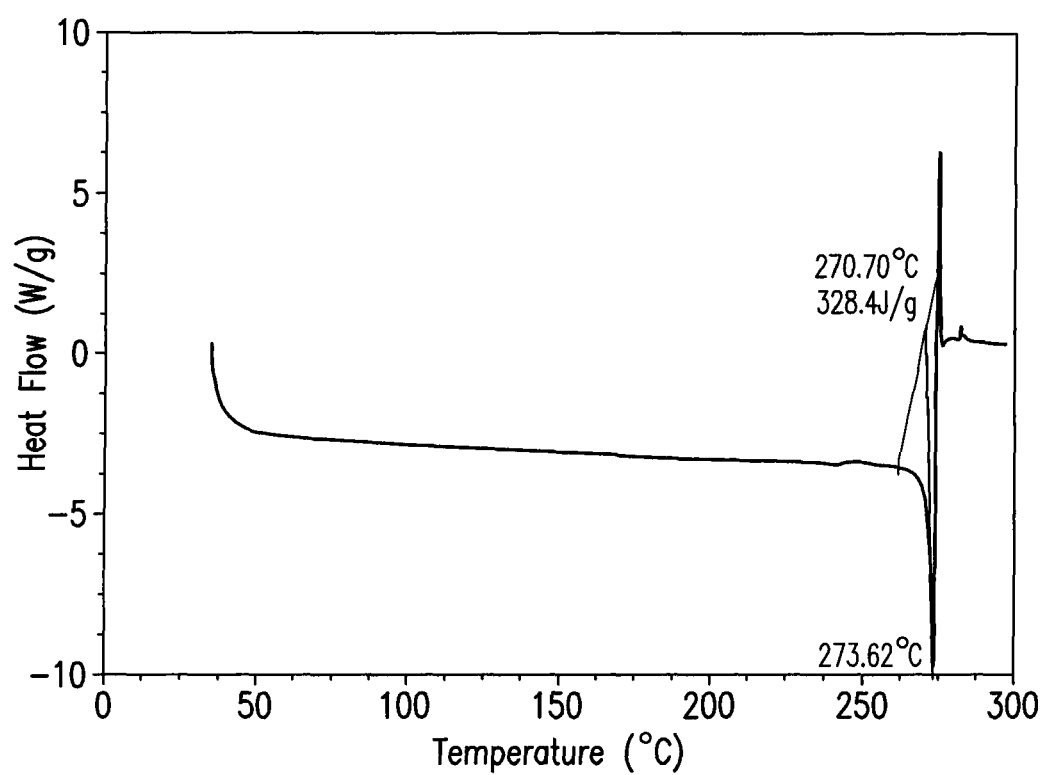
Figure 2:
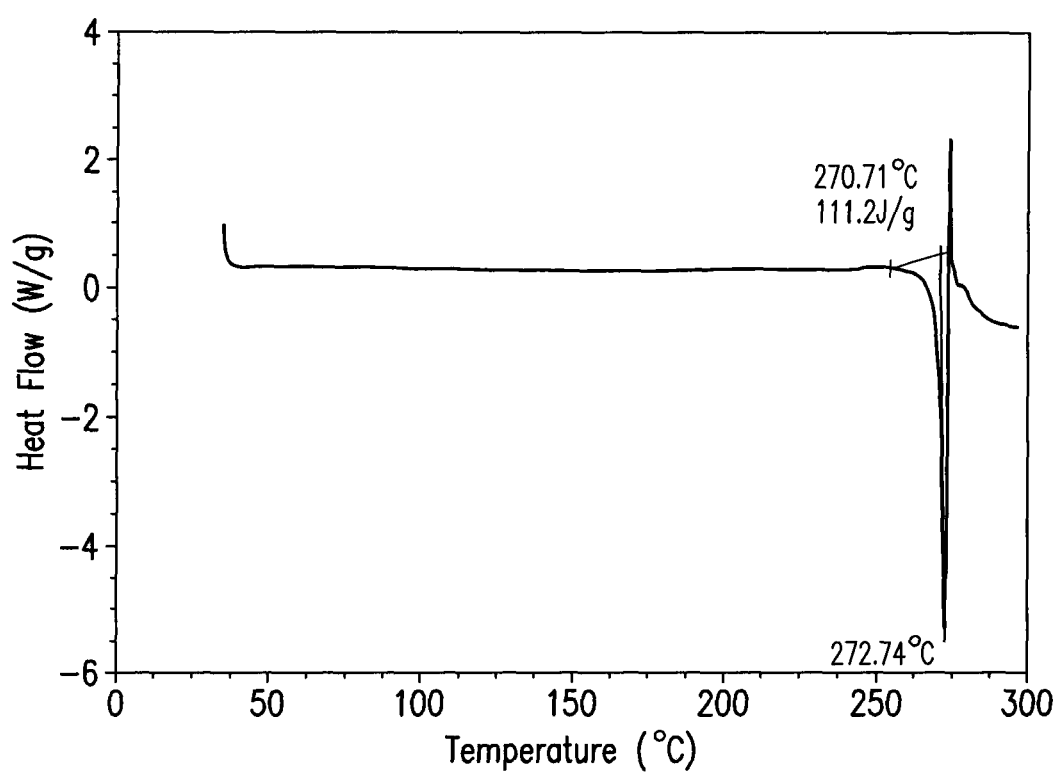

No solubility was observed for any salt in acetonitrile, acetone, dichloromethane, tetrahydrofuran or ethyl acetate. The isolated, recrystallized salts were analyzed by DSC as follows:

FIG. 1. shows a representative DSC thermogram of a besylate salt of Compound 6 recrystallized from ethanol FIG. 2. shows a representative DSC thermogram of a besylate salt of Compound 6 recrystallized from isopropanol.

Figure 3:
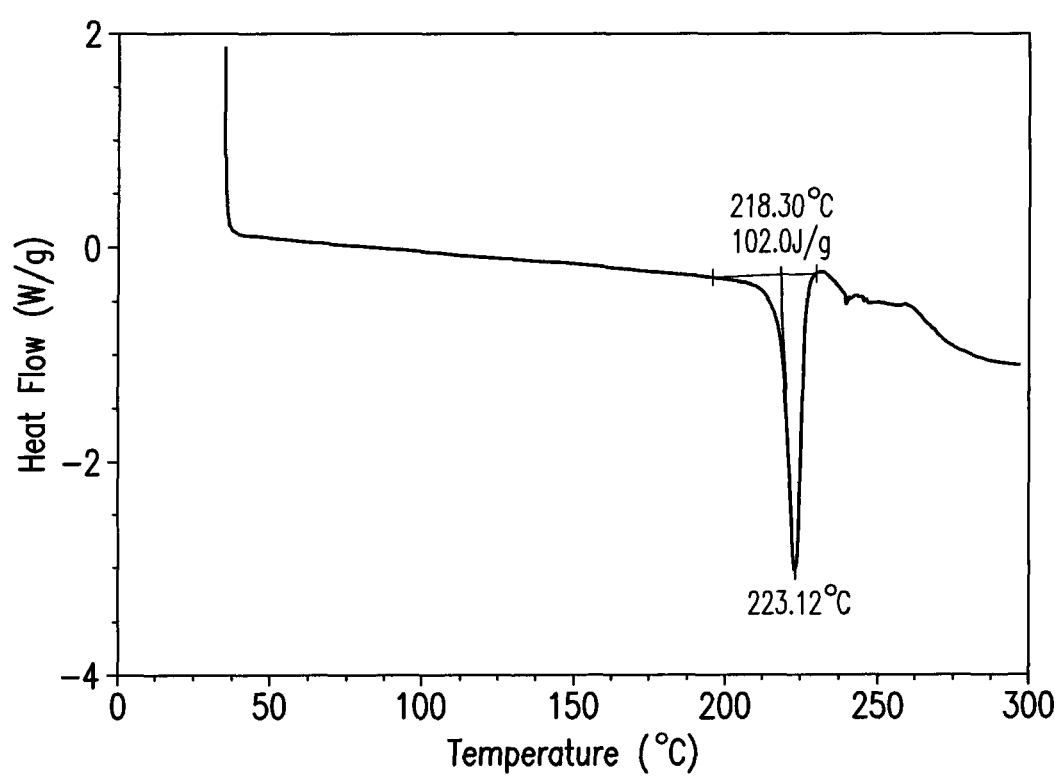

FIG. 3. shows a representative DSC thermogram of a esylate salt of Compound 6 recrystallized from ethanol.

Figure 4:
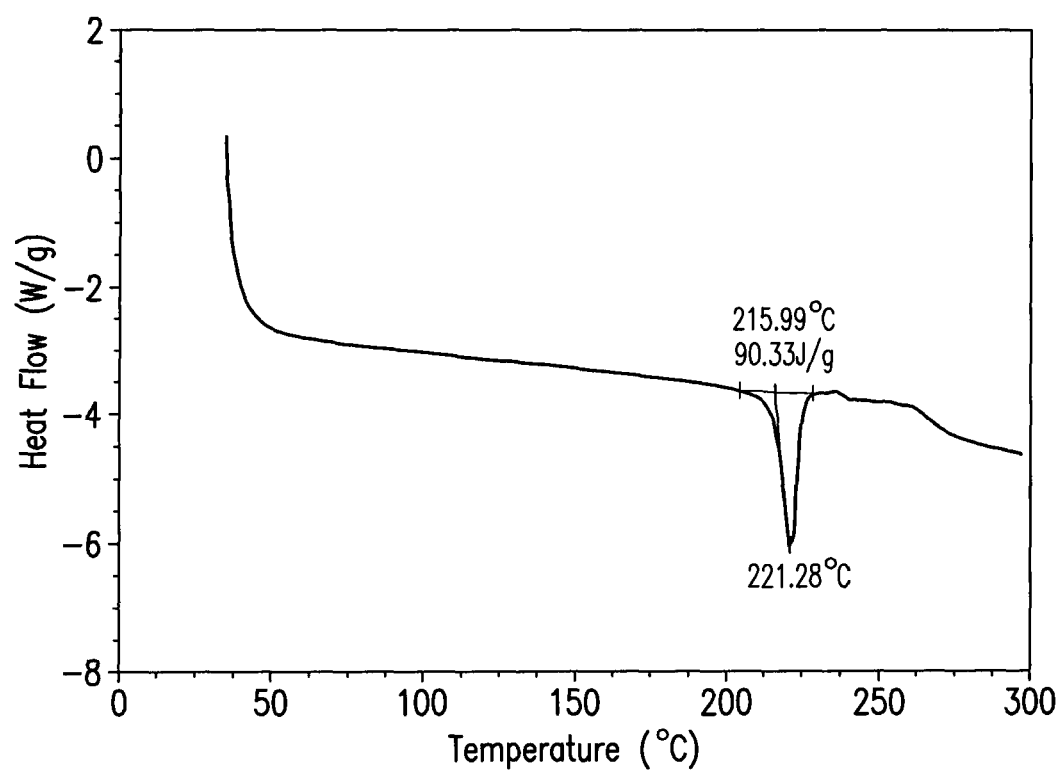

FIG. 4. shows a representative DSC thermogram of a esylate salt of Compound 6 recrystallized from isopropanol.

Figure 5:
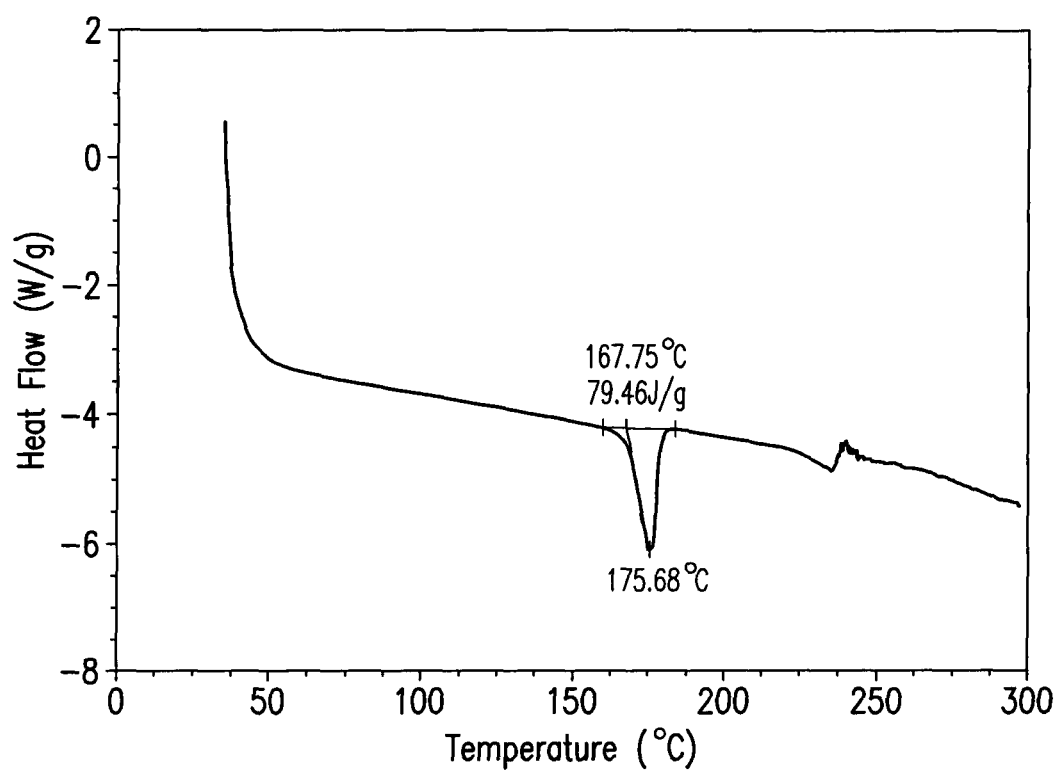

FIG. 5. shows a representative DSC thermogram of a HBr salt of Compound 6 recrystallized from water.

Figure 6:
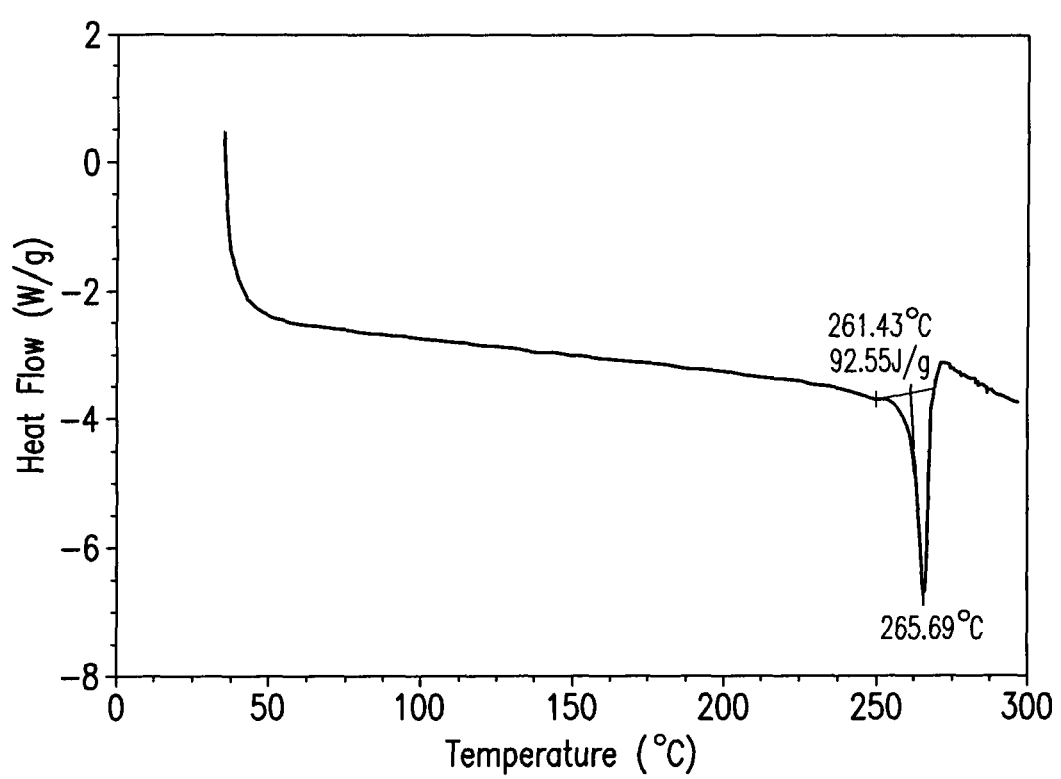

FIG. 6. shows a representative DSC thermogram of a HBr salt of Compound 6 recrystallized from ethanol.

Figure 7:
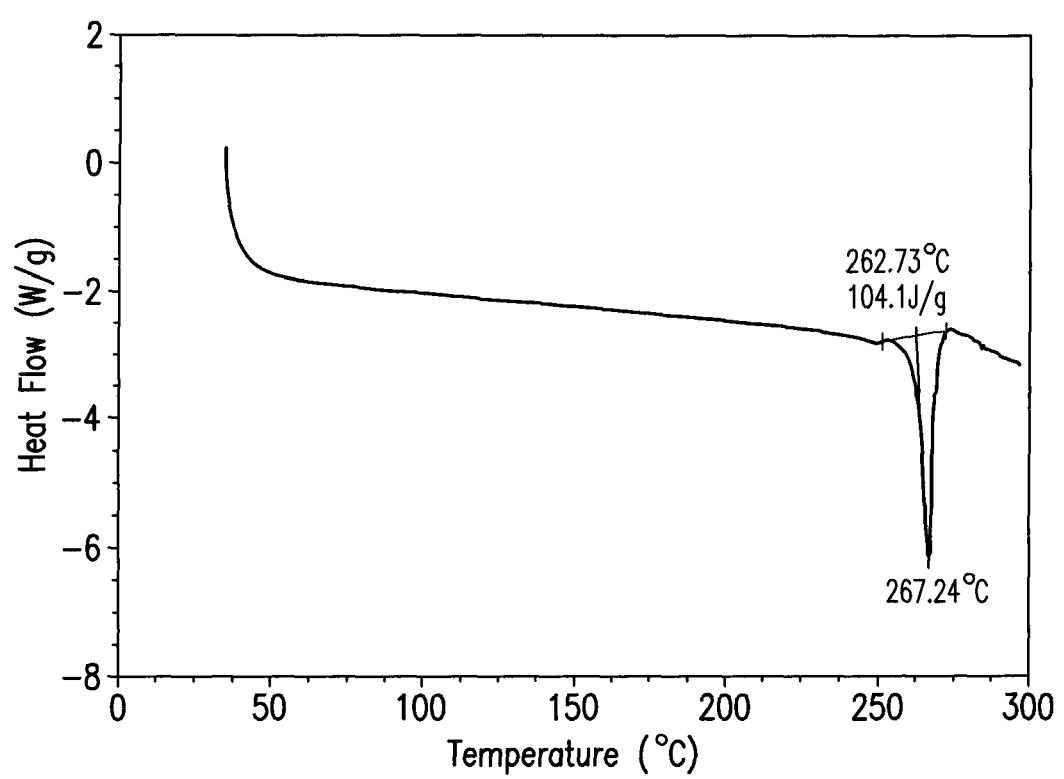

FIG. 7. shows a representative DSC thermogram of a HBr salt of Compound 6 recrystallized from isopropanol.

Figure 8:
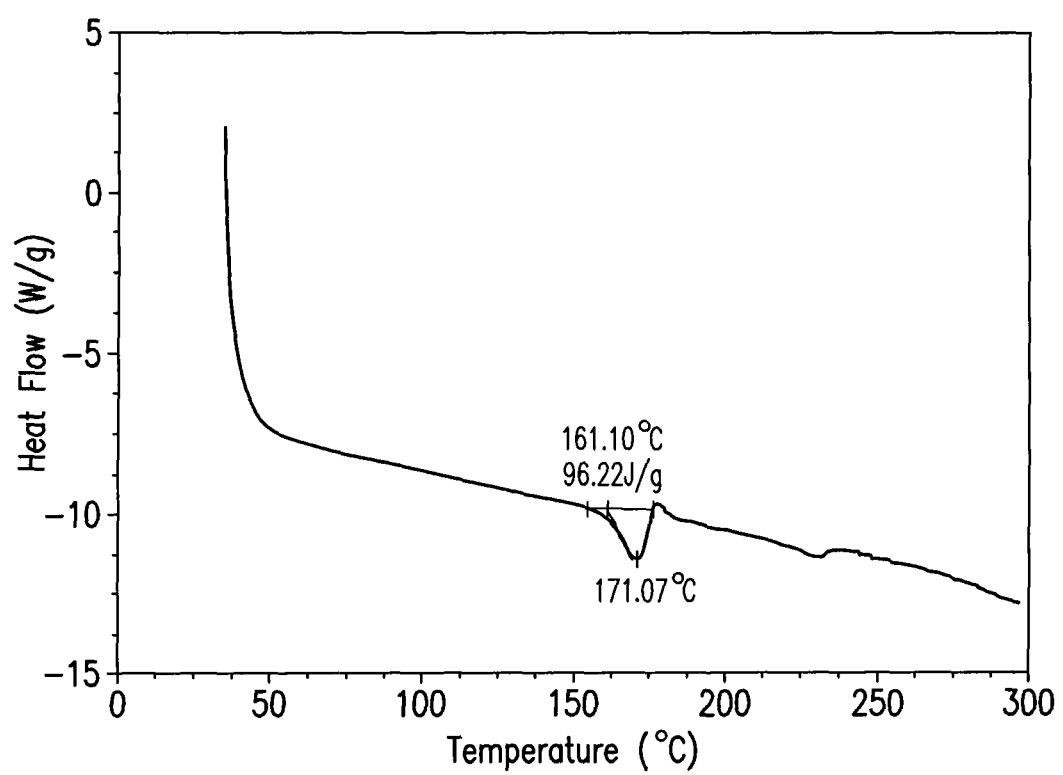

FIG. 8. shows a representative DSC thermogram of a HCl salt of Compound 6 recrystallized from water.

Figure 9:
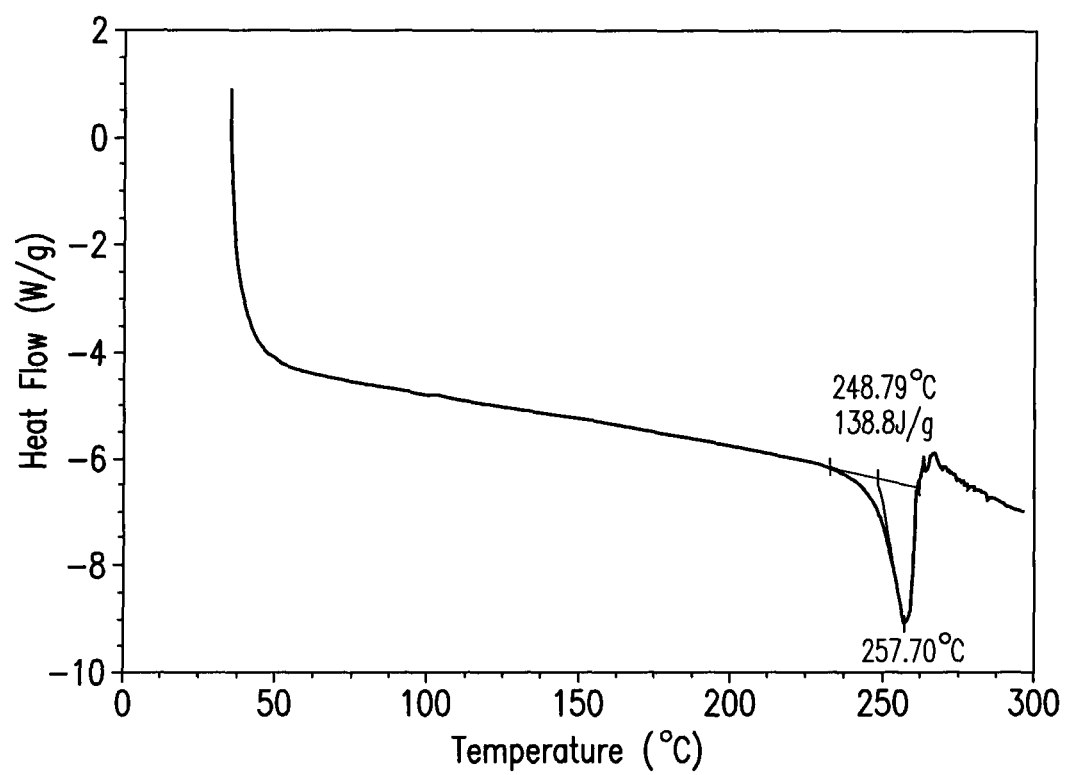

FIG. 9. shows a representative DSC thermogram of a HCl salt of Compound 6 recrystallized from ethanol.

Figure 10:
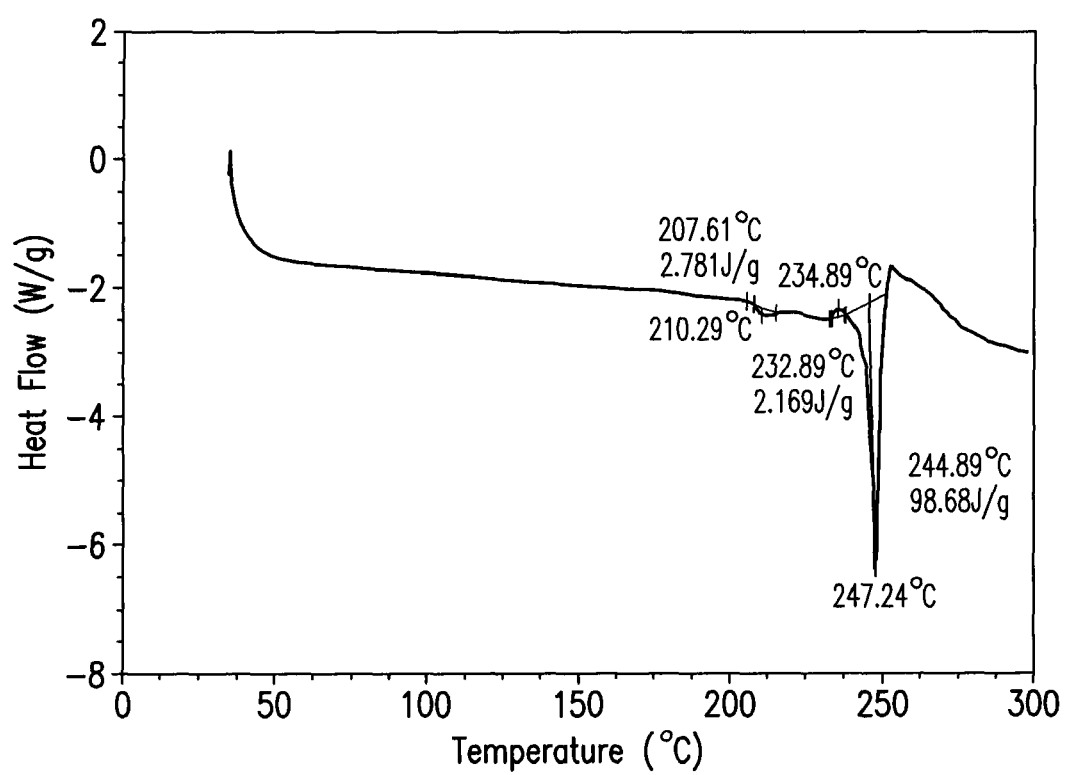

FIG. 10. shows a representative DSC thermogram of a mesylate salt of Compound 6 recrystallized from methanol.

Figure 11:
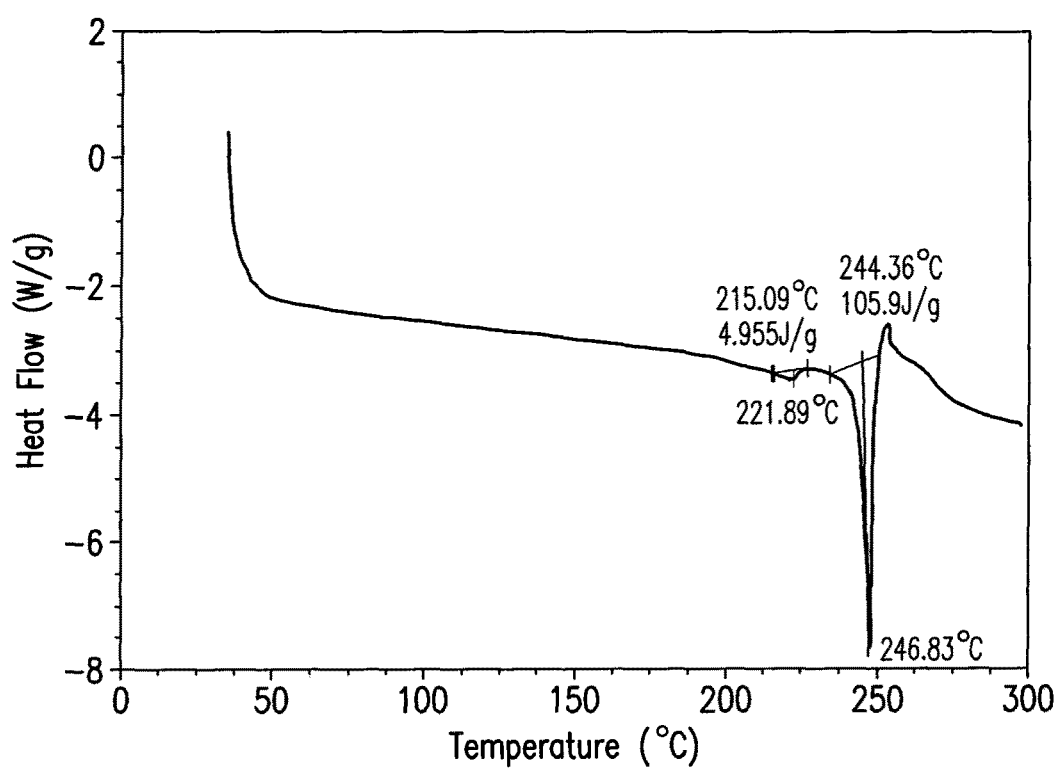
Figure 12:
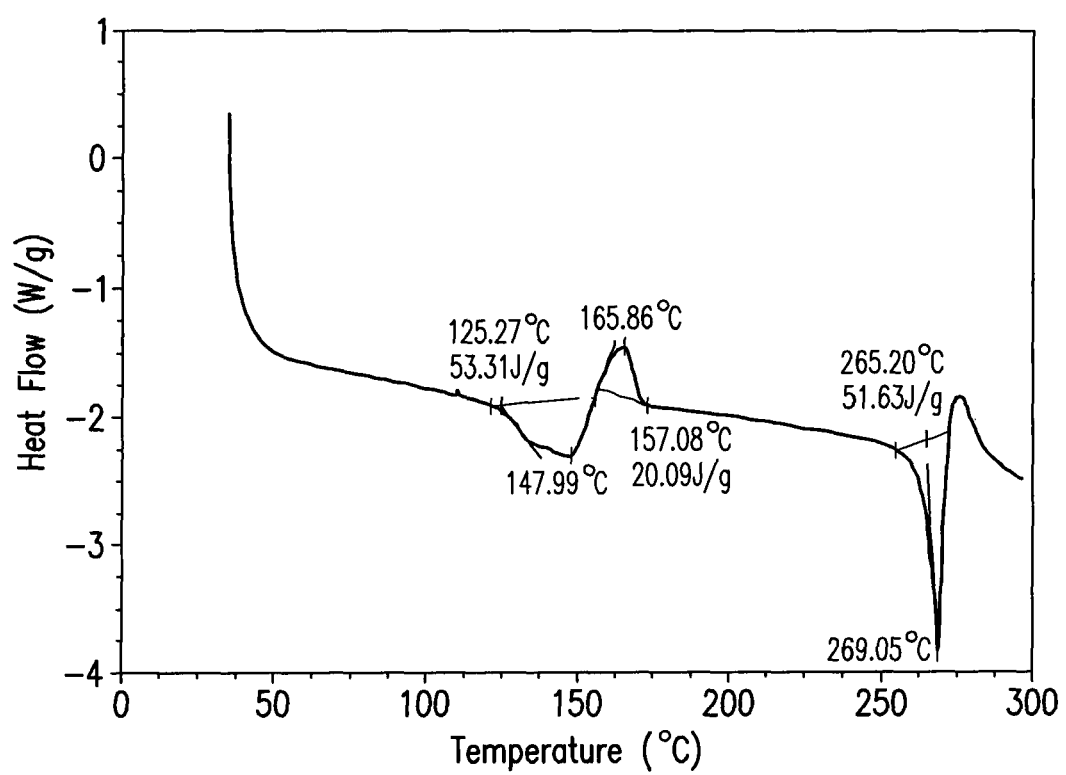

FIG. 11. shows a representative DSC thermogram of a mesylate salt of Compound 6 recrystallized from ethanol FIG. 12. shows a representative DSC thermogram of a tosylate salt of Compound 6 recrystallized from water.

Figure 13:
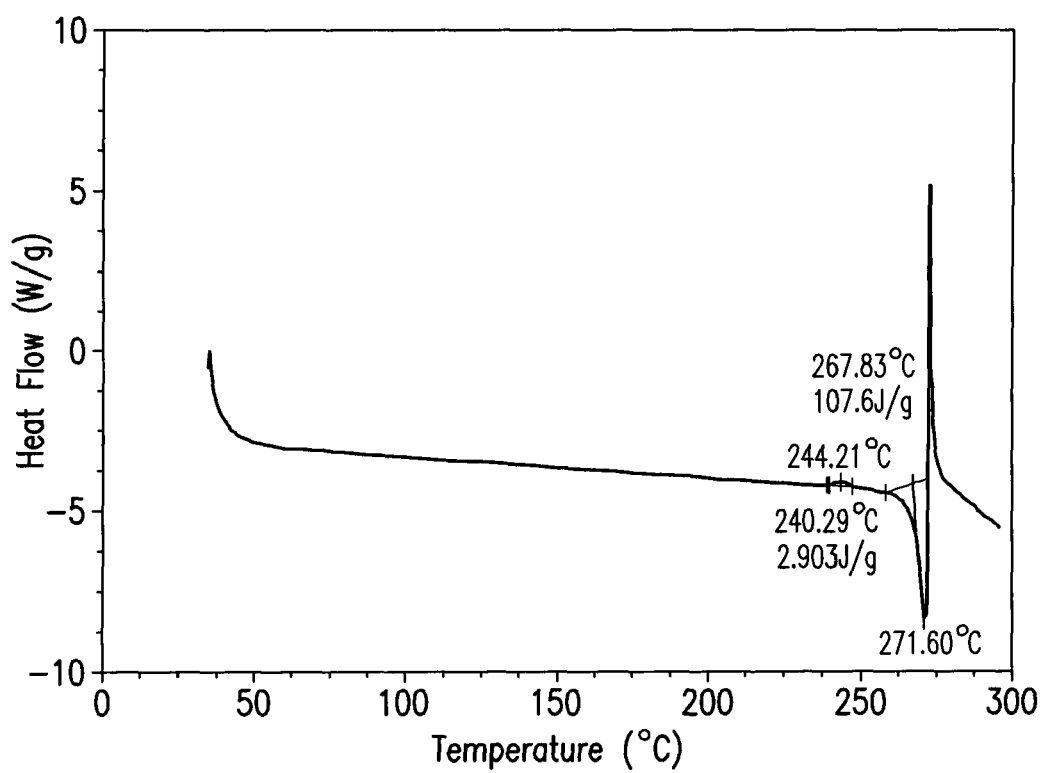

FIG. 13. shows a representative DSC thermogram of a tosylate salt of Compound 6 recrystallized from isopropanol.

7.5 Example 4

Preparation of Form A of Compound 6 Esylate Salt

Method A

To a 2-L Morton flask equipped with a heating mantle, thermocouple, condenser and mechanical stirrer was charged (4-fluorophenyl)(4-((5-methyl-1H-pyrazol-3-yl)amino)quinazolin-2-yl)methanol free base (40.20 g, 115 mmol, 1.0 equiv.). Ethanol (1.6 L) was added and the suspension was stirred and heated to reflux (78° C., internal temperature) until dissolution of the suspension was observed. Ethanesulfonic acid (9.4 mL, 115 mmol, 1.0 equiv.) was charged to the resulting yellow solution. Reflux was maintained for 1 hour, then heating was discontinued and the reaction was allowed to cool to room temperature and stirred overnight. Stirring was stopped and the solids were allowed to settle. The reaction was filtered and the initial isolated product (R)-(4-fluorophenyl)(4-((5-methyl-1H-pyrazol-3-yl)amino)quinazolin-2-yl)methanol dried in a vacuum oven (45° C., ~20 torr) for 3 days to produce 29.69 g, 65 mmol, 56% yield. The supernatant was concentrated and a second crop of the product was obtained and dried as the first to produce 10.52 g, 23 mmol, 20% yield.

The combined yield for the two crops was 76%. It was observed during this salt formation that the esylate salt has a higher solubility in ethanol compared to the free base. Higher yields of salt can be obtained by reducing the amount of ethanol. Following the above procedure, using 30.66 g (87.8 mmol) of (R)-(4-fluorophenyl)(4-((5-methyl-1H-pyrazol-3-yl)amino)quinazolin-2-yl)methanol, 300 mL of ethanol and 7.2 mL (87.8 mmol) of ethanesulfonic acid; 34.58 g, 75.3 mmol of salt was obtained. This was an 86% yield.

The characterization of the initial isolated product of the esylate salt of Compound 6 is summarized in Table 3:

TABLE 3

| Analysis | Result |
|---|---|
| XRPD[a] | crystalline A |
| TGA[b] | 0.03% weight loss up to 210° C. |
| $^1$H NMR | consistent with structure |
| DSC[b] | 223° C. (endo, peak; 218° C. onset; ΔH: 102 J/g) |

[a]High-resolution XRPD.
[b]Temperatures are rounded to the nearest ° C.; weight loss values are rounded to two decimal places; reported ΔH values are rounded to the nearest whole number.

Figure 14:
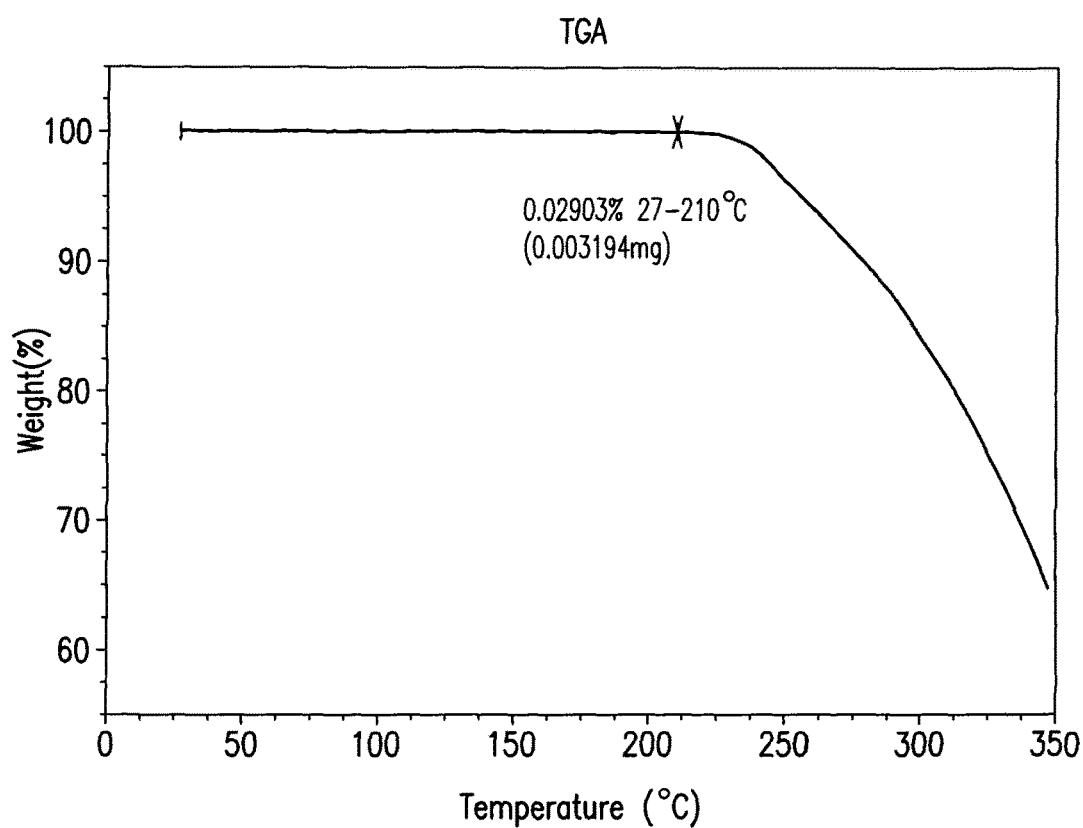
FIG. 14 shows a representative TGA thermogram of Form A of the esylate salt of Compound 6.
Figure 15:
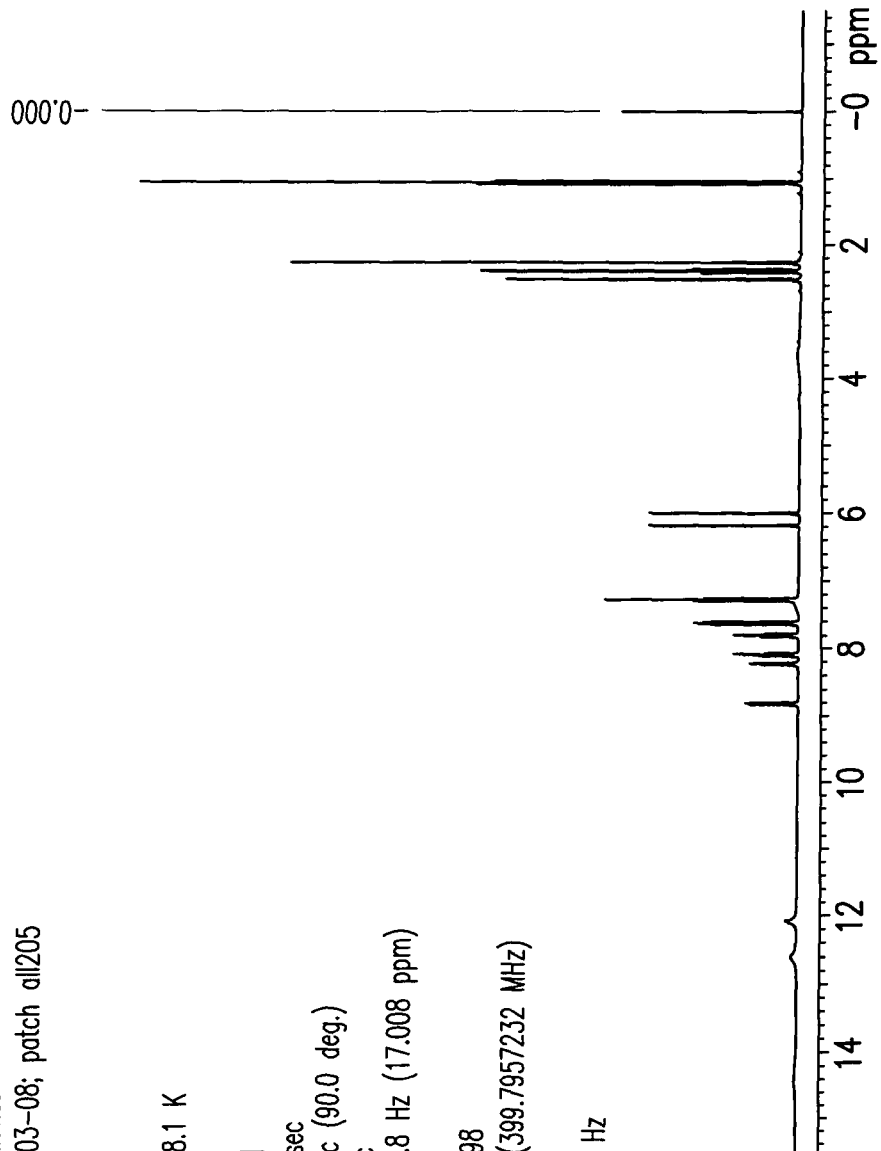
FIG. 15 shows a representative $^1$H NMR spectrum of Form A of the esylate salt of Compound 6.

By TGA (FIG. 14), a minimal weight loss of approximately 0.03% is observed up to 210° C., indicating the material is not solvated. The proton NMR spectrum of this ethanesulfonate salt of Compound 6 acquired for comparison with the new materials obtained during the polymorph screen was consistent with the esylate salt structure (FIG. 15).

Method B

In this study, the reaction parameters described in Method A were changed to improve the yield. The initial mass concentration was reduced to 10:1 solvent/(4-fluorophenyl)(4-((5-methyl-1H-pyrazol-3-yl)amino)quinazolin-2-yl) methanol free base ratio (instead of 32:1), and the cooling temperature was decreased to 0-5° C. from room temperature. The reaction time after the ethanesulfonic acid addition was reduced to 30 minutes. The stirring time at 0-5° C. was run for both 1 hour and for one night to simulate an eventual night break at a production plant.

In order to control precipitation at 78° C., between 4% to 6.4% DMSO with respect to (4-fluorophenyl)(4-((5-methyl-1H-pyrazol-3-yl)amino)quinazolin-2-yl)methanol free base was added. Na antisolvent, ethyl acetate was added during the coiling phase in order to dilute the reaction mass and to improve agitation. The yield improved to 72% in a single crop.

) In another study, the initial mass concentration was 20:1 solvent/(4-fluorophenyl)(4-((5-methyl-1H-pyrazol-3-yl)amino)quinazolin-2-yl)methanol free base ratio.

7.5.1.1 XRPD Data for Form A of the Esylate Salt of Compound 6

Initial isolated product of the esylate salt of Compound 6 exhibits a crystalline XRPD pattern designated as Form A, based on successful indexing (FIG. 17). The high-resolution XRPD pattern of this esylate salt of Compound 6 was indexed using X'Pert High Score Plus 2.2a (2.2.1). The indexed XRPD pattern of Form A material from Example 4 is illustrated in FIG. 17. Agreement between the allowed peak positions, marked with red bars, and the observed peaks indicates a consistent unit cell determination. Space groups consistent with the assigned extinction symbol, unit cell parameters, and derived quantities are tabulated below the figure. To confirm the tentative indexing solution, the molecular packing motifs within the crystallographic unit cells may be determined.

Peak positions were picked for XRPD pattern of Form A of the ethanesulfonate salt of Compound 6. Observed and representative peak lists are included. Peak picking was not performed under cGMP guidelines. One PANalytical pattern (file: 455424) and one INEL pattern (file: 456132) were analyzed for this material (FIG. 16), and therefore preferred orientation and particle statistic effects could be assessed through comparison of multiple patterns. Reproducibility between patterns indicates that the particle statistics are adequate. The relative peak intensities are in good agreement between XRPD patterns indicating good orientation statistics. Observed peaks are shown in FIG. 16 and representative peaks are listed in Tables 4 and 5.

TABLE 4

| °2θ | d space (Å) | Intensity (%) |
|---|---|---|
| 6.29 ± 0.20 | 14.041 ± 0.460 | 100 |
| 6.90 ± 0.20 | 12.802 ± 0.381 | 43 |
| 8.68 ± 0.20 | 10.192 ± 0.240 | 3 |
| 10.54 ± 0.20 | 8.394 ± 0.162 | 2 |
| 11.10 ± 0.20 | 7.972 ± 0.146 | 2 |
| 11.65 ± 0.20 | 7.596 ± 0.132 | 21 |
| 12.64 ± 0.20 | 7.005 ± 0.112 | 2 |
| 13.84 ± 0.20 | 6.399 ± 0.093 | 7 |
| 14.83 ± 0.20 | 5.975 ± 0.081 | 21 |
| 16.24 ± 0.20 | 5.459 ± 0.068 | 50 |
| 17.58 ± 0.20 | 5.046 ± 0.058 | 39 |
| 18.03 ± 0.20 | 4.921 ± 0.055 | 30 |
| 18.38 ± 0.20 | 4.828 ± 0.053 | 20 |
| 19.00 ± 0.20 | 4.672 ± 0.049 | 7 |
| 19.34 ± 0.20 | 4.590 ± 0.048 | 4 |
| 20.31 ± 0.20 | 4.373 ± 0.043 | 35 |
| 20.55 ± 0.20 | 4.322 ± 0.042 | 66 |
| 20.87 ± 0.20 | 4.257 ± 0.041 | 13 |
| 21.13 ± 0.20 | 4.204 ± 0.040 | 4 |
| 21.49 ± 0.20 | 4.136 ± 0.038 | 39 |

TABLE 4-continued

| °2θ | d space (Å) | Intensity (%) |
|---|---|---|
| 22.19 ± 0.20 | 4.007 ± 0.036 | 34 |
| 22.81 ± 0.20 | 3.898 ± 0.034 | 19 |
| 23.67 ± 0.20 | 3.760 ± 0.032 | 11 |
| 24.56 ± 0.20 | 3.625 ± 0.029 | 31 |
| 25.80 ± 0.20 | 3.454 ± 0.027 | 3 |
| 26.79 ± 0.20 | 3.328 ± 0.025 | 9 |
| 27.16 ± 0.20 | 3.283 ± 0.024 | 13 |
| 27.44 ± 0.20 | 3.250 ± 0.023 | 10 |
| 27.69 ± 0.20 | 3.222 ± 0.023 | 15 |
| 28.36 ± 0.20 | 3.147 ± 0.022 | 9 |
| 29.40 ± 0.20 | 3.038 ± 0.020 | 20 |

TABLE 5

| °2θ | d space (Å) | intensity (%) |
|---|---|---|
| 6.29 ± 0.20 | 14.041 ± 0.460 | 100 |
| 6.90 ± 0.20 | 12.802 ± 0.381 | 43 |
| 11.65 ± 0.20 | 7.596 ± 0.132 | 21 |
| 14.83 ± 0.20 | 5.975 ± 0.081 | 21 |
| 16.24 ± 0.20 | 5.459 ± 0.068 | 50 |
| 17.58 ± 0.20 | 5.046 ± 0.058 | 39 |
| 18.03 ± 0.20 | 4.921 ± 0.055 | 30 |
| 18.38 ± 0.20 | 4.828 ± 0.053 | 20 |
| 20.31 ± 0.20 | 4.373 ± 0.043 | 35 |
| 20.55 ± 0.20 | 4.322 ± 0.042 | 66 |
| 21.49 ± 0.20 | 4.136 ± 0.038 | 39 |
| 22.19 ± 0.20 | 4.007 ± 0.036 | 34 |

Therefore, Form A is a crystalline unsolvated material with a melting point at approximately 223° C.

7.5.1.2 Solubility Data for Form A of the Esylate Salt of Compound 6

Solubility of this Form A of the esylate salt of Compound 6 was estimated by solvent addition method to provide preliminary information for the polymorph screen in the next example. The material was freely soluble in dimethylformamide, hexafluoroisopropanol, and 2,2,2,-trifluoroethanol (>90 mg/mL), soluble in methanol (42 mg/mL), sparingly soluble in ethanol (9 mg/mL), and slightly soluble in 1-propanol and isopropanol (1-2 mg/mL). Solubility of this Form A of the esylate salt of Compound 6 was also estimated in various solvent mixtures, as summarized in Table 6.

TABLE 6

| Solvent | Solubility (mg/mL)[a] |
|---|---|
| Acetone | <1 |
| acetonitrile (ACN) | <1 |
| t-butanol | <1 |
| Chloroform | <1 |
| dichloromethane (DCM) | <1 |
| Dioxane | <1 |
| dimethylformamide (DMF) | >90 |
| ethanol (EtOH) | 9 |
| ethyl acetate (EtOAc) | <1 |
| Heptanes | <1 |
| hexafluoroisopropanol (HFIPA) | >100 |
| Hexanes | <1 |
| isopropanol (IPA) | 1 |
| isopropyl acetate (i-PrOAc) | <1 |
| isopropyl ether (IPE) | <1 |
| methanol (MeOH) | 42 |
| methyl ethyl ketone (MEK) | <1 |
| methyl isobutyl ketone (MIBK) | <1 |
| 1-propanol | 2 |
| 2,2,2,-trifluoroethanol (TFE) | >100 |
| tetrahydrofuran (THF) | <1 |
| Toluene | <1 |
| Water | <1 |
| dioxane: water (1:1) | >78 |
| MeOH: acetone (1:4) | 5 |
| MeOH: ACN (1:4) | 6 |
| MeOH: chloroform (1:4) | 18 |
| MeOH: DCM (1:4) | >38 |
| MeOH: DCM (1:9) | 10 |
| MeOH: EtOAc (1:4) | 3 |
| MeOH: IPA (1:4) | 4 |
| MeOH: IPE (1:4) | <2 |
| MeOH: IPE (1:1) | 8 |
| MeOH: THF (1:4) | 5 |
| MeOH: toluene (1:4) | 7 |
| MeOH: water (1:4) | <2 |
| MeOH: water (1:2) | 9 |
| MeOH: water (1:1) | >40 |

[a]Solubilities are calculated based on the total solvent used to give a solution; actual solubilities may be greater because of the volume of the solvent portions utilized or a slow rate of dissolution. Solubilities are rounded to the nearest mg/mL.

7.6 Example 5

Polymorph Screen of Esylate Salt of Compound 6

An polymorph screen was conducted using the Form A of the esylate salt of Compound 6 prepared in Example 4 as the starting material with results shown below in Tables 7A and 7B.

TABLE 7A

| Solvent | Method | Observations | XRPD Result |
|---|---|---|---|
| DMF | FE/7 d, FE in a N₂ box/11 d | yellow solids, irregular, B/E | D |
| EtOH | FE | light-yellow solids, irregular, B/E | A |
| | slurry/RT/7 d | white solids, irregular, B/E | A |
| | SC (70° C. to RT, refrigerator/1 d, freezer/5 d)[a] | no solids | C |
| | equilibrated to RT, IPE addition | light-yellow solids, irregular B/E | |
| | CC (70° C. to dry ice/IPA, freezer/ 7 d)[a] | no solids | C + A |
| | equilibrated to RT, hexanes addition | light-yellow solids, irregular, B/E | |
| HFIPA | SE | yellow solids, irregular, B/E | likely amorphous |
| IPA | slurry/RT/7 d | white solids, irregular, B/E | A |
| | SC (70° C. to RT, refrigerator/1 d, freezer/5 d)[a] | no solids | A |
| | equilibrated to RT, FE | yellow solids, aggregates, no B | |
| MeOH | SE | light-yellow solids, irregular, B/E | A |

TABLE 7A-continued

| Solvent | Method | Observations | XRPD Result |
|---|---|---|---|
| l-propanol | FE | light-yellow solids, irregular, B/E | A |
| | slurry/RT/7 d | white solids, irregular, B/E | A |
| | SC (70° C. to RT, refrigerator/1 d, freezer/5 d)$^a$ | no solids | C |
| | equilibrated to RT, IPE addition | light-yellow solids, irregular, B/E | C + A |
| | SC (70° C. to RT, ice/IPA, freezer/ 7 d)$^a$ | no solids | |
| | equilibrated to RT, hexanes addition | light-yellow solids, irregular, B/E | |
| TFE | SE | light-yellow solids, irregular, B/E | B |

TABLE 7B

| Solvent | Method | Observations | XRPD Result |
|---|---|---|---|
| dioxane:water (1:1) | FE | yellow solids, irregular and some plates, B/E, extinction is not uniform | disordered |
| HFIPA:acetone (1:2) | SE | light-yellow solids, irregular, B/E | A |
| HFIPA:chloroform (1:2) | SE | yellow solids, irregular, B/E | likely amorphous |
| HFIPA:DCM (1:2) | SE | yellow solids, irregular, B/E | likely amorphous |
| HFIPA:IPE (1:2) | precipitation with IPE addition | light-yellow solids, irregular, B/E | A |
| HFIPA:THF (1:2) | SE | light-yellow solids, irregular, B/E | A |
| MeOH:acetone (1:1) | SE | light-yellow solids, irregular, B/E | A |
| MeOH:chloroform (1:1) | SE | light-yellow solids, irregular, B/E | A |
| MeOH:chloroform (1:4) | SE | light-yellow solids, irregular, B/E | A + B |
| MeOH:DCM (1:1) | SE | light-yellow solids, irregular, B/E | A |
| MeOH:DCM (1:4) | SE | light-yellow solids, irregular, B/E | A |
| MeOH:IPE (1:1) | SE | light-yellow solids, irregular, B/E | A |
| MeOH:THF (1:1) | SE | light-yellow solids, irregular, B/E | A + B |
| MeOH:toluene (1:4) | slurry/RT/7 d | white solids, irregular, B/E | A |
| MeOH:water (1:1) | SE | yellow solids, irregular, B/E | disordered |
| MeOH:water (1:2) | slurry/RT/7 d | yellow solids, irregular, B/E | A + possible disordered/ amorphous content |

TABLE 7B-continued

| Solvent | Method | Observations | XRPD Result |
|---|---|---|---|
| TFE:ACN (1:1) | SE | light-yellow solids, irregular, B/E | A |
| TFE:EtOAc (1:1) | SE | light-yellow solids, irregular, B/E | A |
| TFE:IPA (1:1) | SE | light-yellow solids, irregular, B/E | A |
| TFE:IPE (1:1) | precipitation with IPE addition | light-yellow solids, irregular, B/E | C + A |
| TFE:MEK (1:1) | SE | light-yellow solids, irregular, B/E | A |

TABLE 7B

| Solvent | Antisolvent | Conditions | Observations | XRPD Result |
|---|---|---|---|---|
| DMF | ACN | VD/RT/17 d ACN addition | no solids off-white solids, irregular, B/E | C + A |
| | chloroform | VD/RT/17 d chloroform addition | no solids no solids | — |
| | IPA | VD/RT/17 d IPA addition | no solids no solids | — |
| EtOH | acetone | VD/RT/7 d | white solids, irregular, B/E | A |
| | hexanes | VD/RT/7 d | white solids, irregular, B/E | A |
| | THF | VD/RT/7 d | white solids, irregular, B/E | A |
| | toluene | VD/RT/16 d | white solids, aggregates, no B | A |
| MeOH | DCM | VD/RT/17 d DCM addition | no solids no solids | — |
| | dioxane | VD/RT/7 d | light-yellow solids, irregular, B/E | A |
| | EtOAc | VD/RT/7 d | white solids, irregular, B/E | A |
| | IPE | VD/RT/7 d | white solids, irregular, B/E | A |

Additional polymorph screen experiments were conducted using amorphous esylate salt of Compound 6 generated by rotary evaporation of a hexafluoroisopropanol solution (Table 8). A variety of crystallization techniques were utilized and included evaporation (fast, slow and rotary evaporation), cooling (slow and crash cooling), solvent/ antisolvent precipitation, slurry, milling, vapor stress, and vapor diffusion.

TABLE 8

| Solvent | Method | Observations | XRPD Result |
|---|---|---|---|
| acetone | spontaneous precipitation | white solids, ageregates, no B | A + C |
| ACN | spontaneous precipitation | white solids, aggregates, no B | A |
| dioxane | VS/RT/7 d | light-yellow solids, irregular, B/E | A |

TABLE 8-continued

| Solvent | Method | Observations | XRPD Result |
|---|---|---|---|
| — | 75% RH/RT/7 d | light-yellow solids, irregular, B/E | B |
| EtOH | spontaneous precipitation at 70° C.[a] | light-yellow solids, aggregates, no B | A |
| water | spontaneous precipitation | light-yellow solids, irregular, B/E | similar to free base (slight peak shifts) |
| water | FE | insufficient solids | — |
| EtOH: heptane (1:2) | precipitation with heptane addition | white solids, aggregates, no B | A + C |
| EtOH: MIBK (1:2) | precipitation with MIBK addition | white solids, aggregates, no B | A + C |
| EtOH: water (1:1) | VSRT/7 d | light-yellow solids, irregular, B/E | A |
| EtOH: water (1:10) | precipitation with water addition | white solids, irregular, B/E | free base |
| EtOH: water (1:20) | precipitation with water addition | light-yellow solids, irregular, B/E | free base |
| EtOH: water (1:20) | partial FE | light-yellow solids, irregular, B/E | free base |

Figure 18:
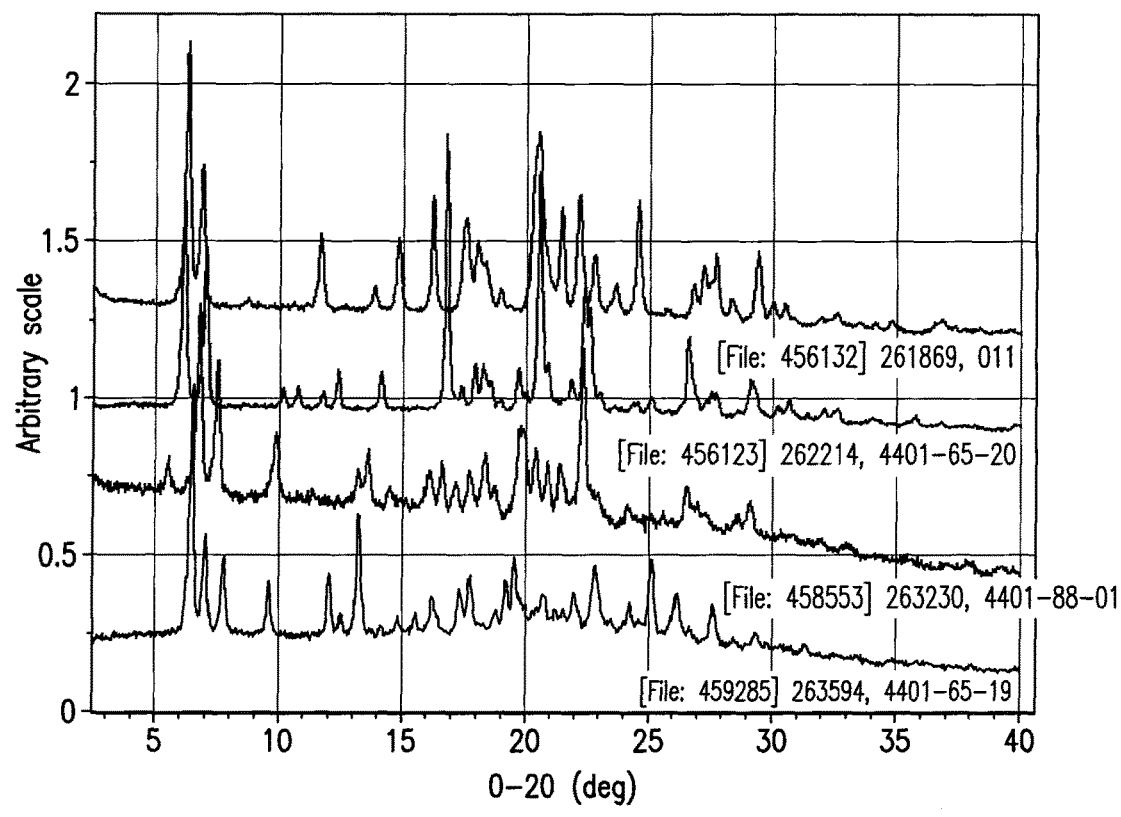
FIG. 18 shows representative XRPD patterns, from top to bottom, of (i) Form A of the esylate salt of Compound 6 (ii)

Crystalline materials exhibiting XRPD pattern A were produced from the majority of experiments. Three new crystalline materials consistent with the esylate salt by proton NMR spectroscopy were identified in the course of the polymorph screen and designated as Form B, Form C, and material D. FIG. 18 shows an overlay of the four crystalline patterns obtained for the esylate salt of Compound 6 (from top to bottom: (i) Form A from Example 4, (ii) Form B, obtained from slow evaporation in TFE, (iii) Form C, obtained from precipitation from EtOH with IPE and (iv) Form D, obtained from fast evaporation in DMF).

7.6.1 Additional Solid Forms Comprising the Esylate Salt of Compound 6

Also obtained from the polymorph screen conducted using Form A of the esylate salt of Compound 6 were material exhibiting a disordered crystalline XRPD pattern resulting from evaporation in 1:1 dioxane: water (top pattern, FIG. 19. Some plates were observed in this sample by polarized light microscopy; however, the crystals were not suitable for single crystal x-ray analysis (extinction was not uniform). Another disordered XRPD pattern was observed from evaporation in 1:1 MeOH: water (bottom pattern, FIG. 19). Possible amorphous materials were obtained from evaporation experiments using hexafluoroisopropanol by slow evaporation in HFIPA (top pattern, FIG. 20), slow evaporation in 1:2 HFIPA: DCM (middle pattern, FIG. 20) and slow evaporation in 1:2 HFIPA: chloroform (bottom pattern, FIG. 20).

7.6.2 Amorphous Esylate Salt of Compound 6

Attempts to prepare amorphous ethanesulfonate salt of Compound 6 were performed by milling, lyophilization, and rotary evaporation (Table 9 below). An overlay of XRPD patterns for amorphous attempts is shown in FIG. 21 compared to the Form A pattern obtained from the crystalline product in Example 4 (bottom pattern of FIG. 21). Form A (possibly disordered) was recovered from the milling experiment (third pattern from top, FIG. 21); the material prepared by lyophilization in 1:1 dioxane: water exhibited mostly x-ray amorphous pattern with broad peaks at approximately 8.2 and 20.1 °2θ (second pattern from top, FIG. 21). X-ray amorphous material was obtained from rotary evaporation in hexafluoroisopropanol (top pattern in FIG. 21).

TABLE 9

| Conditions | Observations | Analysis | Results |
|---|---|---|---|
| freeze-drying in dioxane: water (1:1)/3 d | yellow solids, aggregates, no B | XRPD | mostly x-ray amorphous with broad peaks at ~8.2, 20.1 °2θ |
| milling/30 Hz, 3 × 10 min | light-yellow solids, aggregates, partial B | XRPD | disordered A |
| rotary evaporation in HFIPA | yellow solids, aggregates, no B | XRPD mDSC[a] | x-ray amorphous 20° C. ($T_g$, midpoint), 0.31 J/g · ° C. ($\Delta C_p$); 212° C. (endo, peak) |
| | yellow solids, aggregates, no B | XRPD | x-ray amorphous |

Approximate solubility data of x-ray amorphous ethanesulfonate salt of Compound 6 are summarized in Table 10 below. As noted during the solubility assessment, initial dissolution was observed upon solvent addition and was followed by immediate precipitation in each solvent tested except in ethanol.

TABLE 10

| Solvent | Solubility (mg/mL)[a] |
|---|---|
| acetone | >72 [b] |
| acetonitrile (ACN) | >66 [b] |
| chloroform | >68 [b] |
| dichloromethane (DCM) | >65 [b] |
| ethanol (EtOH) | >70 |
| ethyl acetate (EtOAc) | >66 [b] |
| isopropanol (IPA) | >76 [b] |
| methyl ethyl ketone (MEK) | >76 [b] |
| tetrahydrofuran (THF) | >80 [b] |
| toluene | >69 [b] |
| water | 26 [c] |

[a]Solubilities are calculated based on the total solvent used to give a solution; actual solubilities may be greater because of the volume of the solvent portions utilized or a slow rate of dissolution. Solubilities are rounded to the nearest mg/mL.
[b] Solids went into solution after the first aliquot of solvent; however, precipitation was observed immediately afterwards.
[c] Solids went into solution with water addition; however, precipitation was observed immediately afterwards.

Amorphous ethanesulfonate salt of Compound 6 showed greater solubility in water (26 mg/mL) and ethanol (>70 mg/mL) when compared with crystalline Form A from Example 4. Spontaneous precipitation from the aqueous solution afforded Compound 6 as free base; a new crystalline XRPD pattern was observed (See FIG. 38). The free base of Compound 6 was partially precipitated upon water addition to the ethanol solution and was further recovered by evaporation of the ethanol: water solution. These observations indicate the esylate salt is unstable in water and aqueous ethanol due to dissociation.

Modulated DSC thermogram for x-ray amorphous ethanesulfonate salt of Compound 6 is shown in FIG. 22. One apparent glass transition temperature ($T_g$) is observed as a step change in the reversing heat flow signal at approximately 20° C. (midpoint) with a change in the heat capacity ($\Delta C_p$) of 0.31 J/(g ° C.). An endotherm observed at approximately 212° C. (peak) likely indicates crystallization of the amorphous solid upon heating above $T_g$ where the endotherm at 212° C. may be attributed to melting of crystalline material.

7.6.3 Characterization of Form B of Esylate Salt of Compound 6

Form B of the esylate salt of Compound 6 was obtained from evaporation in TFE and alternatively by stressing amorphous ethanesulfonate salt of Compound 6 at 75% RH/RT for approximately 7 days. Materials exhibiting XRPD pattern A with B peaks resulted from evaporation in 1:1 MeOH: THF and 1:4 MeOH: chloroform mixtures (FIG. 23, from top to bottom: (i) A+B from slow evaporation in 1:1 MeOH: THF, (ii) A+B from slow evaporation in 1:4 MeOH: chloroform, (iii), as prepared in Example 4, (iv) B from slow evaporation in TFE). Form B was successfully prepared on a 300-mg scale by evaporation in TFE as described in Table 11. FIG. 24 shows the XRPD pattern obtained for Form B (from top to bottom: (i) B from slow evaporation in TFE, screen attempt, (ii) B from slow evaporation in TFE, scale-up attempt, data acquired on Inel and (iii) B from slow evaporation in TFE, scale-up attempt, data acquired on PANalytical).

TABLE 11

| Attempted material | Solvent | Method | Observations | XRPD Result |
|---|---|---|---|---|
| B | TFE | SE | light-yellow solids, irregular, B/E | B |
| C | EtOH[b] | IPE addition | light-yellow solids, irregular, B/E | A |
|  | EtOH[c] | SC (70° C. to RT, refrigerator/3 d)[a] | no solids | C + A |
|  |  | equilibrated to RT, IPE addition | light-yellow solids, irregular, B/E |  |
|  | EtOH[d] | IPE addition | light-yellow solids, irregular, B/E | C |

[a]The temperature is approximate.
[b]Concentration of ethanol solution: 9 mg/mL; stirring was applied for ~30 min after precipitation occurred and before the solid was filtered.
[c]Concentration of ethanol solution: 16 mg/mL; stirring was stopped after precipitation was observed.
[d]Concentration of ethanol solution; 16 mg/mL; amorphous material was used; no stirring was applied.

The high-resolution XRPD pattern of the ethanesulfonate salt of Compound 6 Form B was successfully indexed using X'Pert High Score Plus 2.2a (2.2.1), as illustrated in FIG. 25. Agreement between the allowed peak positions, marked with red bars, and the observed peaks indicates a consistent unit cell determination. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing were performed.

Peak positions were picked for XRPD pattern of the ethanesulfonate salt of Compound 6, Form B. One PANalytical pattern and one INEL pattern were analyzed for this material, and therefore preferred orientation and particle statistic effects could be assessed through comparison of multiple patterns. Reproducibility between patterns indicates that the particle statistics are adequate. The relative peak intensities are in good agreement between XRPD patterns indicating good orientation statistics. Observed peaks are summarized in Table 12A below, and representative peaks are listed in Table 12B.

TABLE 12A

| °2θ | d space (Å) | intensity (%) |
|---|---|---|
| 6.17 ± 0.20 | 14.320 ± 0.479 | 97 |
| 7.06 ± 0.20 | 12.525 ± 0.365 | 69 |
| 8.70 ± 0.20 | 10.169 ± 0.239 | 1 |
| 10.15 ± 0.20 | 8.716 ± 0.175 | 8 |
| 10.73 ± 0.20 | 8.242 ± 0.156 | 10 |
| 11.74 ± 0.20 | 7.540 ± 0.130 | 6 |
| 12.37 ± 0.20 | 7.154 ± 0.117 | 15 |
| 14.14 ± 0.20 | 6.262 ± 0.089 | 15 |
| 15.66 ± 0.20 | 5.657 ± 0.073 | 1 |
| 16.82 ± 0.20 | 5.272 ± 0.063 | 100 |
| 17.17 ± 0.20 | 5.165 ± 0.060 | 2 |
| 17.44 ± 0.20 | 5.086 ± 0.059 | 9 |
| 17.92 ± 0.20 | 4.950 ± 0.055 | 16 |
| 18.25 ± 0.20 | 4.860 ± 0.053 | 13 |
| 18.42 ± 0.20 | 4.816 ± 0.052 | 7 |
| 18.61 ± 0.20 | 4.769 ± 0.051 | 9 |
| 18.96 ± 0.20 | 4.682 ± 0.049 | 4 |
| 19.67 ± 0.20 | 4.512 ± 0.046 | 15 |
| 19.99 ± 0.20 | 4.441 ± 0.044 | 5 |
| 20.56 ± 0.20 | 4.320 ± 0.042 | 78 |
| 20.93 ± 0.20 | 4.245 ± 0.041 | 14 |
| 21.30 ± 0.20 | 4.172 ± 0.039 | 2 |
| 21.60 ± 0.20 | 4.115 ± 0.038 | 3 |
| 21.90 ± 0.20 | 4.059 ± 0.037 | 12 |
| 22.40 ± 0.20 | 3.969 ± 0.035 | 43 |
| 22.63 ± 0.20 | 3.929 ± 0.035 | 29 |
| 23.03 ± 0.20 | 3.861 ± 0.033 | 7 |
| 23.64 ± 0.20 | 3.764 ± 0.032 | 2 |
| 23.89 ± 0.20 | 3.725 ± 0.031 | 1 |
| 24.32 ± 0.20 | 3.660 ± 0.030 | 2 |
| 24.49 ± 0.20 | 3.635 ± 0.029 | 2 |
| 25.06 ± 0.20 | 3.554 ± 0.028 | 5 |
| 25.84 ± 0.20 | 3.448 ± 0.026 | 1 |
| 26.31 ± 0.20 | 3.388 ± 0.025 | 3 |
| 26.59 ± 0.20 | 3.352 ± 0.025 | 26 |
| 27.24 ± 0.20 | 3.273 ± 0.024 | 4 |
| 27.50 ± 0.20 | 3.244 ± 0.023 | 8 |
| 27.75 ± 0.20 | 3.215 ± 0.023 | 6 |
| 28.65 ± 0.20 | 3.116 ± 0.021 | 2 |
| 29.13 ± 0.20 | 3.065 ± 0.021 | 10 |

TABLE 12B

| °2θ | d space (Å) | Intensity (%) |
|---|---|---|
| 6.17 ± 0.20 | 14.320 ± 0.479 | 97 |
| 7.06 ± 0.20 | 12.525 ± 0.365 | 69 |
| 12.37 ± 0.20 | 7.154 ± 0.117 | 15 |
| 14.14 ± 0.20 | 6.262 ± 0.089 | 15 |
| 16.82 ± 0.20 | 5.272 ± 0.063 | 100 |
| 20.56 ± 0.20 | 4.320 ± 0.042 | 78 |
| 22.40 ± 0.20 | 3.969 ± 0.035 | 43 |
| 22.63 ± 0.20 | 3.929 ± 0.035 | 29 |

Characterization data for Form B are summarized in Table 13 below. The thermal analysis results for Form B are shown in FIG. 26. By TGA, Form B exhibits approximately 4.0% weight loss up to 150° C., indicating loss of volatiles upon heating. This percentage corresponds to approximately 0.8 moles of water, assuming the total weight loss is attributed to water loss. Form B was found to contain approximately 3.57% or 0.7 moles of water by Karl-Fischer analysis (Table 13 below), which is consistent with the value estimated from TGA. The dramatic change in the slope of the TGA thermogram at approximately 244° C. is consistent with decomposition. Four endotherms are observed by DSC at approximately 98, 136, 222, and 236° C. The first two endotherms are probably associated with dehydration, while the last endotherm may be due to initial decomposition. The endotherm is at approximately 222° C. which is similar to the melting endotherm of Form A, which may indicate conversion to A upon heating. Variable temperature XRPD analysis may be performed to confirm this assumption.

Hot-stage microscopy (HSM) was conducted for Form B, both dry and under silicon oil to confirm possible desolvation and melting endotherms in DSC. Three liquefaction events were noted at approximately 144, 213, and 221° C. No apparent desolvation (dehydration) was observed when the sample was analyzed under silicon oil.

The proton NMR spectrum acquired on Form B was consistent with the ethanesulfonate salt (FIG. 27).

TABLE 13

| Analysis | Result |
|---|---|
| XRPD | B |
| DSC[b] | 98° C. (endo, peak); 136° C. (endo, peak); 217° C. (endo, shoulder); 222° C. (endo, peak); 236° C. (endo, peak) |
| TGA[b] | 4.0% weight loss up to 150° C. (0.8 moles of water); 244° C. (onset, decomposition) |
| HSM[b,d] | 24° C., fine particulates, B/E; started heating at 10° C./min<br>80° C., no change<br>100° C., no change<br>137° C., increasing B/E<br>144° C., smaller particles melted<br>163° C., recrystallization in larger particles (started at ~150° C.)<br>177° C., smaller particles consist of glass and B/E<br>191° C., darkening of particles<br>198° C., continued loss of birefringence<br>213° C., small particles melted<br>219° C., recrystallization in melt of smaller particles<br>221° C., large particles melted<br>224° C., recrystallization in melt of large particles<br>227° C., all melted; started cooling at 20° C./min<br>30° C., no signs of crystallization; clear, yellow glass<br>new sample, 27° C., particles with B/E; started heating at 10° C./min<br>99° C., change in B/E<br>102° C., continued change in B/E<br>136° C., softening of smaller particles<br>145° C., melting of smaller particles<br>211° C., melting of larger particles; sample is yellow, silicon oil boiling, discontinued heating |
| KF | 3.57% water (~0.7 moles) |
| $^1$H NMR | consistent with structure, no solvent present |

[a]High-resolution XRPD.
[b]Temperatures are rounded to the nearest ° C.; weight loss values are rounded to one decimal place.
[d]First 14 HSM samples were analyzed dry; last 6 HSM samples were analyzed under silicon oil Based on the data obtained, Form B is a crystalline material containing approximately 0.7 moles of water. Form B likely converts to Form A upon heating.

7.6.4 Characterization of Form C of the Esylate Salt of Compound 6

Form C was obtained by precipitation from ethanol and 1-propanol solutions with isopropyl ether (antisolvent). The ethanol and 1-propanol solutions were prepared at approximately 70° C. in an attempt to conduct a cooling experiment; however, no crystallization was observed upon cooling to ambient and subambient temperature. Form C was seen in mixtures with Form A generated by precipitation in various solvents (ethanol, 1-proponal, TFE, and DMF) with antisolvent addition (hexanes, diisopropyl ether, and acetonitrile), as well as by spontaneous precipitation in acetone and precipitation from ethanol with heptane and MIBK when amorphous material was used (FIG. 28 and FIG. 29).

Three scale-up attempts were conducted for Form C by antisolvent precipitation from ethanol with isopropyl ether, summarized in Table 11. In the first attempt on a 400-mg scale, a solution in ethanol with concentration of 9 mg/mL was prepared at room temperature; the material obtained by precipitation with IPE was Form A (lot 011 used, See Table 11 above and FIG. 30, second from top pattern). In the second scale-up attempt, the conditions of the original cooling experiment (concentration of ethanol solution 16 mg/mL) were followed resulting in XRPD pattern C exhibiting pattern A peaks. While in the first scale-up experiment the suspension was left stirring for approximately 0.5 hour after precipitation occurred and before the solid was filtered; in the second experiment stirring was discontinued after solids precipitated from solution. The different outcome of these two experiments suggests possible influence of solution concentration and/or stirring on competitive formation of A and C under conditions used. Form C remained unchanged when reanalyzed by XRPD after 19 days of ambient storage.

In a final attempt, Form C was prepared at a 100-mg scale by dissolving amorphous ethanesulfonate salt of Compound 6 in ethanol at room temperature at a concentration of 16 mg/mL and precipitating via IPE addition without stirring. The XRPD pattern for Form C acquired on INEL is shown in FIG. 31.

The high-resolution XRPD pattern of ethanesulfonate salt of Compound 6, Form C was successfully indexed using X'Pert High Score Plus 2.2a (2.2.1), as illustrated in FIG. 32. Agreement between the allowed peak positions, marked with red bars, and the observed peaks indicates a consistent unit cell determination. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing were performed.

Peak positions were picked for XRPD pattern of Form C of the ethanesulfonate salt of Compound 6. The PANalytical pattern in FIG. 32 and the INEL pattern in FIG. 31 were analyzed for this material, and therefore preferred orientation and particle statistic effects could be assessed through comparison of multiple patterns. Reproducibility between patterns indicates that the particle statistics are adequate. The relative peak intensities are in good agreement between XRPD patterns indicating good orientation statistics. Observed peaks are shown in Table 14A and representative peaks are listed in Table 14B.

TABLE 14

| °2θ | d space (Å) | Intensity (%) |
|---|---|---|
| 5.52 ± 0.20 | 16.009 ± 0.601 | 26 |
| 6.77 ± 0.20 | 13.050 ± 0.397 | 88 |
| 7.48 ± 0.20 | 11.826 ± 0.325 | 89 |
| 9.85 ± 0.20 | 8.981 ± 0.186 | 30 |
| 11.29 ± 0.20 | 7.840 ± 0.141 | 8 |
| 13.17 ± 0.20 | 6.721 ± 0.103 | 15 |
| 13.58 ± 0.20 | 6.523 ± 0.097 | 21 |
| 14.49 ± 0.20 | 6.111 ± 0.085 | 9 |
| 15.00 ± 0.20 | 5.908 ± 0.079 | 4 |
| 16.17 ± 0.20 | 5.483 ± 0.068 | 23 |
| 16.63 ± 0.20 | 5.330 ± 0.064 | 30 |
| 17.17 ± 0.20 | 5.165 ± 0.060 | 24 |
| 17.75 ± 0.20 | 4.996 ± 0.056 | 28 |
| 18.37 ± 0.20 | 4.829 ± 0.053 | 39 |
| 18.76 ± 0.20 | 4.731 ± 0.051 | 15 |
| 19.96 ± 0.20 | 4.449 ± 0.045 | 45 |
| 20.43 ± 0.20 | 4.348 ± 0.043 | 26 |

TABLE 14-continued

| °2θ | d space (Å) | Intensity (%) |
|---|---|---|
| 20.91 ± 0.20 | 4.248 ± 0.041 | 32 |
| 21.41 ± 0.20 | 4.150 ± 0.039 | 28 |
| 21.88 ± 0.20 | 4.062 ± 0.037 | 7 |
| 22.35 ± 0.20 | 3.978 ± 0.035 | 100 |
| 22.73 ± 0.20 | 3.912 ± 0.034 | 17 |
| 22.98 ± 0.20 | 3.870 ± 0.034 | 9 |
| 24.17 ± 0.20 | 3.682 ± 0.030 | 9 |
| 24.64 ± 0.20 | 3.613 ± 0.029 | 2 |
| 25.02 ± 0.20 | 3.559 ± 0.028 | 3 |
| 25.57 ± 0.20 | 3.483 ± 0.027 | 5 |
| 25.92 ± 0.20 | 3.437 ± 0.026 | 2 |
| 26.53 ± 0.20 | 3.360 ± 0.025 | 23 |
| 27.04 ± 0.20 | 3.297 ± 0.024 | 11 |
| 27.45 ± 0.20 | 3.250 ± 0.023 | 8 |
| 28.62 ± 0.20 | 3.120 ± 0.022 | 10 |
| 29.07 ± 0.20 | 3.072 ± 0.021 | 19 |

TABLE 14B

| °2θ | d space (Å) | Intensity (%) |
|---|---|---|
| 5.52 ± 0.20 | 16.009 ± 0.601 | 26 |
| 6.77 ± 0.20 | 13.050 ± 0.397 | 88 |
| 7.48 ± 0.20 | 11.826 ± 0.325 | 89 |
| 9.85 ± 0.20 | 8.981 ± 0.186 | 30 |
| 13.17 ± 0.20 | 6.721 ± 0.103 | 15 |
| 13.58 ± 0.20 | 6.523 ± 0.097 | 21 |
| 16.17 ± 0.20 | 5.483 ± 0.068 | 23 |
| 16.63 ± 0.20 | 5.330 ± 0.064 | 30 |
| 17.17 ± 0.20 | 5.165 ± 0.060 | 24 |
| 17.75 ± 0.20 | 4.996 ± 0.056 | 28 |
| 18.37 ± 0.20 | 4.829 ± 0.053 | 39 |
| 18.76 ± 0.20 | 4.731 ± 0.051 | 15 |
| 19.96 ± 0.20 | 4.449 ± 0.045 | 45 |
| 20.43 ± 0.20 | 4.348 ± 0.043 | 26 |
| 20.91 ± 0.20 | 4.248 ± 0.041 | 32 |
| 21.41 ± 0.20 | 4.150 ± 0.039 | 28 |
| 22.35 ± 0.20 | 3.978 ± 0.035 | 100 |

Characterization data for Form C are summarized in Table 15 below. The proton NMR spectrum acquired on Form C was consistent with the ethanesulfonate salt (FIG. 33).

The thermal analysis results for Form C are shown in FIG. 34. By TGA, Form C exhibits an insignificant weight loss of approximately 0.2% from ambient to 180° C., possibly due to trace amounts of solvent. The dramatic change in the slope of the TGA thermogram at approximately 234° C. is consistent with decomposition.

Three sharp endotherms are observed by DSC at approximately 204, 213, and 221° C. By HSM, a solid to liquid transition was observed at approximately 209° C., which likely corresponds with the sharp endotherm at 204° C. in DSC. Recrystallization to needles was observed at approximately 209° C., possibly due to conversion to another solid form, and was followed by further melting at approximately 222° C., possibly corresponding with the endotherm at 221° C. in DSC. Based on comparison with the DSC data for Form A, the presence of endotherm at 221° C. may indicate conversion to Form A upon heating. Variable temperature XRPD analysis may be conducted to additionally study the thermal behavior of Form C.

TABLE 15

| Analysis | Result |
|---|---|
| XRPD | C |
| DSC[a] | 204° C. (endo, peak; 201° C. onset; ΔH: 68 J/g); 213° C. (endo, peak); 221° C. (endo, peak) |

TABLE 15-continued

| Analysis | Result |
|---|---|
| ¹H NMR | consistent with structure, no solvent present |
| XRPD | C |
| TGA[a] | 0.2% weight loss up to 180° C.; 234° C. (onset, decomposition) |
| HSM | 24° C., white particulates, B/E; started heating at 10° C./min 73° C., no change 137° C., no change 198° C., no change; heating rate changed to 5° C./min 205° C., increasing B/E 209° C., melt/recrystallization (needles) 212° C., melt 218° C., continued melt 222° C., needles melted, few particles with B/E; started cooling at 10° C./min 26° C., no recrystallization upon cooling; yellow/brown glass |

[a]Temperatures are rounded to the nearest ° C.; weight loss values are rounded to one decimal place; reported ΔH values are rounded to the nearest whole number.

Based on the data obtained, Form C is a crystalline unsolvated material melting in the range of approximately 204-209° C. Form C likely converts to Form A upon heating.

7.6.5 Characterization of Form D of the Esylate Salt of Compound 6

Form D of the esylate salt of Compound 6 resulted from complete evaporation of a dimethylformamide solution. XRPD data is shown in FIG. 35. Characterization data for the Form D material are summarized in the following Table 16.

TABLE 16

| Analysis | Result |
|---|---|
| XRPD | D |
| DSC[a] | 73° C., (endo, peak); 108° C. (endo, peak); 170° C. (endo, peak) |
| TGA[a] | 3.2% weight loss from RT to 100° C.; 6.0% weight loss from 100 to 200° C.; 234° C. (onset, decomposition) |
| ¹H NMR | consistent with structure, 0.2 moles of DMF (7.95 ppm) |

[a]Temperatures are rounded to the nearest ° C.; weight loss values are rounded to one decimal place.

The proton NMR spectrum acquired on Form D showed two sets of peaks in the aromatic area. While chemical shifts for one set of peaks were consistent with the ethanesulfonate salt; the second set of peaks with lower integral values may belong to a possible epimerization product formed in acidic conditions upon salt dissociation in DMF due to long duration of the evaporation experiment (18 days). Additional experiments and proton NMR analysis involving the other enantiomer of the ethanesulfonate salt of Compound 6 would be needed to confirm this hypothesis. In an alternative explanation, equilibrium between the protonated and unprotonated forms of Compound 6 in DMSO-d6 (NMR solvent) would likely not be detected by NMR, owing to fast proton transfer, which leads to average chemical shift values. This is evident from the NMR spectrum of the Form A material that exhibits broader peaks rather than two sets of peaks. Based on the NMR spectrum, material D also contains a small amount of DMF (FIG. 36).

The thermal analysis results for Form D are shown in FIG. 37. By DSC, three broad endotherms at approximately 73, 108 and 170° C. are possibly due to dehydration/desolvation, given the observed weight loss of approximately 3.2% (ambient temperature to 100° C.) and 6.0% (100 to 200° C.)

in TGA. Some of the weight loss observed from 100 to 200° C. may be due to DMF or decomposition.

Based on the data obtained, Form D is a crystalline material containing residual dimethylformamide. Additional studies may be conducted to investigate the nature of the second set of peaks in the NMR spectrum of Form D.

7.6.6 Free Base of Compound 6

A new crystalline XRPD pattern designated as Form A of the free base of Compound 6 was observed from precipitation in ethanol with water (antisolvent) when amorphous ethanesulfonate salt of Compound 6 was used. (FIG. 38, top pattern). Summary of the data obtained for Form A of the free base is shown below in Table 16. The proton NMR spectrum of the material was consistent with free base of Compound 6 and showed approximately 0.2 moles of esylate salt present (FIG. 39). The Compound 6 free base was recovered by further evaporation of the aqueous ethanol solution. A similar XRPD pattern exhibiting slight peak shifts was observed from spontaneous precipitation in water, resulting from dissociation of the esylate salt (FIG. 38, bottom pattern). These observations indicate the esylate salt is unstable due to dissociation in water and aqueous ethanol solutions.

The DSC thermogram exhibits a probable melting endotherm at approximately 97° C. followed by a broad endotherm at approximately 196° C. likely due to decomposition (FIG. 40).

TABLE 16

| Analysis | Result |
| --- | --- |
| XRPD | free base |
| DSC[a] | 97° C. (endo, peak); 196° C. (endo, peak) |
| ¹H NMR | consistent with free base, 0.2 moles of esylate salt (1.05 ppm) |

[a]Temperatures are rounded to the nearest ° C.

7.7 Example 6

Preparation of Compound 0

Scheme C

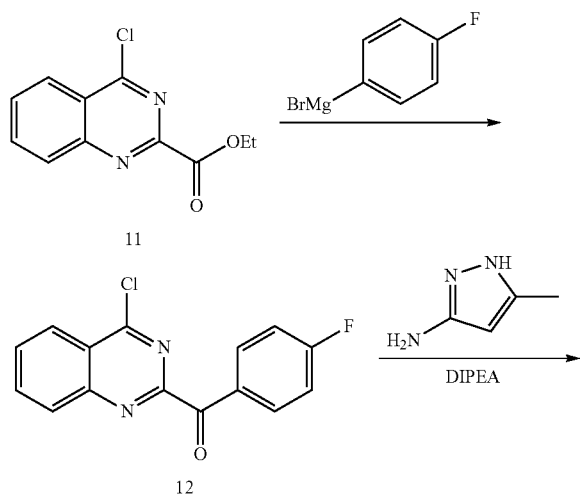

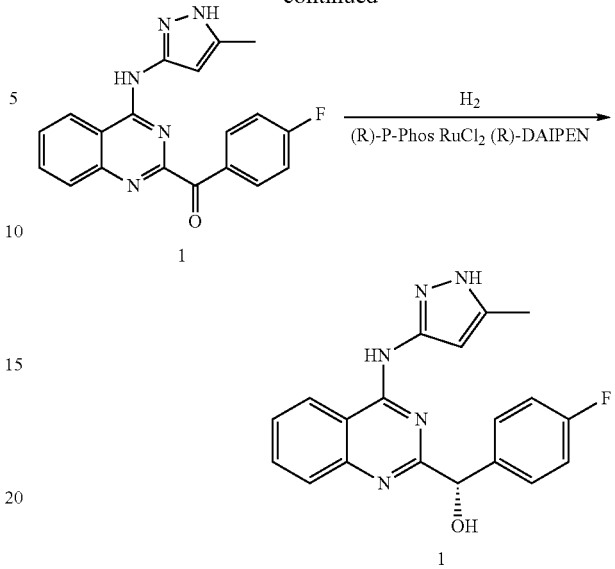

A stirred mixture of (4-fluorophenyl)(4-(5-methy-4H-pyrazol-3-ylamino)quinazolin-2-yl)methanone (16.66 g, 48 mmol) and [(R)—P-Phos RuCl₂ (R)-DAIPEN](217 mg, 0.192 mmol) at room temperature was subjected to five cycles of pressurizing with nitrogen to 40 psi followed by depressurization. Then 1M KOtBu/tBuOH (576 µL, 0.0.576 mmol) in 9:1 i-PrOH/H2O (4 mL) was added and the mixture was subjected to five cycles of pressurizing with nitrogen to 40 psi followed by depressurization. The stirred mixture was then subjected to ten cycles of pressurizing with hydrogen to 435 psi followed by depressurization. The mixture was then stirred at 900 rpm under hydrogen (435 psi) at 40° C. for 18 hrs. The mixture was allowed to cool to room temperature and then carefully vented. The resulting precipitate was collected by filtration and washed with cold MeOH (100 mL) to afford (S)-(4-fluorophenyl)(4-((5-methyl-1H-pyrazol-3-yl)amino)quinazolin-2-yl)methanol as a white solid (13.8 g). Chiral HPLC indicated a >99% enantiomeric excess of the earlier eluting enantiomer.

7.8 Example 7

Preparation of Form A of the Esylate Salt of Compound 0

(S)-(4-fluorophenyl)(4-((5-methyl-1H-pyrazol-3-yl)amino)quinazolin-2-yl)methanol free base (6.0 g, 17.2 mmol, 1.0 equiv.), a stir bar and ethanol (100 mL) were charged to a 250-mL round bottom flask. The flask was stirred and heated to reflux with a heat gun. Ethanesulfonic acid (1.40 mL, 17.2 mmol, 1.0 equiv.) was added drop wise. The slurry partially dissolved. Additional heat (heat gun) was applied until complete dissolution was observed. The flask was stirred and allowed to cool to room temperature. Stirring was continued overnight. The flask was filtered and the contents dried in a vacuum oven (45° C., ~20 torr) overnight to yield 5.02 g, 10.9 mmol, 64%.

7.8.1 Characterization of Form A of Esylate Salt of Compound 0

FIG. 41 shows the DSC thermogram for Form A of the esylate salt of Compound 0. The DSC thermogram FIG. 42 shows the TGA thermogram for Form A of the esylate salt of Compound 0. By TGA, a minimal weight loss of approximately 0.345% of is observed up to 210° C.

7.9 Example 8

Pharmacokinetic Study in Rat

Male Sprague-Dawley rats were dosed orally with the methanesulfonate salt, hydrobromide salt, or Form A of the ethanesulfonate salt of Compound 6 or dosed orally with the hydrobromide salt of (4-fluorophenyl)(4-((5-methyl-1H-pyrazol-3-yl)amino)quinazolin-2-yl)methanol. Blood samples were collected over a 24 hour time-course for determination of pharmacokinetic parameters.

Pre-catheterized (jugular vein), male Sprague-Dawley rats (230-300 g) obtained from Charles River (Hollister, Calif.) were acclimated in the Ambit vivarium (San Diego, Calif.) for at least three days after delivery and before entering a study. Rats were fasted overnight before dosing. All rats received 10 mg/kg oral dose (PO) using dosing syringe of a test compound in capsule. Blood samples (approximately 1.0 mL) were collected after dosing at specified time points (15 min, 30 min, 1, 2, 4, 6, and 24 hrs) into tubes containing K3EDTA. The samples collected were placed on wet ice/ice block and processed for plasma within 15 min. For each sample, plasma was separated and stored frozen at approximately −20° C. until analysis.

Plasma samples, calibration, and quality control standards (50 μL) were extracted with five volumes of acetonitrile containing an internal standard (25 ng/mL N-(5-cyclopropyl-1H-pyrazol-3-yl)-2-(difluoro(4-fluorophenyl)methyl)quinazolin-4-amine) and analyzed using LC-MS/MS (Sciex 4000 Qtrap) on a Regis RegisCell 5 μm column (4.6×250 mm), eluting isocratically with hexane/isopropyl alcohol (85:15) at a flow rate of 1.75 mL/min over 9.5 min, and monitoring the 350/332 Da parent mass/fragment mass transition. Each enantiomer's peak area was integrated separately to quantify the R- and S-enantiomer levels, while both peaks were integrated together as a single integral to quantify the level of the racemic compound.

Pharmacokinetic parameters were then calculated from the normalized LC-MS/MS peak areas using the noncompartmental model and linear trapezoidal estimation method using the WinNonlin software (v5.2, Pharsight Corporation, Mountain View, Calif.).

The pharmacokinetic properties of racemic (4-fluorophenyl)(4-((5-methyl-1H-pyrazol-3-yl)amino)quinazolin-2-yl)methanol hydrochloride were determined after administration of the racemic compound. The pharmacokinetic properties of the two enantiomers in the racemic compound were also determined. The results are summarized in FIG. 43 and Table 17.

TABLE 17

Pharmacokinetic parameters of the racemic compound

| Compound/Analyte | Salt Form | Dose (mg/kg) | $C_{max}$ (μM) | $T_{max}$ (hrs) | $AUC_{0-6}$ (hr · μM) | $AUC_{0-\infty}$ (hr · μM) |
|---|---|---|---|---|---|---|
| Compound 6/Compound 6 | Mesylate | 10 | 1.57 | 2.7 | 5.42 | 6.02 |
| Compound 6/Compound 6 | Esylate | 10 | 1.69 | 3.27 | 6.38 | 9.72 |
| Compound 6/Compound 6 | HBr | 10 | 2.03 | 3.3 | 6.11 | 7.80 |
| (4-fluorophenyl)(4-(95-methyl-1H-pyrazol-3-yl)amino)quinazolin-2-yl)methanol/Compound 6 | HBr | 5* | 1.8 | 2.2 | 4.73 | 5.38 |

*Compound 6 assumed to be 5 mpk from a 10 mpk (4-fluorophenyl) (4-((5-methyl-1H-pyrazol-3-yl)amino)quinazolin-2-yl)methanol dose
Dosed salt of Compound 6 at 10 mpk in capsules
Compound 6 levels in (4-fluorophenyl)(4-((5-methyl-1H-pyrazol-3-yl)amino)quinazolin-2-yl)methanol hydrobromide salt capsule dose shown for comparison (assume 5 mpk Compound 6)
No exposure at 24 hour, similar to (4-fluorophenyl)(4-((5-methyl-1H-pyrazol-3-yl)amino)quinazolin-2-yl)methanol capsule dose Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A solid form comprising an esylate salt of the compound of formula (I):

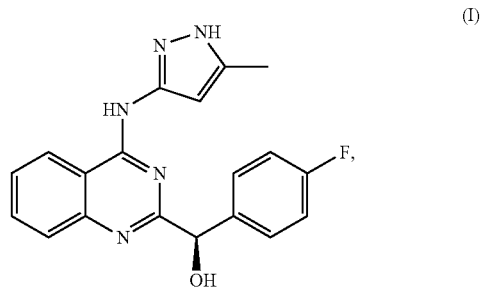 [SMILES: Cc1cc(Nc2nc([C@H](O)c3ccc(F)cc3)nc3ccccc23)n[nH]1]

having an XRPD pattern comprising peaks at approximately 6.29, 16.24 and 20.55°2θ when analyzed using copper Kα radiation.

2. The solid form of claim 1 which further comprises solvent.

3. The solid form of claim 1 which further comprises water.

4. The solid form of claim 1 which is substantially free of solvent.

5. The solid form of claim 1 which is substantially free of water.

6. The solid form of claim 1 which is anhydrous.

7. The solid form of claim 1 which is Form A crystal form of the esylate salt of the compound of formula (I).

8. The solid form of claim 1 having an XRPD pattern further comprising peaks at approximately 6.90, 17.58 and 21.49°2θ when analyzed using copper Kα radiation.

9. The solid form of claim 8 having an XRPD pattern further comprising peaks at approximately 18.03, 20.31 and 22.19°2θ when analyzed using copper Kα radiation.

10. The solid form of claim 1 having an XRPD pattern substantially as presented in FIG. 16.

11. The solid form of claim 1 having an XRPD pattern substantially as presented in FIG. 17.

12. The solid form of claim 1 having a DSC thermogram comprising an endothermic event with an onset temperature of approximately 218° C.

13. The solid form of claim 1 which is substantially pure.

14. The solid form of claim 1 which is substantially free of chemical impurities.

15. The solid form of claim 1 which is substantially free of physical impurities.

16. A pharmaceutical composition comprising the solid form of claim 1 and a pharmaceutically acceptable excipient.

17. A crystal form comprising esylate salt of the compound of the following formula:

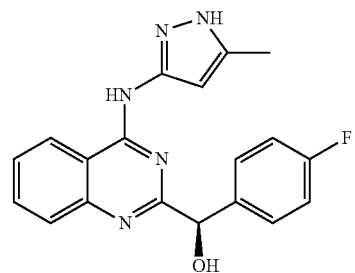 [SMILES: Cc1cc(Nc2nc([C@H](O)c3ccc(F)cc3)nc3ccccc23)n[nH]1]

which is selected from the group consisting of:
a. Form B of the esylate salt of the compound characterized by XRPD peaks located at one or both of the following approximate positions: 6.17 and 16.82 degrees 2θ;
b. Form C of the esylate salt of the compound characterized by XRPD peaks located at one, two or three of the following approximate positions: 6.77, 7.48 and 22.35 degrees 2θ; and
c. Form D of the esylate salt of the compound characterized by XRPD peaks located at one or both of the following approximate positions: 6.5 and 13.4 degrees 2θ.

18. A pharmaceutical composition comprising the crystal form of claim 17 and a pharmaceutically acceptable excipient.

* * * * *